United States Patent
Spaete et al.

(10) Patent No.: US 7,208,165 B2
(45) Date of Patent: *Apr. 24, 2007

(54) HUMAN CYTOMEGALOVIRUS DNA SEQUENCES

(75) Inventors: Richard Roger Spaete, Emerald Hills, CA (US); Tai-An Cha, San Ramon, CA (US)

(73) Assignee: MedImmune Vaccines, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/293,112

(22) Filed: Dec. 5, 2005

(65) Prior Publication Data

US 2006/0240446 A1   Oct. 26, 2006

Related U.S. Application Data

(60) Continuation of application No. 10/394,848, filed on Mar. 21, 2003, now abandoned, which is a division of application No. 09/892,100, filed on Jun. 26, 2001, now Pat. No. 6,635,477, which is a division of application No. 09/527,657, filed on Mar. 17, 2000, now Pat. No. 6,291,236, which is a division of application No. 09/253,682, filed on Feb. 18, 1999, now Pat. No. 6,040,170, which is a division of application No. 08/926,922, filed on Sep. 10, 1997, now Pat. No. 5,925,751, which is a division of application No. 08/414,926, filed on Mar. 31, 1995, now Pat. No. 5,721,354.

(51) Int. Cl.
*A61K 39/245* (2006.01)

(52) U.S. Cl. .............. 424/230.1; 424/204.1; 435/6

(58) Field of Classification Search ............ 424/230.1, 424/204.1, 199.1; 435/6
See application file for complete search history.

(56) References Cited

U.S. PATENT DOCUMENTS

| | | | |
|---|---|---|---|
| 5,075,213 A | 12/1991 | Pande et al. | |
| 5,194,256 A | 3/1993 | Rasmussen et al. | |
| 5,721,354 A * | 2/1998 | Spaete et al. ............ | 536/23.72 |
| 6,040,170 A * | 3/2000 | Spaete et al. ............ | 435/252.3 |

OTHER PUBLICATIONS

Zaia, Comparative Analysis of Human Cytomegalovirus a-Sequence in Multiple Clinical Isolates etc., J Clin. Microbio. 28 (1990) 2602-07.
Pande, Human Cytomegalovirus Strain Towne pp65 Gene: Nucleotide Sequence and Expression in *Escherichia coli*, Virology 182 (1991) 220-28.
Pande, Human Cytomegalovirus Strain pp28 Gene: Comparison to pp28 of HCMV AD169 etc, Virology 194 (1991) 762-67.
Chou, Analysis of Interstrain Variation in Cytomegalovirus Glycoprotein B etc, J Inf Diseases 163 (1991) 1229-34.
Robson, Primate Cytomegalovirus Assembly Protein: Genome Location and Nucleotide Sequence, J Virol 63 (1989) 669-76.
Lehner, Comparative Sequence Analysis of Human Cytomegalovirus Strains, J Clin Microbiol 29 (1991) 2494-2502.
Fries, Frequency Distribution of Cytomegalovirus Envelop Glycoprotein Geneotypes etc, J Inf Diseases 169 (1994) 478-83.
Quinnan, Comparative Virulence and Immunogenicity of the Towne Strain etc, Annals of Int Med 101 (1984) 478-83.
Plotkin, Lancet 1 (1984) 528-30.
Plotkin, Protective Effects of Towne Cytomegalovirus Vaccine etc, J Inf Disease 159 (1989) 860-65.
Huang, Detection of Human Cytomegalovirus and Analysis of Strain Variation, Yale J Biol and Med 49 (1976) 29-43.
Kilpatrick, Analysis of Cytomegalovirus Genomes with Restriction Endonucleases etc, J virol 18 (1976) 1095-1105.
LaFemina, Structural Organization of the DNA Molecules from Human Cytomegalovirus, in "Animal Virus Genetics", Field, BN & R Joenish, eds., Academic Press, NY 1980, pp. 39-53.
Chandler, Comparison of Restriction Site Polymorphisms Among Clinical Isolates and Laboratory Strains of Human Cytomegalovirus, J Gen Virol 67 (1986) 2179-92.
Spaete, Human Cytomegalovirus Strain Towne Glycoprotein B etc, Virology 167 (1988) 207-25.
Marshall, Cytomegalovirus Vaccines, in "The Human Herpesvirus," RJ Whitley, B Roizman and C Lopez, eds., Raven Press, NY, pp. 381-395, (1993).
Alford, Cytomegalovirus, in "The Human Herpesviruses," RJ Whitley, B Roizman and C Lopez, eds., Raven Press, NY, pp. 227-255, (1993).
Chou, Differentiation of Cytomegalovirus Strains by Restriction Analysis etc, J Inf Diseases 162 (1990) 738-42.
Pritchett, DNA Nucleotide Sequence Heterogeneity Between the Towne and AD 169 Strains of Cytomegalovirus, J Virol 36 (1980) 152-61.
Altschul et al., Basic Local Alignment Search Tool, J Mol Biol (1990) 215: 403-410.
Brutlag et al., BLAZE(TM): An Implementation of the Smith-Waterman Sequence Comparison Algorithm on A Massively Parallel Computer, Comp. Chem. (1993) 17: 203-207.
Xu et al., Constructing Gene Models From Accurately Predicted Exons: An Application of Dynamic Programming, Comput. Appl. Biosci. (1994) 10: 613-623.

* cited by examiner

*Primary Examiner*—Ali R. Salimi

(57) ABSTRACT

Provided are novel Toledo and Towne human cytomegalovirus DNA sequences (HCMV) and proteins encoded thereby. The sequences are useful in methods and compositions for detecting HCMV infections and in immunogenic compositions for Preventing HCMV infections.

11 Claims, 53 Drawing Sheets

```
         10         20         30         40         50         60
CGCTGTAGGG ATAAATAGTG CGATGGCGTT TGTGGGAGAA CGCAGTAGCG ATGGGTTGCG
GCGACATCCC TATTTATCAC GCTACCGCAA ACACCCTCTT GCGTCATCGC TACCCAACGC
                                                      ↑
                                                     UL133

70         80         90        100        110        120
ACGTGCACGA TCCTTCGTGG CAATGCCAAT GGGGCGTTCC CACGATTATC GTGGCCTGAA
TGCACGTGCT AGGAAGCACC GTTACGGTTA CCCCGCAAGG GTGCTAATAG CACCGGACCT 130        140        150        160        170        180
TAACATGCGC GGCTTTAGGA ATTTGGTGTT TGGCGGGATC GTCGGCGGAT GTCTCTTCGG
ATTGTACGCG CCGAAATCCT TAAACCACAA ACCGCCCTAG CAGCCGCCTA CAGAGAAGCC 190        200        210        220        230        240
GACCCGGCAT CGCAGCCGTA GTCGGCTGTT CTGTTTTCAT GATTTCCCTC TGCGCGTATC
CTGGGCCGTA GCGTCGGCAT CAGCCGACAA GACAAAAGTA CTAAAAGGAG ACGCGCATAG 250        260        270        280        290        300
TCATCCGTTA CCGGGAATTC TTCAAAGACT CCGTAATCGA CCTCCTTACC TGCCGATGGG
AGTAGGCAAT GGCCCTTAAG AAGTTTCTGA GGCATTAGCT GGAGGAATGG ACGGCTACCC 310        320        330        340        350        360
TTCGCTACTG CAGCTGCAGC TGTAAGTGCA GCTGCAAATG CATCTCGGGC CCCTGTAGCC
AAGCGATGAC GTCGACGTCG ACATTCACGT CGACGTTTAC GTAGAGCCCG GGGACATCGG 370        380        390        400        410        420
GCTGCTGTTC AGCGTGTTAC AAGGAGACGA TGATTTACGA CATGGTCCAA TACGGTCATC
CGACGACAAG TCGCACAATG TTCCTCTGCT ACTAAATGCT GTACCAGGTT ATGCCAGTAG 430        440        450        460        470        480
GACGGCGTCC CGGACACGGC GACGATCCCG ACAGGGTGAT CTGCGAGATA GTCGAGAGTC
CTGCCGCAGG GCCTGTGCCG CTGCTAGGGC TGTCCCACTA GACGCTCTAT CAGCTCTCAG
```

FIG._1A-1

```
           490        500        510        520        530        540
     CCCCGGTTTC GGCGCCGACG GTGTCCGTCC CCCGCCGTC GGAGGAGTCC CACCAGCCCG
     GGGGCCAAAG CCGCGGCTGC CACAGGCAGG GGGGCGGCAG CCTCCTCAGG GTGGTCGGGC

UL134      550        560        570        580        590        600
     ┌TCATCCCACC GCAGCCGCCA GCACCGACAT CGGAACCCAA ACCGAAGAAA GGTAGGGCGA
     ├AGTAGGGTGG CGTCGGCGGT CGTGGCTGTA GCCTTGGGTT TGGCTTCTTT CCATCCCGCT
     ▼
           610        620        630        640        650        660
     AAGATAAACC GAAGGGTAGA CCGAAAGACA AACCTCCGTG CGAACCGACG GTGAGTTCAC
     TTCTATTTGG CTTCCCATCT GGCTTTCTGT TTGGAGGCAC GCTTGGCTGC CACTCAAGTG 670        680        690        700        710        720
     AACCACCGTC GCAGCCGACG GCAATGCCCG GCGGTCCGCC CGACGCGCCT CCCCCCGCCA
     TTGGTGGCAG CGTCGGCTGC CGTTACGGGC CGCCAGGCGG GCTGCGCGGA GGGGGGCGGT 730        740        750        760        770        780
     TGCCGCAGAT GCCACCCGGC GTGGCCGAGG CGGTACAAGC TGCCGTGCAG GCGGCCGTGG
     ACGGCGTCTA CGGTGGGCCG CACCGGCTCC ACGGCACGTC ACGGCACACC CGCCGGCACC 790        800        810        820   UL133  830        840
     CCGCGGCTCT ACAACAACAG CAGCAGCATC AGACCGGAAC GTAA┌CCCGCC CCCGGTGCGA
     GGCGCCGAGA TGTTGTTGTC GTCGTCGTAG TCTGGCCTTG CATT└GGGCGG GGGCCACGCT
                                                   ▲
           850        860        870        880        890        900
     ┐CCTTGCCAGA TCCGACTTGG CGCACATCTC CTTCCTCAAT GTTTGGACAA TAAACACATT
     ┘ATTCCTTAAA AGGCTGAACC GCGTGTAGAG GAAGGAGTTA CAAACCTGTT ATTTGTGTAA 910        920        930        940  UL135  950        960
     CCTTGCCAAA AAATGACGTT TCCAGAAATC CAAGGCATAA ┌ATGTCCGTAC ACCGGCCCTT
     GGAACGGTTT TTTACTGCAA AGGTCTTTAG GTTCCGTATT └TACAGGCATG TGGCCGGGAA
                                                ▲
```

FIG._1A-2

```
      970         980         990        1000        1010        1020
CCCAACACGG  AGTTTGAGAT  TCCAAGCAGG  AGAGAAGATC  ATGGTGTGGA  TATGGCTCGG
GGGTTGTGCC  TCAAACTCTA  AGGTTCGTCC  TCTCTTCTAG  TACCACACCT  ATACCGAGCC 1030        1040        1050        1060        1070        1080
CATCGGGCTC  CTCGGCGGTA  CCGGACTGGC  TTCCCTGGTC  CTGGCCATTT  CCTTATTTAC
GTAGCCCGAG  GAGCCGCCAT  GGCCTGACCG  AAGGGACCAG  GACCGGTAAA  GGAATAAATG
                                                   UL134

1090        1100        1110        1120        1130        1140
CCAGCGCCGA  GGCCGCAAGC  GATCCGTCG   GACTTCGTCG  CGAGGCCGGC  TCCCGGGTGC
GGTCGCGGCT  CCGGCGTTCG  CTAGGCTGCT  CTGAAGCAGC  GCTCCGGCCG  AGGGCCCACG 1150        1160        1170        1180        1190        1200
TGCTTCTGAT  AAGCGTGGTG  CCTGCGCGTG  CTGCTATCGA  AATCCGAAAG  AAGACGTCGT
ACGAAGACTA  TTCGCACCAC  GGACGCGCAC  GACGATAGCT  TTAGGCTTTC  TTCTGCAGCA 1210        1220        1230        1240        1250        1260
CGAGCCGCTG  GATCTGGAAC  TGGGCTCAT   GCGGGTGAAC  ACCCACCCGC  CGACGCCGCA
GCTCGGCGAC  CTAGACCTTG  ACCCCGAGTA  CGCCCACTTG  TGGGTGGGCG  GCTGCGGCGT 1270        1280        1290        1300        1310        1320
GGTGCCGCGG  TGTACGTCGC  TCTACATAGG  AGAGGATGGT  CTGCCGATAG  ATAAACCCGA
CCACGGCGCC  ACATGCAGCG  AGATGTATCC  TCTCCTACCA  GACGGCTATC  TATTTGGGCT 1330        1340        1350        1360        1370        1380
GTTTCCTCCG  GCGCGGTTCG  AGATCCCCGA  CGTATCCACG  CCGGGAACGC  CGACCAGCAT
CAAAGGAGGC  CGCGCCAAGC  TCTAGGGGCT  GCATAGGTGC  GGCCCTTGCG  GCTGGTCGTA 1390        1400        1410        1420        1430        1440
CGGCCGATCT  CCGTCGCATT  GCTCCTCGTC  GAGCTCTTTG  TCGTCCTCGA  CCAGCGTCGA
GCCGGCTAGA  GGCAGCGTAA  CGAGGAGCAG  CTCGAGAAAC  AGCAGGAGCT  GGTCGCAGCT
```

FIG._1B-1

```
      1450       1460       1470       1480       1490       1500
CACGGTGCTG TATCAGCCGC CGCCATCCTG GAAGCCACCT CCGCCGCCCG GGCGCAAGAA
GTGCCACGAC ATAGTCGGCG GCGGTAGGAC CTTCGGTGGA GGCGGGGGC  CCGCGTTCTT 1510       1520       1530       1540       1550       1560
GCGGCCGCCT ACGCCGCCGG TCCGGGCCCC CACCACGCGG CTGTCGTCGC ACAGACCCCC
CGCCGGCGGA TGCGGCGGCC AGGCCCGGGG GTGGTGCGCC GACAGCAGCG TGTCTGGGGG 1570       1580       1590       1600       1610       1620
GAGGCCGATA CCCGCGCCGC GTAAGAAACCT GAGCACGCCG CCCACCAAGA AAACGCCGCC
CTGCCGGCTAT GGGCGCGGCG CATTCTTGGA CTCGTGCGGC GGGTGGTTCT TTTGCGGCGG 1630       1640       1650       1660       1670       1680
GCCCACGAAA CCCAAGCCGG TCGGCTGGAC ACCGCCGGTG ACACCCAGGC CCTTCCCGAA
CGGGTGCTTT GGGTTCGGCC AGCCGACCTG TGGCGGCCAC TGTGGGTCCG GGAAGGGCTT 1690       1700       1710       1720       1730       1740
AACGCCGACG CCACAAAAGC CGCCGCGGGA TCCGAGACTA CCGCGCACCG TCGGTCTGGA
TTGCGGCTGC GGTGTTTTCG GCGGCGCCCT AGGCTCTGAT GGCGCGTGGC AGCCAGACCT 1750       1760       1770       1780       1790       1800
GAATCTCTCG AAGGTGGGAC TCTCGTGTCC CTGTCCCCGA CCCCGCACGC CGACGGAGCC
CTTAGAGAGC TTCCACCCTG AGAGCACAGG GACAGGGGCT GGGGCGTGCG GCTGCCTCGG 1810       1820       1830       1840       1850       1860
GACCACGCTG CCTATCGTGT CGGTTTCCGA GCTAGCCCCG CCTCCTCGAT GGTCGGACAT
CTGGTGCGAC GGATAGCACA GCCAAAGGCT CGATCGGGGC GGAGGAGCTA CCAGCCTGTA
```

FIG._1B-2

```
     1870           1880           1890           1900           1910           1920
CGAGGAACTC     TTGGAACAGG     CGGTGCAGAG     CGTCATGAAG     GACGCCGAGT     CGATGCAGAT
GCTCCTTGAG     AACCTTGTCC     GCCACGTCTC     GCAGTACTTC     CTGCGGCTCA     GCTACGTCTA

UL135 1930           1940           1950           1960           1970           1980
GACCTGAGAC     CGAAAGAGCG     AGCCGCGTCCG    TTGTACAGTT     GTATAGCAGC     ACACGCCTTC
CTGGACTCTG     GCTTTCTCGC     TCGCGCAGGC     AACATGTCAA     CATATCGTCG     TGTGCGGAAG 1990           2000           2010     2020 UL136 2030           2040
CCTCTTTTTC     ACCGCAGCTA     AGAGAGAGAA     AGAGAGTATG     TCAGTCAAGG     GCGTGAGAT
GGAGAAAAAG     TGGCGTCGAT     TCTCTCTCTT     TCTCTCATAC     AGTCAGTTCC     CGCACCTCTA 2050           2060           2070           2080           2090           2100
GCCAGAAATG     ACGTGGGACT     TGGACGTTAG     AAATAAATGG     CGGCGTCGAA     AGGCCCTGAG
CGGTCTTTAC     TGCACCCTGA     ACCTGCAATC     TTTATTTACC     GCCGCAGCTT     TCCGGGACTC 2110           2120           2130           2140           2150           2160
TCGCATTCAC     CGGTTCTGGG     AATGTCGGCT     ACGGGTGTGG     TGGCTGAGTG     ACGCCGGCGT
AGCGTAAGTG     GCCAAGACCC     TTACAGCCGA     TGCCCACACC     ACCGACTCAC     TGCGGCCGCA 2170           2180           2190           2200           2210           2220
AAGAGAAACC     GACCCACCGG     GTCCCCGACG     CCGCCCGACT     TGGATGACCG     CGGTGTTTCA
TTCTCTTTGG     CTGGGTGGCC     CAGGGGCTGC     GGCGGGCTGA     ACCTACTGGC     GCCACAAAGT 2230           2240           2250           2260           2270           2280
CGTTATCTGT     GCCGTTTTTGC    TTACGCTTAT     GATTATGGCC     ATCGGGCGC     TCATCGCGTA
GCAATAGACA     CGGCAAAACG     AATGCGAATA     CTAATACCGG     TAGCCGCGCG     AGTAGCGCAT 2290           2300           2310           2320           2330           2340
CTTAAGATAT     ACAGTTGGCG     ACACATGCTC     AGACATGCTC     CACGATCTAT     TTTGCGGCTG
GAATTCTATA     ATGGTGGTCC     TGTCAACCGC     TCTGTACGAG     GTGCTAGATA     AAACGCCGAC
```

*FIG._1C-1*

```
      2350             2360             2370             2380             2390             2400
TCATTATCCC       GAGAAGTGCC       GTCGGCACCA       CGAGCGGCAG       AGAAGGAGAC       GGCAAGCCAT
AGTAATAGGG       CTCTTCACGG       CAGCCGTGGT       GCTCGCCGTC       TCTTCCTCTG       CCGTTCGGTA 2410             2420             2430             2440             2450             2460
GGATGTGCCC       GACCCGGAAC       TCGGCGACCC       GGCCCGGCGG       CCGTTGAACG       GAGCTATGTA
CCTACACGGG       CTGGGCCTTG       AGCCGCTGGG       CCGGGCGGCC       GGCAACTTGC       CTCGATACAT 2470             2480             2490             2500             2510             2520
CTACGGCAGC       GGCTGTCGCT       TCGACACGGT       GGAAATGGTG       GACGAGACGA       GACCCGCGCC
GATGCCGTCG       CCGACAGCGA       AGCTGTGCCA       CCTTTACCAC       CTGCTCTGCT       CTGGGCGCGG 2530             2540             2550             2560             2570             2580
GCCGGCGCTG       TCATCGCCCG       AAACCGGCGA       CGATAGCAAC       GACGACGCGG       TTGCCGGCGG
CGGCCGCGAC       AGTAGCGGGC       TTTGGCCGCT       GCTATCGTTG       CTGCTGCGCC       AACGGCCGCC 2590             2600             2610             2620             2630             2640
AGGTGCTGGC       GGGTAACAT CACCCGCGAC       TCGTACGACG       TCGCCGAACG       CACTGCTGCC
TCCACGACCG       CCCCATTGTA GTGGGCGCTG       AGCATGCTGC       AGCGGCTTGC       GTGACGACGG
                         UL137

2650             2660             2670             2680             2690             2700
AGAATGGATG       GATGCGGTGC       ATGTGGCGGT       CCAAGCCGCC       GTTCAAGCGA       CCGTGCAAGT
TCTTACCTAC       CTACGCCACG       TACACCGCCA       GGTTCGGCGG       CAAGTTCGCT       GGCACGTTCA 2710             2720             2730       UL136 2740             2750             2760
CGGGAGCCCG       CGGAGAACG       CCGTATCTCC       CGCTACGTAA       GAGGGTTGAG       GGGGCCGTTC
AAGTGGCCCG       GCCCTCTTGC       GGCATAGAGG       GCGATGCATT       CTCCCAACTC       CCCCGGCAAG 2770             2780             2790             2800             2810             2820
CCGGCGCGAGT       GCTGTACAAA       AGAGAGAGAC       TGGGACGTAG       ATCCGGACAG       AGGACGGTCA
GGCGGCGCTCA       CGACATGTTT       TCTCTCTCTG       ACCCTGCATC       TAGGCCTGTC       TCCTGCCAGT
```

FIG._1C-2

```
UL138  2830          2840          2850          2860          2870          2880
CCATGGACGA    TCTGCCGCTG    AATGTCGGGT    TACCCATCAT    CGGCGTGATG    CTCGTGCTGA
GGTACCTGCT    AGACGGCGAC    TTACAGCCCA    ATGGGTAGTA    GCCGCACTAC    GAGCACGACT 2890          2900          2910          2920          2930          2940
TCGTGGCCAT    CCTCTGCTAT    CTGGCTTACC    ACTGGCACGA    CACCTTCAAA    CTGGTGCGCA
AGCACCGGTA    GGAGACGATA    GACCGAATGG    TGACCGTGCT    GTGGAAGTTT    GACCACGCGT
UL137
       2950          2960          2970          2980          2990          3000
TGTTTCTGAG    CTACCGCTGG    CTGATCCGCT    GTTGCGAGCT    GTACGGGGAG    TACGAGCGCC
ACAAAGACTC    GATGGCGACC    GACTAGGCGA    CAACGCTCGA    CATGCCCCTC    ATGCTCGCGG 3010          3020          3030          3040          3050          3060
GGTTCGCGGA    CCTGTCGTCT    CTGGGCCTCG    GCGCCGTACG    GCGGGAGTCG    GACAGACGAT
CCAAGCGCCT    GGACAGCAGA    GACCCGGAGC    CGCGGCATGC    CGCCCTCAGC    CTGTCTGCTA 3070          3080          3090          3100          3110          3120
ACCGTTTCTC    CGAACGGCCC    GACGAGATCT    TGGTCCGTTG    GGAGGAAGTG    TCTTCCCAGT
TGGCAAAGAG    GCTTGCCGGG    CTGCTCTAGA    ACCAGGCAAC    CCTCCTTCAC    AGAAGGGTCA 3130          3140          3150          3160          3170          3180
GCAGCTACGC    GTCGTCGCGG    ATAACAGACC    GCCGTGTGC    TTCATCGTCT    TCGTCGTCGG
CGTCGATGCG    CAGCAGCGCC    TATTGTCTGG    CGGCGCACCC    AAGTAGCAGA    AGCAGCAGCC 3190          3200          3210          3220          3230          3240
TCCACGTCGC    TAGCCAGAGA    AACAGGCTGC    CTCCGCCGGA    CATGGCGGTG    ACGGCGCCGC
AGGTGCAGCG    ATCGGTCTCT    TTGTCCGACG    GAGGCGGCCT    GTACCGCCAC    TGCCGCGGCG 3250          3260          3270          3280          3290          3300
TGACCGACGT    CGATCTGTTG    AAACCCGTGA    CGGGATCCGC    GACGCAGTTC    ACCACGTAG
ACTGGCTGCA    GCTAGACAAC    TTTGGGCACT    GCCCTAGGCG    CTGCGTCAAG    TGGTGGCATC
```

FIG._1D-1

```
            3310       3320       3330       3340       3350       3360
      CCATGGTACA TTATCATCAA GAGTACACGT GAATGAGAAA AAGAAAAAAG AGGGGAGCGG
      GGTACCATGT AATAGTAGTT CTCATGTGCA CTTACTCTCTT TTCTTTTTTC TCCCCTCGCC
                                        UL138

3370       3380       3390       3400       3410       3420
      ATCGCGATAA TGTCGCTTTG ACATTCTCTG CTCGATCTAC TCAGCGTCTG CACGAAACGG
      TAGCGCTATT ACAGCGAAAC TGTAAGAGAC GAGCTAGATG AGTCGCAGAC GTGCTTTGCC 3430       3440       3450       3460       3470       3480
      CATCCGCACG GAGGCGAGCC CAAGCGTATC TGCAGCAAGC GGTTCTTTCC CTCGGTGATG
      GTAGGCGTGC CTCCGCTCGG GTTCGCATAG ACGTCGTTCG CCAAGAAAGG GAGCCACTAC 3490       3500       3510       3520       3530       3540
      GTGGCAGCAT CGGTGGCGGG AGCTTGTTCG GACGATGGAC GGTGAGGAGT CCCTGGCGAT
      CACCGTCGTA GCCACCGCCC TCGAACAAGC CTGCTACCTG CCACTCCTCA GGGACCGCTA 3550       3560       3570       3580       3590       3600
      CAGGGCGGCTC CCGGGTGTGG AGTTCAACGG GTGGTAATGG TGGCGGTGAT CGGTGTTAGA
      GTCCGCCGAG GGCCCACACC TCAAGTTGCC CACCATTACC ACCGCCACTA GCCACAATCT 3610       3620       3630       3640       3650       3660
      AAACGGTGGC CCTGGCAAAC ATATATCTAC TGTAAACCCT CTGCTCTGTT AATAAAAAGC
      TTTGCCACCG GGACCGTTTG TATATAGATG ACATTTGGGA GACGAGACAA TTATTTTTCG 3670       3680       3690       3700       3710       3720
      ACACTTTTCA CATGAGTTCG TAATTTTATT GTGTAGTGGA AATTTTTACG TCATTGGGAA
      TGTGAAAAGT GTACTCAAGC ATTAAAATAA CACATCACCT TTAAAAATGC AGTAACCCTT 3730       3740       3750       3760       3770       3780
      ACCCCAGAAT AATGTGCATA AATGTGCATA TCACCGGGGG TTCCCTGTCA GTACGAATGT
      TGGGGTCTTA CTTTCTCATA TTACACGTAT AGTGGCCCCC AAGGGACAGT CATGCTTACA
```

FIG._1D-2

```
        3790       3800       3810       3820       3830       3840
ACACAACGCG GGTTACATTA CGATAAACTT TCCGTAAAA  CGATGCCGAT ACAGCGTGTA
TGTGTTGCGC CCAATGTAAT GCTATTTGAA AGGCCATTTT GCTACGGCTA TGTCGCACAT 3850       3860       3870       3880       3890       3900
TAACGCTGAT TGTTACGACA AACGAGTTGG TATATCCATT ATATAGTAAC GAACATGCTG
ATTGCGACTA ACAATGCTGT TTGCTCAACC ATATAGGTAA TATATCATTG CTTGTACGAC
                                                         UL139

3910       3920       3930       3940       3950       3960
TGGATATTAG ACTCGCCGCA TCGGGCGAGTG AAACCACTAC AGGTACCAGC
TTTTATTGC                                                
ACCTATAATC AAAATAAACG TGAGCGGCGT AGCCGCTCAC TTTGGTGATG TCCATGGTCG 3970       3980       3990       4000       4010       4020
TCTAATTCCA GTCAATCTAC TAGTGCTACC GCCAACACGA CCGTATCGAC ATGTATTAAT
AGATTAAGGT CAGTTAGATG ATCACGATGG CGGTTGTGCT GGCATAGCTG TACATAATTA 4030       4040       4050       4060       4070       4080
GCCTCTAACG GCAGTAGCTG GACAGTACCA CAGCTCGCGC TGCTTGCCGC TAGCGGCTGG
CGGAGATTGC CGTCATCGAC CTGTCATGGT GTCGAGCGCG ACGAACGGCG ATCGCCGACC 4090       4100       4110       4120       4130       4140
ACATTATCTG GACTCCTTCT CTTATTACC  TGCTGCTTTT GCTGCTTTTG GCTAGTACGT
TGTAATAGAC CTGAGGAAGA GAATAATGG  ACGACGAAAA CGACGAAAAC CGATCATGCA 4150       4160       4170       4180       4190       4200
AAAATCTGCA GCTGCTGCGG CAACTCCTCC GAGTCAGAGA GCAAAACAAC CCACGCGTAC
TTTTAGACGT CGACGACGCC GTTGAGGAGG CTCAGTCTCT CGTTTTGTTG GGTGCGCATG 4210       4220       4230       4240       4250       4260
ACCAATGCCG CATTCACTTC TTCCGACGCA ACGTTACCCA TGGGCACTAC AGGGTCGTAC
TGGTTACGGC GTAAGTGAAG AAGGCTGCGT TGCAATGGGT ACCCGTGATG TCCCAGCATG
```

FIG._1E-1

```
4270       4280       4290       4300       4310       4320
ACTCCCCAC  AGGACGGCTC ATTTCCACCT CCGCCTCGGT GACGTAGGCT AAACCGAAAC
TGAGGGGTG  TCCTGCCGAG TAAAGGTGGA GGCGGAGCCA CTGCATCCGA TTTGGCTTTG
                                            └─UL139
4330       4340       4350       4360       4370       4380
CCACGTTGAA CCTAACGCGG TTTCGGAAGG CCTGAGACGT CACTTTCACA ATGACGTCCG
GGTGCAACTT GGATTGCGCC AAAGCCTTCC GGACTCTGCA GTGAAAGTGT TACTGCAGGC 4390       4400       4410       4420       4430       4440
TATACACGTT CATCATAAAA CACCCGTAGAG GCTAAGGCTT CGGTAGGGAG AGACCTCAAC
ATATGTGCAA GTAGTATTTT GTGGCATCTC CGATTCCGAA GCCATCCCTC TCTGGAGTTG 4450       4460       4470       4480       4490       4500
TGTTCCTGAT GAGCACCCGT GCTCTCATCT CTTCAGACTT GT ATGACCC CCGCTCAGAC
ACAAGGACTA CTCGTGGGCA CGAGAGTAGA GAAGTCTGAA CA TACTGGG GGCGAGTCTG
                                            └─UL140

4510       4520       4530       4540       4550       4560
TAACGCGACT ACCACCGTGC ACCCGCACGA CGCAAAAAAC GGCAGGCGCG GTAGTGCCCT
ATTGCGCTGA TGGTGGCACG TGGGCGTGCT GCGTTTTTTG CCGTCGCCGC CATCACGGGA 4570       4580       4590       4600       4610       4620
GCCGACCCTC GTCGTTTTCG GCTTTATCGT TACGCTACTT TTCTTTCTCT TTATGCTCTA
CGGCTGGGAG CAGCAAAAGC CGAAATAGCA ATGCGATGAA AAGAAAGAGA AATACGAGAT 4630       4640       4650       4660       4670       4680
CTTTTGGAAC AACGACGTGT TCCGTAAGCT GCTCCGTGCG CTTGGATCCA GCGCTGTTGC
GAAAACCTTG TTGCTGCACA AGGCATTCGA CGAGGCACGC GAACCTAGGT CGCGACAACG 4690       4700       4710       4720       4730       4740
GACCGCTTCG ACGCGTGGCA AGACGAGGTC ATCTACCGTC GTCCATCACG TCGTTCCCAG
CTGGCGAAGC TGCGCACCGT TCTGCTCCAG TAGATGGCAG CAGGTAGTGC AGCAAGGGTC
```

FIG._1E-2

```
       4750       4760       4770       4780       4790       4800
AGCGACGACG AGAGTCGTAC TAACAGCGTG TCATCGTACG TTCTTTTATC ACCCGCGTCC
TCGCTGCTGC TCTCAGCATG ATTGTCGCAC AGTAGCATGC AAGAAAATAG TGGGCGCAGG

4810  UL140   4830       4840       4850       4860
GATGGCGGTT TTGACAACCC GGCACTGACA GAGGCCGTCG ACAGCGTGGA CGACTGGGCG
CTACCGCCAA AACTGTTGGG CCGTGACTGT CTCCGGCAGC TGTCGCACCT GCTGACCCGC 4870       4880       4890       4900       4910       4920
ACCACCTCGG TTTTCTACGC CACGTCCGAC GAAACGGCGG ACGCCGAGCG CCGAGACTCG
TGGTGGAGCC AAAAGATGCG GTGCAGGCTG CTTTGCCGCC TGCGGCTCGC GGCTCTGAGC 4930       4940       4950       4960       4970       4980
CAGCAAACTGC TCATCGAGCT TCCGCCGGAG CCGCTCCCGC CCGACGTGGT GGCCGGCCATG
GTCGTTGACG AGTAGCTCGA AGGCGGCCTC GGCGAGGGCG GGCTGCACCA CCGCCGGTAC 4990       5000       5010       5020       5030       5040
CAGAAAAGCAG TGAAACGCGC TGTACAGAAC GCACTACGAC ACAGCCACGA CTCTTGGCAG
GTCTTTCGTC ACTTTGCGCG ACATGTCTTG CGTGATGCTG TGTCGGTGCT GAGAACCGTC 5050       5060       5070       5080       5090  5100 UL141
CTTCATCAGA CCCTGTGACG CCAGATGAAC GTTCCTTCTT AAACATCCGA GGTAGCAATG
GAAGTAGTCT GGGACACTGC GGTCTACTTG CAAGGAAGAA TTTGTAGGCT CCATCGTTAC 5110       5120       5130       5140       5150       5160
AGACAGGTCG CGTACCGCCG GCGACGCGAG AGTTCCTGCG CGGTGCTGGT CCACCACGTC
TCTGTCCAGC GCATGGCGGC CGCTGCGCTC TCAAGGACGC GCCACGACCA GGTGGTGCAG 5170       5180       5190       5200       5210       5220
GGCCGCGACG GCGACGGGCGA GGGGAGGCA GCAAAAAAGA CCTGCAAAAA AACCGGACGC
CCGGCGCTGC CGCTGCCGCT CCCCCTCCGT CGTTTTTTCT GGACGTTTTT TTGGCCTGCG
```

FIG.—1F-1

```
5230                5240                5250                5260                5270                5280
TCAGTTGCGG   GCATCCCGGG   CGAGAAGCTG   CGTCGCACGG   TGGTCACCAC   CACGCCGGCC
AGTCAACGCC   CGTAGGGCCC   GCTCTTCGAC   GCAGCGTGCC   ACCAGTGGTG   GTGCGGCCGG 5290                5300                5310                5320                5330                5340
CGACGTTTGA   GCGGCCGACA   CACGGAGCAG   GAGCAGGCGG   GCATGGCTCT   CTGTGAAAAA
GCTGCAAACT   CGCCGGCTGT   GTGCCTCGTC   CTCGTCCGCC   CGTACGCAGA   GACACTTTTT 5350                5360                5370                5380                5390                5400
GGGAAGAAAA   GAATCATCAT   GTGCCGCCGG   GAGTCGCTCC   GAACTCTGCC   GTGGCTGTTC
CCCTTCTTTT   CTTAGTAGTA   CACGGCGGCC   CTCAGCGAGG   CTTGAGACGG   CACCGACAAG 5410                5420                5430                5440                5450                5460
TGGGTGCTGT   TGAGCTCTGT   GCGACTCCTC   GAATATTCTT   CCTCTTCGTT   CCCCTTCGCC
ACCCACGACA   ACTCGAGACA   CGCTGAGGAG   CTTATAAGAA   GGAGAAGCAA   GGGGAAGCGG 5470                5480                5490                5500                5510                5520
ACCGCTGACA   TTGCCGAAAA   GATGTGGGCC   GAGAATTATG   AGACCACGTC   GCCGGCGCCG
TGGCGACTGT   AACGGCTTTT   CTACACCCGG   CTCTTAATAC   TCTGGTGCAG   CGGCCGCGGC 5530                5540                5550                5560                5570                5580
GTGTTGGTCG   CCGAGGGAGA   GCAAGTTACC   ATCCCCTGCA   CGGTCATGAC   ACACTCCTGG
CACAACCAGC   GGCTCCCTCT   CGTTCAATGG   TAGGGGACGT   GCCAGTACTG   TGTGAGGACC 5590                5600                5610                5620                5630                5640
CCCATGGTCT   CCATTCGCGC   ACGTTTCTGT   CGTTCCCACG   ACGGCAGCGA   CGAGCTCATC
GGGTACCAGA   GGTAAGCGCG   TGCAAAGACA   GCAAGGGTGC   TGCCGTCGCT   GCTCGAGTAG
```

FIG._1F-2

```
5650                5660       5670       5680       5690       5700
CTGGACGCCCG TCAAAGGCCA TCGGCTGATG AACGGACTCC AGTACCGCCT GCCGTACGCC
GACCTGCGGC AGTTTCCGGT AGCCGACTAC TTGCCTGAGG TCATGGCGGA CGGCATGCGG 5710                5720       5730       5740       5750       5760
ACTTGGAATT TCTCGCAATT GCATCTCGGC CAAATATTCT CGCTTACTTT TAACGTATCG
TGAACCTTAA AGAGCGTTAA CGTAGAGCCG GTTTATAAGA GCGAATGAAA ATTGCATAGC 5770                5780       5790       5800       5810       5820
ATGGACACAG CCGGCATGTA CGAATGCGTG CTACGCAACT ACAGCCACGG CCTCATCATG
TACCTGTGTC GGCCGTACAT GCTTACGCAC GATGCGTTGA TGTCGGTGCC GGAGTAGTAC 5830                5840       5850       5860       5870       5880
CAACGCTTCG TAATTCTCAC GCAGCTGGAG ACGCTCAGCC GGCCCGACGA ACCTTGCTGC
GTTGCGAAGC ATTAAGAGTG CGTCGACCTC TGCGAGTCGG CCGGGCTGCT TGGAACGACG 5890                5900       5910       5920       5930       5940
ACACCGGCGT TAGGTCGCTA CTCGCTGGGA GACCAGATCT GGTCGCCGAC GCCCTGGCGT
TGTGGCCGCA ATCCAGCGAT GAGCGACCCT CTGGTCTAGA CCAGCGGCTG CGGGACCGCA 5950                5960       5970       5980       5990       6000
CTACGGAATC ACGACTGCGG AACGTACCGC GGCTTTCAAC GCAACTACTT CTATATCGGC
GATGCCTTAG TGCTGACGCC TTGCATGGCG CCGAAAGTTG CGTTGATGAA GATATAGCCG 6010                6020       6030       6040       6050       6060
CGCGCCGACG CCGAGGATTG CTGGAAACCC GCATGTCCGG ACGAGGAACC CGACCGCTGT
GCGCGGCTGC GGCTCCTAAC GACCTTTGGG CGTACAGGCC TGCTCCTTGG GCTGGCGACA 6070                6080       6090       6100       6110       6120
TGGACAGTGA TACAGCGTTA CCGGCTCCCC GGCGACTGCT ACCGTTCGCA GCCACACCCG
ACCTGTCACT ATGTCGCAAT GGCCGAGGGG CCGCTGACGA TGGCAAGCGT CGGTGTGGGC
```

FIG._1G-1

```
       6130            6140            6150            6160            6170            6180
CCGAAATTTT  TACCGGTGAC  GCCAGCACCG  CCGGCCCGACA  TAGACACCGG  GATGTCTCCC
GGCTTTAAAA  ATGGCCACTG  CGGTCGTGGC  GGCCGGCTGT  ATCTGTGGCC  CTACAGAGGG 6190            6200            6210            6220            6230            6240
TGGGCCACTC  GGGGAATCGC  GGCGTTTTTG  GGGTTTTGGA  GTATTTTAC   CGTATGTTTC
ACCCGGTGAG  CCCCTTAGCG  CCGCAAAAAC  CCCAAAACCT  CATAAAAATG  GCATACAAAG 6250            6260            6270            6280            6290            6300
CTATGCTACC  TGTGTTATCT  GCAGTGTTGT  GGACGCTGGT  GTCCCACGCC  GGGAAGGGGA
GATACGATGG  ACACAATAGA  CGTCACAACA  CCTGCGACCA  CAGGGTGCGG  CCCTTCCCCT 6310            6320            6330            6340            6350            6360
CGACGAGGCG  GTGAGGGCTA  TCGACGCCTA  CCGACTTACG  ATAGTTACCC  CGGTGTTAGA
GCTGCTCCGC  CACTCCCGAT  AGCTGCGGAT  GGCTGAATGC  TATCAATGGG  GCCACAATCT

6370  UL141     6380            6390            6400            6410            6420
AAGATGAAGA  GGTGAGAACA  CGTATAAAAT  AAAAAAATAA  TATGTTAAAA  AATGCAGTGT
TTCTACTTCT  CCACTCTTGT  GCATATTTA   TTTTTTATT   ATACAATTTT  TTACGTCACA 6430            6440            6450  UL142  6460            6470            6480
GTGAAGTGTG  AATAGTGTGA  TTAAAAATATG  CGGATTGAAT  GGGTGTGGTG  GTTATTCGGA
CACTTCACAC  TTATCACACT  AATTTTATAC  GCCTAACTTA  CCCACACCAC  CAATAAGCCT 6490            6500            6510            6520            6530            6540
TACTTTGTGT  CATCCGTTGG  GAGCGAACGG  TCATTATCCT  ATCGTTACCA  CTTGGAATCT
ATGAAACACA  GTAGGCAACC  CTCGCTTGCC  AGTAATAGGA  TAGCAATGGT  GAACCTTAGA 6550            6560            6570            6580            6590            6600
AATTCATCTA  CCAACGTGGT  TTGCAACGGA  AACATTTCCG  TGTTTGTAAA  CGGCACCCTA
TTAAGTAGAT  GGTTGCACCA  AACGTTGCCT  TTGTAAAGGC  ACAAACATTT  GCCGTGGGAT
```

FIG. 1G-2

```
6610       6620       6630       6640       6650       6660
GGTGTGCGGT ATAACATTAC GGTAGGAATC AGTTCGTCTT TATTAATAGG ACACCTTACT
CCACACGCCA TATTGTAATG CCATCCTTAG TCAAGCAGAA ATAATTATCC TGTGGAATGA 6670       6680       6690       6700       6710       6720
ATACAAGTAT TGGAATCATG GTTCACACCC TGGGTCCAAA ATAAAAGTTA CAACAAACAA
TATGTTCATA ACCTTAGTAC CAAGTGTGGG ACCCAGGTTT TATTTTCAAT GTTGTTTGTT 6730       6740       6750       6760       6770       6780
CCCCTAGGTG ACACTGAAAC GCTTTATAAT ATAGATAGCG AAAACATTCA TCGCGTATCT
GGGGATCCAC TGTGACTTTG CGAAATATTA TATCTATCGC TTTTGTAAGT AGCGCATAGA 6790       6800       6810       6820       6830       6840
CAATATTTTC ACACAAGATG GATAAAATCT CTGCAAGAGA ATCACACTTG CGACCTCACA
GTTATAAAAG TGTGTTCTAC CTATTTTAGA GACGTTCTCT TAGTGTGAAC GCTGGAGTGT 6850       6860       6870       6880       6890       6900
AACAGTACAC CTACCTATAC ATATCAAGTA AACGTGAACA ACACGAATTA CCTAACACTA
TTGTCATGTG GATGGATATG TATAGTTCAT TTGCACTTGT TGTGCTTAAT GGATTGTGAT 6910       6920       6930       6940       6950       6960
ACATCCTCGG GATGGCAAGA CCGTCTAAAT TACACCGTCA TAAATAGTAC ACACTTAAC
TGTAGGAGCC CTACCGTTCT GGCAGATTTA ATGTGGCAGT ATTTATCATG TGTGAAATTG 6970       6980       6990       7000       7010       7020
CTCACAGAAT CGAACATAAC CAGCATTCAA AAATATCTCA ACACTACCTG CATAGAAAGA
GAGTGTCTTA GCTTGTATTG GTCGTAAGTT TTTATAGAGT TGTGATGGAC GTATCTTTCT 7030       7040       7050       7060       7070       7080
CTCCGTAACT ACACCCTTGGA GTCCGTATAC ACCACAACTG TGCCTCAAAA CATAACAACA
GAGTGTCTTA TGTGGAACCT CAGGCATATG TGGTGTTGAC ACGGAGTTTT GTATTGTTGT
```

FIG.\_1H-1

```
                                                     7090          7100          7110          7120          7130          7140
                                            TCTCAACACG    CAACAACCAC    TATGCACACA    ATACCTCCAA    ATACAATAAC    AATTCAAAAT
                                            AGAGTTGTGC    GTTGTTGGTG    ATACGTGTGT    TATGGAGGTT    TATGTTATTG    TTAAGTTTTA 7150          7160          7170          7180          7190          7200
ACAACTCAAA    GCCATACTGT    ACAGAGCGCCG   TCTTTTAACG    ACACACATAA    CGTGACGAAA
TGTTGAGTTT    CGGTATGACA    TGTCTCGCGGC   AGAAAATTGC    TGTGTGTATT    GCACTGCTTT 7210          7220          7230          7240          7250          7260
CACACGTTAA    ACATAAGCTA    CGTTTTATCA    CAAAAAACGA    ATAACACAAC    ATCACCGTGG
GTGTGCAATT    TGTATTCGAT    GCAAAATAGT    GTTTTTTGCT    TATTGTGTTG    TAGTGGCACC 7270          7280          7290          7300          7310          7320
ATATATGCCA    TACCTATGGG    CGCTACAGCC    ACAATAGGCG    CCGGTTTATA    TATCGGGAAA
TATATACGGT    ATGGATACCC    GCGATGTCGG    TGTTATCCGC    GGCCAAATAT    ATAGCCCTTT 7330          7340          7350    UL143  7360   UL142  7370          7380
CACTTTACGC    CGGTTAAGTT    CGTATACGAG    GTATGGCGCG    GTCAGTAAAG    ACGATTCGGA
GTGAAATGCG    GCCAATTCAA    GCATATGCTC    CATACCGCGC    CAGTCATTTC    TGCTAAGCCT 7390          7400          7410          7420          7430          7440
TTCAACACAT    ATACTCCCCA    CGATCCTCGA    ACACCTTACA    GCATATGAGC    AAAAAACAAG
AAGTTGTGTA    TATGAGGGGT    GCTAGGAGCT    TGTGGAATGT    CGTATACTCG    TTTTTTGTTC 7450          7460          7470          7480          7490          7500
AAAGTATAGC    CACAATCACA    TTTGGGCGAA    TAACATGCTG    TCATCCACTA    GCGTCTATTA
TTTCATATCG    GTGTTAGTGT    AAACCCGCTT    ATTGTACGAC    AGTAGGTGAT    CGCAGATAAT 7510          7520          7530          7540          7550          7560
ATCTAATGTT    TGTACTGTCA    CCGTTAAAAT    TAACGGGAGC    ATCCATGGGA    ATCAACGGGT
TAGATTACAA    ACATGACAGT    GGCAATTTTA    ATTGCCCTCG    TAGGTACCCT    TAGTTGCCCA
```

FIG.\_1H-2

```
             7570              7580              7590              7600              7610              7620
      CAACCAACGT        CCATCAGCTT        GTGATTGTGC        TCCATCTGGG        TAACCGCTGT        CAGCCCTTGGC
      GTTGGTTGCA        GGTAGTCGAA        CACTAACACG        AGGTAGACCC        ATTGGCGACA        GTCGGGAACCG

UL143        7630              7640              7650              7660              7670              7680
      GACAGGTGTA        ATCACAGCTG        TCACATAACT        CACGAAGCCT        CCAATCACAG        CAGCACACAT
      CTGTCCACAT        TAGTGTCGAC        AGTGTATTGA        GTGCTTCGGA        GGTTAGTGTC        GTCGTGTGTA 7690              7700              7710              7720              7730              7740
      AGTCCTAACG        CCATTGGCGT        GTATAAAAGT        TCGGAAAACT        TGACGGTTGT        ACGGCACGAC
      TCAGGATTGC        GGTAACCGCA        CATATTTTCA        AGCCTTTTGA        ACTGCCAACA        TGCCGTGCTG 7750              7760              7770              7780              7790              7800
      AAATCGATGT        AGTGGTATGT        TTTTCCAGCA        GAGACCGTGT        GCGGTCTCTT        AGGTTCGCTA
      TTTAGCTACA        TCACCATACA        AAAAGGTCGT        CTCTGGCACA        CGCCAGAGAA        TCCAAGCGAT 7810              7820              7830              7840              7850              7860
      TACTGTGGCT        GGAAACTGGT        TACCTGTGAA        GATGGCTAAC        TATCCTGTTC        TGTCCTGGAA
      ATGACACCGA        CCTTTGACCA        ATGGACACTT        CTACCGATTG        ATAGGACAAG        ACAGGACCTT 7870              7880              7890              7900              7910              7920
      AAACTTTTGG        CGTCGTAGGT        GGACTTTGCA        GTATGCGGGT        TAGTGAAGTT        ATGTCATTTA
      TTTGAAAACC        GCAGCATCCA        CCTGAAACGT        CATACGCCCA        ATCACTTCAA        TACAGTAAAT 7930              7940              7950              7960              7970              7980
      TTTACGTTTA        CGATCTCGTA        TTACAAACCG        CGGAGAGGAT        GATACCGTTC        GGCCCCATGA
      AAATGCAAAT        GCTAGAGCAT        AATGTTTGGC        GCCTCTCCTA        CTATGGCAAG        CCGGGGTACT 7990              8000        UL144  8010        8020              8030              8040
      GTTATTTTTA        TTCTTCCGGT        AGGAGGCATG        AAGCCCTCTGA        TAATGCTCAT        CTGCTTTGCT
      CAATAAAAAT        AAGAAGGCCA        TCCTCCGTAC        TTCGGAGACT        ATTACGAGTA        GACGAAACGA
```

*FIG._1I-1*

```
8050                 8060        8070        8080        8090        8100
GTGATATTAT  TGCAGCTTGG  AGTGACTAAA  GTGTGTCAGC  ATAATGAAGT  GCAACTGGGC
CACTATAATA  ACGTCGAACC  TCACTGATTT  CACACAGTCG  TATTACTTCA  CGTTGACCCG 8110                 8120        8130        8140        8150        8160
AATGAGTGCT  GCCCTCCGTG  TGGTTCGGGA  CAAAGAGTTA  CTAAAGTATG  CACGGATTAT
TTACTCACGA  CGGGAGGCAC  ACCAAGCCCT  GTTTCTCAAT  GATTTCATAC  GTGCCTAATA 8170                 8180        8190        8200        8210        8220
ACCAGTGTAA  CGTGTACCCC  TTGCCCCAAC  GGCACGTATG  TATCGGGACT  TTACAACTGT
TGGTCACATT  GCACATGGGG  AACGGGGTTG  CCGTGCATAC  ATAGCCCTGA  AATGTTGACA 8230                 8240        8250        8260        8270        8280
ACCGATTGCA  CTCAATGTAA  CGTCACTCAG  GTCATGATTC  GTAACTGCAC  TTCCACCAAT
TGGCTAACGT  GAGTTACATT  GCAGTGAGTC  CAGTACTAAG  CATTGACGTG  AAGGTGGTTA 8290                 8300        8310        8320        8330        8340
AATACCGTAT  GCGCACCTAA  GAACCATACG  TACTTTTCCA  CTCCAGGCGT  CCAACATCAC
TTATGGCATA  CGCGTGGATT  CTTGGTATGC  ATGAAAAGGT  GAGGTCCGCA  GGTTGTAGTG 8350                 8360        8370        8380        8390        8400
AAACAACGAC  AGCAAAATCA  TACCGCACAT  ATAACCGTCA  AACAAGGAAA  AAGCGGTCGT
TTTGTTGCTG  TCGTTTTAGT  ATGGCGTGTA  TATTGGCAGT  TTGTTCCTTT  TTCGCCAGCA 8410                 8420        8430        8440        8450        8460
CATACTCTAG  CCTGGTTGTC  TCTCTTTATC  TTTCTTGTGG  GTATCATACT  TTTAATTCTC
GTATGAGATC  GGACCAACAG  AGAGAAATAG  AAAGAACACC  CATAGTATGA  AAATTAAGAG 8470                 8480        8490        8500        8510        8520
TATCTTATAG  CCGCCTATCG  GAGTGAGAGA  TGCCAACAGT  GTTGCTCAAT  CGGCAAAATT
ATAGAATATC  GGCGGATAGC  CTCACTCTCT  ACGGTTGTCA  CAACGAGTTA  GCCGTTTTAA
```

FIG._11-2

```
       8530        UL144  8540        8550         8560         8570         8580
TTCTACCGCA   CCCTGTAAGC   TTCCTGTTGT   TGTTTTTACA   TCACGGTACG   ATGAAGTCAC
AAGATGGCGT   GGGACATTCG   AAGGACAACA   ACAAAAATGT   AGTGCCATGC   TACTTCAGTG 8590         8600         8610         8620         8630         8640
ACAGATAATT   ACAGATGAGC   TGTTCATATT   TTTTATTATT   TTTTCCAATT   CCTGCACTAA
TGTCTATTAA   TGTCTACTCG   ACAAGTATAA   AAAATAATAA   AAAAGGTTAA   GGACGTGATT 8650         8660         8670         8680         8690         8700
AAAAAGAAGC   ACTTTACGGA   ACCGTGTCTG   AGTATCTGTG   GGGAATTTAG   GTACTTTTTG
TTTTTCTTCG   TGAAATGCCT   TGGCACAGAC   TCATAGACAC   CCCTTAAATC   CATGAAAAAC 8710         8720         8730         8740         8750         8760
CCGACGTCAG   GAAAATAAG    TGTCGCCTAC   ATAAGAGCCC   GGTGCTATCG   TGCTGTCACT
GGCTGCAGTC   CTTTTATTC    ACAGCGGATG   TATTCTCGGG   CCACGATAGC   ACGACAGTGA 8770         8780         8790         8800         8810         8820
CTTTCTTGTT   GCCTTCGATG   TACGGGCGTC   TGGCTCATTA   CTACTCCTTC   ATCAGTAGCC
GAAAGAACAA   CGGAAGCTAC   ATGCCCGCAG   ACCGAGTAAT   GATGAGGAAG   TAGTCATCGG 8830         8840         8850         8860  UL145  8870         8880
CCAGCGTTAT   GGTTAATTTT   AAGCATCATA   ACGCCCGTGCA  GCTGTTATGT   GCACGGACCC
GGTCGCAATA   CCAATTAAAA   TTCGTAGTAT   TGCGGGCACGT  CGACAATACA   CGTGCCTGGG 8890         8900         8910         8920         8930         8940
GAGACGCACT   GCCGGATGGG   AACGTTTAAC   CCATCATGCG   TCGTATCACG   CGAACTACGG
CTCTGCGTGA   CGGCCTACCC   TTGCAAATTG   GGTAGTACGC   AGCATAGTGC   GCTTGATGCC 8950         8960         8970         8980         8990         9000
GGCATACGCC   GTGTTGATGG   CTACATCGCA   AAGAAAGTCC   CTAGTGTTAC   ATCGATACAG
CCGTATGCGG   CACAACTACC   GATGTAGCGT   TTCTTTCAGG   GATCACAATG   TAGCTATGTC
```

FIG._1J-1

```
9010              9020       9030       9040       9050       9060
TGCCGTGACA  GCCGTGGCCC TGCAGCTCAT GCCTGTTGAG ATCGTCCGCA AGCTAGATCA
ACGGCACTGT  CGGCACCGGG ACGTCGAGTA CGGACAACTC TAGCAGGCGT TCGATCTAGT 9070              9080       9090       9100       9110       9120
GTCGGACTGG  GTGCGGGGTG CCTGGATCGT GTCAGAGACT TTTCCAACTA GCGACCCCAA
CAGCCTGACC  CACGCCCCAC GGACCTAGCA CAGTCTCTGA AAAGGTTGAT CGCTGGGGTT 9130              9140       9150       9160  UL145 9170       9180
AGGAGTTTGG  AGCGACGATG ACTCCTCGAT GGGTGGAAGT GATGATTGAT GATGAGAACC
TCCTCAAACC  TCGCTGCTAC TGAGGAGCTA CCCACCTTCA CTACTAACTA CTACTCTTGG 9190              9200       9210       9220       9230       9240
TGACAAGAAA  GACGAGAGAG AAATTTAGAG CTGTCATTGT AGAATTAGTC TAGATTCCTG
ACTGTTCTTT  CTGCTCTCTC TTTAAATCTC GACAGTAACA TCTTAATCAG ATCTAAGGAC 9250              9260       9270       9280       9290       9300
ATAATAAACA  GTATCGATTT TGAAACCTAA TTGACGTGTG ATCGATTTTT AAACCTCTGT
TATTATTTGT  CATAGCTAAA ACTTTGGATT AACTGCACAC TAGCTAAAAA TTTGGAGACA 9310              9320       9330       9340       9350       9360
GTTGTGTGAT  TGATTGGTAT GTGGGGGGAT CCGATTTCAA AGGGGGGTAC TTATCGGGAA
CAACACACTA  ACTAACCATA CACCCCCCTA GGCTAAAGTT TCCCCCCATG AATAGCCCTT 9370              9380       9390       9400       9410       9420
TTGATGTGTC  ATGGACGCAG TTTTGAGCGA TTTTCCGGGA ATACCGGATA TTACGAATTA
AACTACACAG  TACCTGCGTC AAACTCGCT  AAAAGGCCCT TATGGCCTAT AATGCTTAAT
```

*FIG._1J-2*

```
         9430       9440       9450 UL146 9460       9470       9480
CTGGTAGTGA CGTAGATAAT AAAATTATAA TGCGATTAAT TTTTGGTGCG TTGATTATTT
GACCATCACT GCATCTATTA TTTTAATATT ACGCTAATTA AAAACCACGC AACTAATAAA 9490       9500       9510       9520       9530       9540
TTTTAGCATA TGTGTATCAT TATGAGGTGA ATGGAACAGA ATTACGCTGC AGATGTCTTC
AAAATCGTAT ACACATAGTA ATACTCCACT TACCTTGTCT TAATGCGACG TCTACAGAAG 9550       9560       9570       9580       9590       9600
ATAGAAAATG GCCGCCTAAT AAAATTATAT TGGGTAATTA TTGGCTTCAT CGCGATCCCA
TATCTTTTAC CGGCGGATTA TTTTAATATA ACCCATTAAT AACCGAAGTA GCGCTAGGGT 9610       9620       9630       9640       9650       9660
GAGGGCCCGG ATGCGATAAA AATGAACATT TATTGTATCC AGACGGAAGG AAACCGCCTG
CTCCCGGGCC TACGCTATTT TTACTTGTAA ATAACATAGG TCTGCCTTCC TTTGGCGGAC 9670       9680       9690       9700       9710       9720
GACCTGGAGT ATGTTTATCG CCCGATCACC TCTTCTCAAA ATGGTTAGAC AAACACAACG
CTGGACCTCA TACAAATAGC GGGCTAGTGG AGAAGAGTTT TACCAATCTG TTTGTGTTGC 9730       9740       9750       9760       9770       9780
ATAATAGGTG GTATAAATGT AACATAACGA AATCACCAGG ACCGAGACGA ATAAATATAA
TATTATCCAC CATATTTACA TTGTATTGCT TTAGTGGTCC TGGCTCTGCT TATTTATATT 9790       9800 UL146 9810       9820       9830       9840
CCTTGATAGG TGTTAGAGGA TAA TATTTAA TGTATGTTTT CAAACAGACA AGTTCGTTAA
GGAACTATCC ACAATCTCCT ATT ATAAATT ACATACAAAA GTTTGTCTGT TCAAGCAATT 9850       9860    9870 UL147 9880       9890       9900
AACAAAATAT TACAGTATGT GTTTAAT ATG GTGCTAACAT GGTTGCACCA TCCGGTTTCA
TTGTTTTATA ATGTCATACA CAAATTA TAC CACGATTGTA CCAACGTGGT AGGCCAAAGT
```

FIG._1K-1

```
9910       9920       9930       9940       9950       9960
AACTCGCATA TCAATCTGTT ATCGGTACGA CACCTGTCAT TAATCGCATA TATGTTACTT
TTGAGCGTAT AGTTAGACAA TAGCCATGCT GTGGACAGTA ATTAGCGTAT ATACAATGAA 9970       9980       9990       10000      10010      10020
ACCATATGTC CCCTAGCCCGT CCATGTTTTA GAACTAGAAG ATTACGACAG GCGCTGCCGT
TGGTATACAG GGGATCGGCA GGTACAAAAT CTTGATCTTC TAATGCTGTC CGCGACGGCA 10030      10040      10050      10060      10070      10080
TGCAACAACC AAATTCTGTT GAATACCCTG CCGGTCGGAA CCGAATTGCT TAAGCCAATC
ACGTTGTTGG TTTAAGACAA CTTATGGGAC GGCCAGCCTT GGCTTAACGA ATTCGGTTAG 10090      10100      10110      10120      10130      10140
GCAGCGAGCG AAAGCTGCAA TCGTCAGGAA GTGCTGGCTA TTTTAAAGGA CAAGGAACC
CGTCGCTCGC TTTCGACGTT AGCAGTCCTT CACGACCGAT AAAATTTCCT GTTCCCTTGG 10150      10160      10170      10180      10190      10200
AAGTGTCTCA ATCCTAACGC GCAAGCCGTG CGTCGTCACA CGTCGCGGCT ATTTTTTCGG
TTCACAGAGT TAGGATTGCG CGTTCGGCAC GCAGCAGTGT GCAGCGCCGA TAAAAAAGCC 10210      10220      10230      10240      10250      10260
TTAATCTTAG ACGAGGAACA ACGCATTTAC GACGTAGTGT CTACCAATAT TGAGTTCGGT
AATTAGAATC TGCTCCTTGT TGCGTAAATG CTGCATCACA GATGGTTATA ACTCAAGCCA 10270      10280      10290      10300      10310      10320
GCCTGGCCAG TCCCTACGGC CTACAAAGCC TTTCTTTGGA AATACGCCAA GAGACTGAAC
CGGACCGGTC AGGGATGCCG GATGTTTCGG AAAGAAACCT TTATGCGGTT CTCTGACTTG

10330      UL147 10350 10360      10370      10380
TACCACCACT TCAGACTGCG CTGGTGATCA TGTCCCTATT TTACCGTGCG GTAGCTCTGG
ATGGTGGTGA AGTCTGACGC GACCACTAGT ACAGGGATAA AATGGCACGC CATCGAGACC
```

*FIG._1K-2*

```
10390       10400       10410       10420       10430       10440
GCACGCTAAG  CGCTTTGGTG  TGGTACAGCA  CTAGCATCCT  CGCAGAGATT  AACGAAAATT
CGTGCGATTC  GCGAAACCAC  ACCATGTCGT  GATCGTAGGA  GCGTCTCTAA  TTGCTTTTAA 10450       10460       10470       10480       10490       10500
CCTGCTCCTC  ATCTTCTGCG  GATCACGAAG  ACTGCGAGGA  ACCGGACGAAG  ATCGTTCGCG
GGACGAGGAG  TAGAAGACGC  CTAGTGCTTC  TGACGCTCCT  TGGCCTGCTC  TAGCAAGCGC 10510       10520       10530       10540       10550       10560
AAGAGCAAGA  CTATCGGGCT  CTGCTGGCCT  TTTCCCTAGT  GATTTGCGGT  ACGCTCCTCG
TTCTCGTTCT  GATAGCCCGA  GACGACCGGA  AAAGGGATCA  CTAAACGCCA  TGCGAGGAGC 10570       10580       10590       10600       10610       10620
TCACTTGTGT  GATCTGAGAC  GTCATGCTGG  TAGCGTTTAT  GAGTCGGGCG  GTGGCCGACA
AGTGAACACA  CTAGACTCTG  CAGTACGACC  ATCGCAAATA  CTCAGCCCGC  CACCGGCTGT 10630       10640       10650 UL148 10660       10670       10680
CGCCGCATTT  CCTAACCCGC  GCAAGCATGTT  GCGCTTGCTG  TTCACGCTCG  TCCTGCTGGC
GCGGCGTAAA  GGATTGGGCG  CGTCGTACAA  CGCGAACGAC  AAGTGCGAGC  AGGACGACCG 10690       10700       10710       10720       10730       10740
CCTCCACGGG  CAGTCTGTCG  GCGCTAGCCG  CGACTATGTG  CATGTTCGGC  TACTGAGCTA
GGAGGTGCCC  GTCAGACAGC  CGCGATCGGC  GCTGATACAC  GTACAAGCCG  ATGACTCGAT 10750       10760       10770       10780       10790       10800
CCGAGGCGAC  CCCCTGGTCT  TCAAGCACAC  TTTCTCGGGT  GTGCGTCGAC  CCTTCACCGA
GGCTCCGCTG  GGGGACCAGA  AGTTCGTGTG  AAAGAGCCCA  CACGCAGCTG  GGAAGTGGCT 10810       10820       10830       10840       10850       10860
GCTAGGCTGG  GCTGCGTGTC  GCGACTGGGA  CAGTATGCAT  TGCACACCCT  TCTGGTCTAC
CGATCCGACC  CGACGCACAG  CGCTGACCCT  GTCATACGTA  ACGTGTGGGA  AGACCAGATG
```

FIG._1L-1

```
10870      10880      10890      10900      10910      10920
CGATCTGGAG CAGATGACCG ACTCGGTGCG GCGTTACAGC ACGGTGAGCC CCGGCAAGGA
GCTAGACCTC GTCTACTGGC TGAGCCACGC CGCAATGTCG TGCCACTCGG GGCCGTTCCT 10930      10940      10950      10960      10970      10980
AGTGACGCTT CAGCTTCACG GGAACCAAAC CGTACAGCCG TCGTTCTAA GCTTTACGTG
TCACTGCGAA GTCGAAGTGC CCTTGGTTTG GCATGTCGGC AGCAAAGATT CGAAATGCAC 10990      11000      11010      11020      11030      11040
CCGCCTGCAG CTAGAACCCG TGGTGAAAA TGTTGGCCTC TACGTGGCCT ACGTGGTCAA
GGCGGACGTT GATCTTGGGC ACCACCTTTT ACAACCGGAG ATGCACCGGA TGCACCAGTT 11050      11060      11070      11080      11090      11100
CGACGGGCGAA CGCCCACAAC AGTTTTTAC ACCGCAGGTA GACGTGGTAC GCTTTGCTCT
GCTGCCGCTT GCGGGTGTTG TCAAAAAATG TGGCGTCCAT CTGCACCATG CGAAACGAGA 11110      11120      11130      11140      11150      11160
ATATCTAGAA ACACTCTCCC GGATCGTGAA ACCGTTAGAA TCAGGTCGCC TGGCAGTGGA
TATAGATCTT TGTGAGAGGG CCTAGCACCT TGGCAATCTT AGTCCAGCGG ACCGTCACCT 11170      11180      11190      11200      11210      11220
ATTTGATACG CCTGACCTAG CTCTGCGCC CGATTTAGTA AGCAGCCTCT TCGTGGCCGG
TAAACTATGC GGACTGGATC GAGACCGCGG GCTAAATCAT TCGTCGGAGA AGCACCGGCC 11230      11240      11250      11260      11270      11280
ACACGGCGAG ACATGAACTTT ACATGAACTG CGCAGTCAGA CCCACTACCT
TGTGCCGCTC TGGCTGAAAA TGTACTTGAC CTGCGACGCA GGTCAGTCT GGGTGATGGA 11290      11300      11310      11320      11330      11340
GGAGGAGATG GCCTTACAGG TGGAGATTCT AAAACCCCGC GGCGTACGTC ACCGCGCTAT
CCTCCTCTAC CGGAATGTCC ACCTCTAAGA TTTGGGGCG CCGCATGCAG TGGCGCGATA
```

FIG._1L-2

```
                11360        11370        11380        11390        11400
      TATCCACCAT CCGAAGCTAC AGCCGGGCGT TGGCCTGTGG ATAGATTTCT GGCGTGTACCG
      ATAGGTGGTA GGCTTCGATG TCGGCCCGCA ACCGGACACC TATCTAAAGA CGCACATGGC 11410        11420        11430        11440        11450        11460
      CTACAACGCG CGCCTGACCC GCGGCTACGT ACGATACACC CTGTCACCGA AAGCGCGCTT
      GATGTTGCGC GCGGACTGGG CGCCGATGCA TGCTATGTGG GACAGTGGCT TTCGCGCGAA 11470        11480        11490        11500        11510        11520
      GCCCGCAAAA GCAGAGGGTT GGCTGGTGTC ACTAGACAGA TTCATCGTGC AGTACCTCAA
      CGGGCGTTTT CGTCTCCCAA CCGACCACAG TGATCTGTCT AAGTAGCACG TCATGGAGTT 11530        11540        11550        11560        11570        11580
      CACATTGCTG ATTACAATGA TGGGCGGCGAT ATGGGCTCGC GTTTTGATAA CCTACCTGT
      GTGTAACGAC TAATGTTACT ACCGCCGCTA TACCCGAGCG CAAAACTATT GGATGGACCA 11590        11600        11610        11620        11630        11640
      UL148 CGGTAGAGGC TTGCGGAAAC CACGTCCTCG TCACACGTCG TTCGCGGACA
      GTCGCGGCGT                                                   
      CAGCGCCGCA GCCATCTCCG AACGCCTTTG GTGCAGGAGC AGTGCGCAGC AAGCGCCTGT 11650        11660        11670        11680        11690        11700
      TAGCAAGAAA TCCACGTCGC CACATCTCGA UL132 GAATGCCGGC CTTGCGGGGT CCCCTTCGCG
      ATCGTTCTTT AGGTGCAGCG GTGTAGAGCT      CTTACGGCCG GAACGCCCCA GGGGAAGCGC 11710        11720        11730        11740        11750        11760
      CAACATTCCT GGCCCTGGTC GCGTTCGGGT TGCTGCTTCA GATAGACCTC AGCGACGCTA
      GTTGTAAGGA CCGGGACCAG CGCAAGCCCA ACGACGAAGT CTATCTGGAG TCGCTGCGAT 11770        11780        11790        11800        11810        11820
      CGAATGTGAC CAGCAGCACA AAAGTCCCTA CTAGCACCAG CAACAGAAAT AACGTCGACA
      GCTTACACTG GTCGTCGTGT TTTCAGGGAT GATCGTGGTC GTTGTCTTTA TTGCAGCTGT
```

FIG._1M-1

```
11830      11840      11850      11860      11870      11880
ACGCCACGAG TAGCGGACCC ACAACCGGGA TCAACATGAC CACCACCCAC GAGTCTTCCG
TGCGGGTGCTC ATCGCCTGGG TGTTGGCCCT AGTTGTACTG GTGGTGGGTG CTCAGAAGGC 11890      11900      11910      11920      11930      11940
TTCACAACGT GCGCAATAAC GAGATCATGA AAGTGCTGGC TATCCTCTTC TACATCGTGA
AAGTGTTGCA CGCGTTATTG CTCTAGTACT TTCACGACCG ATAGGAGAAG ATGTAGCACT 11950      11960      11970      11980      11990      12000
CAGGCACCTC CATTTTCAGC TTCATAGCGG TACTGATCGC GGTAGTTTAC TCCTCGTGTT
GTCCGTGGAG GTAAAAGTCG AAGTATCGCC ATGACTAGCG CCATCAAATG AGGAGCACAA 12010      12020      12030      12040      12050      12060
GCAAGCACCC GGGCCGCTTT CGTTTCGCCG ACGAAGAGGC CGTCAACCTG TTGGACGACA
CGTTCGTGGG CCCGGCGAAA GCAAAGCGGC TGCTTCTCCG GCAGTTGGAC AACCTGCTGT 12070      12080      12090      12100      12110      12120
CGGACGACAG TGGCGGCAGC AGCCCGTTTG GCAGCGGTTC CCGACGAGGT TCTCAGATCC
GCCTGCTGTC ACCGCGCCGG TCGGGCAAAC CGTCGCCAAG GGCTGCTCCA AGAGTCTAGG 12130      12140      12150      12160      12170      12180
CCGGCCGGATT TTGTTCCTCG AGCCCTTATC AGCGGTTGGA AACTCGGGAC TGGGACGAGG
GGCGGCCTAA AACAAGGAGC TCGGGAATAG TCGCCAACCT TTGAGCCCTG ACCCTGCTCC 12190      12200      12210      12220      12230      12240
AGGAGGAGGC GTCCGCGGCC CGGCAGCGCA TGAAACATGA TCCTGAGAAC GTCATCTATT
TCCTCCTCCG CAGGCGCCGG GCGCTCGCGT ACTTTGTACT AGGACTCTTG CAGTAGATAA 12250      12260      12270      12280      12290      12300
TCAGAAAGGA TGGCAACTTG GACACGTCGT TCGTGAATCC CAATTATGGG AGAGGCTCGC
AGTCTTTCCT ACCGTTGAAC CTGTGCAGCA AGCACTTAGG GTTAATACCC TCTCCGAGCG
```

FIG._1M-2

```
         12310      12320      12330      12340      12350      12360
    CTTTGACCAT CGAATCTCAC CTCTCGGACA ATGAGGAGGA CCCCATCAGG TACTACGTTT
    GAAACTGGTA GCTTAGAGTG GAGAGCCTGT TACTCCTCCT GGGTAGTCC  ATGATGCAAA 12370      12380      12390      12400      12410      12420
    CGGTGTACGA TGAACTGACC GCCTCGGAAA TGGAAGAACC TTCGAACAGC ACCAGCTGGC
    GCCACATGCT ACTTGACTGG CGGAGCCTTT ACCTTCTTGG AAGCTTGTCG TGGTCGACCG 12430      12440      12450      12460      12470      12480
    AGATTCCCAA ACTAATGAAA GTTGCCATGC AACCCGTCTC GCTCAGAGAT CCCGAGTACG
    TCTAAGGGTT TGATTACTTT CAACGGTACG TTGGGCAGAG CGAGTCTCTA GGGCTCATGC

UL132    12490      12500      12510      12520      12530      12540
    ACTAGCTTT TTTTTTTGTC TTTCGGTTCC AACTCTTTCC CCGCCCATC ACCTGCCTG
    TGATCGAAA AAAAAAACAG AAAGCCAAGG TTGAGAAAGG GGCGGGTAG TGGAGCGGAC 12550      12560      12570      12580      12590      12600
    TACTATGTGT ATGATGTCTC ATAATAAAGC TTTCTTTCTC AGTCTGCAAC ATGCAGCTGT
    ATGATACACA TACTACAGAG TATTATTTCG AAAGAAAGAG TCAGACGTTG TACGTCGACA 12610      12620      12630      12640      12650      12660
    GTCGGGTGTG GCTGTCTGTT TGTCTGTGCG CCGTGGTGCT GGGTCAGTGC CAGCGGGAAA
    CAGCCCACAC CGACAGACAA ACAGACACGC GGCACCACGA CCCAGTCACG GTCGCCCTTT 12670      12680      12690      12700      12710      12720
    CCGCGGAAAA AAACGATTAT TACCGAGTAC CGCATTACTG GGACGGCGTG TCTCGCGCGC
    GGCGCCTTTT TTTGCTAATA ATGGCTCATG GCGTAATGAC CCTGCCACG AGAGCGCGCG 12730      12740      12750      12760      12770      12780
    TGCCCGACCA AACCCGTTAC AAGTATGTGG AACAGCTCGT GGACCTCACG TTGAACTACC
    ACGGGCTGGT TTGGGCAATG TTCATACACC TTGTCGAGCA CCTGGAGTGC AACTTGATGG
```

FIG. 1N-1

```
       12790         12800         12810         12820         12830         12840
ACTACGATGC    GAGCCACGGC    TTGGACAACT    TTGACGTGCT    CAAGAGGTGA    GGGTACGCGC
TGATGCTACG    CTCGGTGCCG                  AACTGCACGA    GTTCTCCACT    CCCATGCGCG 12850         12860         12870         12880         12890         12900
TAAAGGTGCA    TGACAACGGG    AAGGTAAGGG    CGAACGGGTA    ACGGCTAAGT    AACCGCATGG
ATTTCCACGT    ACTGTTGCCC    TTCCATTCCC    GCTTGCCCAT    TGCCGATTCA    TTGGCGTACC 12910         12920         12930         12940         12950         12960
GGTATGAAAT    GACGTTTGGA    ACCTGTGCTT    GCAGAATCAA    CGTGACCGAG    GTGTCGTTGC
CCATACTTTA    CTGCAAACCT    TGGACACGAA    CGTCTTAGTT    GCACTGGCTC    CACAGCAACG 12970         12980         12990         13000         13010         13020
TCATCAGCGA    CTTTAGACGT    CAGAACCGTC    GCGGCGGCAC    CAACAAAAGG    ACCACGTTCA
AGTAGTCGCT    GAAATCTGCA    GTCTTGGCAG    CGCCGCCGTG    GTTGTTTTCC    TGGTGCAAGT 13030         13040         13050         13060         13070         13080
ACGCCCGCGG    TTCGCTGGCG    CCACACGCCC    GGAGCCTCGA    GTTCAGCGTG    CGGCTCTTTG
TGCGGGCGCC    AAGCGACCGC    GGTGTGCGGG    CCTCGGAGCT    CAAGTCGCAC    GCCGAGAAAC 13090         13100    13110 UL130  13120         13130         13140
CCAACTAGCC    TGCGTCACGG    GAAATAATAT    GCTGCGGCTT    CTGCTTCGTC    ACCACTTTCA
GGTTGATCGG    ACGCAGTGCC    CTTTATTATA    CGACGCCGAA    GACGAAGCAG    TGGTGAAAGT 13150         13160         13170         13180         13190         13200
CTGCCTGCTT    CTGTGCGCGG    TTTGGGCAAC    GCCCTGTCTG    GCGTCTCCGT    GGTCGACGCT
GACGGACGAA    GACACGCGCC    AAACCCGTTG    CGGGACAGAC    CGCAGAGGCA    CCAGCTGCGA
```

FIG._1N-2

```
           13210      13220      13230      13240      13250      13260
      AACGGCAAAC CAGAATCCGT CCCCGCCATG GTCTAAACTG ACGTATTCCA AACCGCATGA
      TTGCCGTTTG GTCTTAGGCA GGGGCGGTAC CAGATTTGAC TGCATAAGGT TTGGCGTACT 13270      13280      13290      13300      13310      13320
      CGCGGCGACG TTTTACTGTC CTTTCTCTA  TCCCTCGCCC CCACGGTCCC CCTGCAATT
      GCGCCGCTGC AAAATGACAG GAAAAGAGAT AGGGAGCGGG GGTGCCAGGG GGAACGTTAA 13330      13340      13350      13360      13370      13380
      CTCGGGGTTC CAGCAGGTAT CAACGGGTCC CGAGTGTCGC AACGAGACCC TGTATCTGCT
      GAGCCCCAAG GTCGTCCATA GTTGCCCAGG GCTCACAGCG TTGCTCTGGG ACATAGACGA 13390      13400      13410      13420      13430      13440
      GTACAACCGG GAAGGCCAGA CCTTGGTGGA GAGAAGCTCC ACCTGGGTGA AAAAGGTGAT
      CATGTTGGCC CTTCCGGTCT GGAACCACCT CTCTTCGAGG TGGACCCACT TTTTCCACTA 13450      13460      13470      13480      13490      13500
      CTGGTATCTG AGCGGTCGCA ACCAGACCAT CCTCCAACGG ATGCCCCAAA CGGCTTCGAA
      GACCATAGAC TCGCCAGCGT TGGTCTGGTA GGAGGTTGCC TACGGGGTTT GCCGAAGCTT 13510      13520      13530      13540      13550      13560
      ACCGAGCGAC GGAAACGTGC AGATCAGCGT GGAAGACGCC CGTCGTCAAC GATGGCACAT
      TGGCTCGCTG CCTTTGCACG TCTAGTCGCA CCTTCTGCGG GCAGCAGTTG CTACCGTGCG 13570      13580      13590      13600      13610      13620
      GGTGCCCAAG CAGACCAAGC TGCTACGCTT CGTCGTCAAC GATGGCACGC GTTATCAGAT
      CCACGGGTTC GTCTGGTTCG ACGATGCGAA GCAGCAGTTG CTACCGTGCG CAATAGTCTA 13630      13640      13650      13660      13670      13680
      GTGTGTGATG AAGCTGGAGA GCTGGGCCCA CGTCTTCCGG GACTACAGCG TGTCTTTTCA
      CACACACTAC TTCGACCTCT CGACCCGGGT GCAGAAGGCC CTGATGTCGC ACAGAAAAGT
```

*FIG._10-1*

```
       13690          13700          13710          13720          13730          13740
GGTGCGATTG     ACGTTCACCG     AGGCCAATAA     CCAGACTTAC     ACCTTCTGTA     CCCATCCCAA
CCACGCTAAC     TGCAAGTGGC     TCCGGTTATT     GGTCTGAATG     TGGAAGACAT     GGGTAGGGTT

13750 UL130  13760    13770          13780          13790          13800
TCTCATCATT     TGAGCCCGTC     GCGGCGCGCAG    GGAATTTTGA     AAACCGGCGCG    TCATGAGTCC
AGAGTAGTAA     ACTCGGGCAG     CGCGCGCGTC     CCTTAAAACT     TTTGGCGCGC     AGTACTCAGG 13810          13820          13830          13840          13850          13860
CAAAGACCTG     ACGCCGTTCT     TGACGACGTT     GTGGCTGCTA     TTGGGTCACA     GCCGCGTGCC
GTTTCTGGAC     TGCGGCAAGA     ACTGCTGCAA     CACCGACGAT     AACCCAGTGT     CGGCGCACGG 13870          13880          13890          13900          13910          13920
GCGGGTGCGC     GCAGAAGAAT     GTTGCGAATT     CATAAACGTC     AACCACCCGC     CGGAACGCTG
CGCCCACGCG     CGTCTTCTTA     CAACGCTTAA     GTATTTGCAG     TTGGTGGGCG     GCCTTGCGAC 13930          13940          13950          13960          13970          13980
TTACGATTTC     AAAATGTGCA     ATCGCTTCAC     CGTCGCGTAC     GTATTTTCAT     GATTGTCTGC
AATGCTAAAG     TTTTACACGT     TAGCGAAGTG     GCAGCGCATG     CATAAAAGTA     CTAACAGACG 13990          14000          14010          14020          14030          14040
GTTCTGTGGT     GCGTCTGGAT     TTGTCTCTCG     ACGTTTCTGA     TAGCCATGTT     CCATCGACGA
CAAGACACCA     CGCAGACCTA     AACAGAGAGC     TGCAAAGACT     ATCGGTACAA     GGTAGCTGCT 14050          14060          14070          14080          14090          14100
TCCTCGGGAA     TGCCAGAGTA     GATTTCATG      AATCCACAGG     CTGCGGTGTC     CGGACGGCGA
AGGAGCCCTT     ACGGTCTCAT     CTAAAAGTAC     TTAGGTGTCC     GACGCCACAG     GCCTGCCGCT 14110          14120          14130          14140          14150          14160
AGTCTGCTAC     AGTCCCGAGA     AAACGGCTGA     GATTCGCGGG     ATCGTCACCA     CCATGACCCA
TCAGACGATG     TCAGGGCTCT     TTTGCCGACT     CTAAGCGCCC     TAGCAGTGGT     GGTACTGGGT
```

FIG._10-2

```
        14170      14180      14190      14200      14210      14220
TTCATTGACA CGCCAGGTCG TACACAACAA ACTGACGAGC TGCAACTACA ATCCGTAAGT
AAGTAACTGT GCGGTCCAGC ATGTGTTGTT TGACTGCTCG ACGTTGATGT TAGGCATTCA 14230      14240      14250      14260      14270      14280
CTCTTCCTCG AGGGCCTTAC AGCCTATGGG AGAGTAAGAC AGAGAGGGAC AAAACATCAT
GAGAAGGAGC TCCCGGAATG TCGGATACCC TCTCATTCTG TCTCTCCCTG TTTTGTAGTA 14290      14300      14310      14320      14330      14340
TAAAAAAAAA AGTCTAATTT CACGTTTTGT ACCCCCCTTC CCCTCCGTGT TGTAGCCCAT
ATTTTTTTTT TCAGATTAAA GTGCAAAACA TGGGGGAAG GGGAGGCACA ACATCGGGTA 14350      14360      14370      14380      14390      14400
CGGCCGCGGC GATCTCCTAG TAACACTCGT CCGACACTTC CACCATCTCC AGCTCGGCCG
GCCGGCGCCG CTAGAGGATC ATTGTGAGCA GGCTGTGAAG GTGGTAGAGG TCGAGCCGGC 14410      14420      14430      14440      14450      14460
GCGGTTCGGC ATCCTCTACC AGCGGCGTCG TCTCATCTTT GCCGCAGCAG CGGACGCACA
CGCCAAGCCG TAGGAGATGG TCGCCGCAGC AGAGTAGAAA CGGCGTCGTC GCCTGCGTGT 14470      14480      14490      14500      14510      14520
CCTTCTCCAG GCAGAACGCC ACCAGCTGCC GCCGAACGTA CCACAGGTAC ACGTGCAGAC
GGAAGAGGTC CGTCTTGCGG TGGTCGACGG CGGCTTGCAT GGTGTCCATG TGCACGTCTG 14530      14540      14550      14560      14570      14580
CTGCGAACAG GACTACGGAG GTCATGACCA GCCGAACGCA CACGGGAATC CAGGGATCGA
GACGCTTGTC CTGATGCCTC CAGTACTGGT CGGCTTGCGT GTGCCCTTAG GTCCCTAGCT 14590      14600      14610      14620      14630      14640
GATTGTTGCT GGAACTCATG GCTATCGCCA CCGACGTGCC CCGTCTGTC TCACCGCCGC
CTAACAACGA CCTTGAGTAC CGATAGCGGT GGCTGCACGG GCGCAGACAG AGTGGGGCG
```

FIG._1P-1

```
14650       14660       14670       14680       14690       14700
TCGCCCGATG  TCGCGCGGCT  TGTTATACGC  TAGCCCGTCG  CCGCCTCGGG  GCACGGTGCC
AGCCGGGCTAC AGCGCGCCGA  ACAATATGCG  ATCGGGCAGC  GGCGGAGCCC  CGTGCCACGG 14710       14720       14730       14740       14750       14760
CTCCTACCCA  CGTAACTTCC  TCCCGTGACTT  AAAGTCGCGT  GTGGTAGATC  TCCTGCTCCG
GAGGATGGGT  GCATTGAAGG  AGGCACTGAA  TTTCAGCGCA  CACCATCTAG  AGGACGAGGC 14770       14780       14790       14800       14810       14820
TGGACGAACC  GTCCGGCAGG  ATAGCGGTTA  AGGATTCGGT  GCTAAGGCCG  TGTCGCCAAC
ACCTGCTTGG  CAGGCCGTCC  TATCGCCAAT  TCCTAAGCCA  CGATTCCGGC  ACAGCGGTTG 14830       14840       14850       14860       14870       14880
GTCGAATGCT  ACGTTGCAAC  AGCTTCGACG  GACGGCCATC  CCCTCTCTCA  TCGCAATAAT
CAGCTTACGA  TGCAACGTTG  TCGAAGCTTG  CTGCCGGTAG  GGGAGAGAGT  AGCGTTATTA 14890       14900       14910       14920       14930       14940
AAAACACCAG  CAGCCGCGCAC  GACGCGATCA  CGGTGACACC  CATGATTAGA  CCCACGCAGA
TTTGTGGTC   GTCGCGGGTG  CTGCGCTAGT  GCCACTGTGG  GTACTAATCT  GGGTGCGTCT 14950       14960       14970       14980       14990       15000
TAGCCAGCCC  CGCTAGCGTA  TCTAGCGCCA  TCCCGTTCGC  TCCCGTTGTC  TCCTGAGCGA
ATCGGTCGGG  GCGATCGCAT  AGATCGCGGT  AGGGCAAGCG  AGGGCAACAG  AGGACTCGCT 15010       15020       15030       15040       15050       15060
AGCAACTTCT  CGGTCCCCGT  TTTCAACAGT  TTTGTTTCC   TTCTCCGCGA  CTAGATGTTA
TCGTTGAAGA  GCCAGGGCA   AAAGTTGTCA  AAAACAAAGG  AAGAGGCGCT  GATCTACAAT 15070       15080       15090       15100       15110       15120
ACGCCCGGCG  TCTTTCCGGC  CGTGCTCTAC  CTCCTGGCGC  TTGTCGTCTG  GGTTGAGATG
TGCGGGCGCC  AGAAAGGCCG  GCACGAGATG  GAGGACCGCG  AACAGCAGAC  CCAACTCTAC
```

*FIG._1P-2*

```
15130                15140       15150       15160       15170       15180
TTCTGCCTCG   TCGCCGTAGC  CGTCGTCGAG  CGGCGAGATCG  CCTGGGCGCT  GCTGCTGCGG
AAGACGGAGC   AGCGGCATCG  GCAGCAGCTC  GCGCTCTAGC   GGACCCGCGA  CGACGACGCC 15190                15200       15210       15220       15230       15240
ATGCTGGTCG   TTGGCCTGAT  GGTGGAAGTC  CCGCCGCCG    CCGCTTGGAC  CTTCGTGCGT
TACGACCAGC   AACCGGACTA  CCACCTTCAG  GGCGGCGGC    GGCGAACCTG  GAAGCACGCA 15250                15260       15270       15280       15290       15300
TGTCTTGCCT   ATCAGCGCTC  CTTCCCCGTG  CTTACGGCCT   TCCCCTGAAA  CCCACGTTAA
ACAGAACGGA   TAGTCGCGAG  GAAGGGGCAC  GAATGCCGGA   AGGGGACTTT  GGGTGCAATT 15310                15320       15330       15340       15350       15360
CCGACCGTCC   CAAAAACGCC  GGTGTTAACA  CAGGAAAAAA   AGAAACCACG  CAGGAACCGC
GGCTGGCAGG   GTTTTTGCGG  CCACAATTGT  GTCCTTTTTT   TCTTTGGTGC  GTCCTTGGCG 15370                15380       15390       15400       15410       15420
GCAGGAACCA   CGCGGAACAT  GGGACACTAT  CTGGAAATCC   TGTTCAACGT  CATCGTCTTC
CGTCCTTGGT   GCGCCTTGTA  CCCTGTGATA  GACCTTTAGG   ACAAGTTGCA  GTAGCAGAAG 15430                15440       15450       15460       15470       15480
ACTCTGCTGC   TCGGCGTCAT  GGTCAGTATC  GTCGCTTGGT   ACTTCACGTG  AACCACCGTC
TGAGACGACG   AGCCGCAGTA  CCAGTCATAG  CAGCGAACCA   TGAAGTGCAC  TTGGTGGCAG 15490                15500       15510       15520       15530       15540
GTCCCGGTTT   AAAAACCATC  ATCGACGGCC  GTTATAAAGC   CACCCGGACA  CGGCCGCGG
CAGGGCCAAA   TTTTTGGTAG  TAGCTGCCGG  CAATATTTCG   GTGGGCCTGT  GCCGGCGCC 15550                15560       15570       15580       15590       15600
CACTTGCCTA   CGGCGCTGCT  TCAGGGAAAC  TCCTCTTCCT   TCTGCTCTTC  CTCCTTCACC
GTGAACGGAT   GCCGCGACGA  AGTCCCTTTG  AGGAGAAGGA   AGACGAGAAG  GAGGAAGTGG
```

*FIG. 1Q-1*

```
15610      15620      15630      15640      15650      15660
GCAGGGATCG TTTCCCTCGA CCAGGGACTC GCCGAAGCAA CCGCCGGAGC AACCTGGAGG
CGTCCCTAGC AAAGGGAGCT GGTCCCTGAG CGGCTTCGTT GGCGGCCCTCG TTGGACCTCC 15670      15680      15690      15700      15710      15720
AGTCGCGGCA TGACGGGCGCC CAAGTGTGTC ACCACCAGTA CTTATCTGGT CAAGACCAAG
TCAGCGCCGT ACTGCCGCGG GTTCACACAG TGGTGGTCAT GAATAGACCA GTTCTGGTTC 15730      15740      15750      15760 UL149 15770      15780
GAACAGCCCT GGTGGCCCGA CAACGCCATC AGGAGATGGT GGATCAGTGT TGCTATCGTC
CTTGTCGGGA CCACCGGGCT GTTGCGGTAG TCCTCTACCA CCTAGTCACA ACGATAGCAG 15790      15800      15810      15820      15830      15840
ATCTTCATCG GAGTCTGTCT GGTGGCCCCTG ATGTACTTTA CGCAGCAGCA GGCACGCAGC
TAGAAGTAGC CTCAGACAGA CCACCGGGAC TACATGAAAT GCGTCGTCGT CCGTGCGTCG 15850      15860      15870 UL150 15880      15890      15900
GGGAGCAGCA GCGGCTAGAC AAGTCTCTGG CGGCTACAGC TCCAAGCGCC GTAGCCGGGC
CCCTCGTCGT CGCCGATCTG TTCAGAGACC GCCGATGTCG AGGTTCGCGG CATCGGCCCG 15910      15920      15930      15940      15950      15960
CGCCTGCCGA TCGCGACGTC GTGGACCATC GAACAGAGAC TCACGCGTAC GAGACCCCGA
GCGGACGGCT AGCGCTGCAG CACCTGGTAG CTTGTCTCTG AGTGCGCATG CTCTGGGGCT 15970      15980      15990      16000      16010      16020
GGTACGCCAC GCGGTGCCTA ACGCGGTATA CCACACCCGT ACGGTCTGCA GTGCGGCGTA
CCATGCGGTG CGCCACGGAT TGCGCCATAT GGTGTGGGCA TGCCAGACGT CACGCCGCAT 16030      16040      16050      16060      16070      16080
CAACGTGTGG AAAACGCGTT GCGTCGCAGA GTCCGCCACG TTCCTGTCTT GTCGCTCCCC
GTTGCACACC TTTTGCGCAA CGCAGCGTCT CAGGCGGGTGC AAGGACAGAA CAGCGAGGGG
```

*FIG._1Q-2*

```
16090      16100      16110      16120 UL149 16130      16140
AATCGTCTCC CGCACACCCC CCGCGACACC CAGAGGGCGG GTGAGCCAAG TATTCTTAAG
TTAGCAGAGG GCGTGTGGGG GGCGCTGTGG GTCTCCCGCC CACTCGGTTC ATAAGAATTC 16150      16160      16170      16180      16190      16200
GCCGTTCTTT GTTCCATAGC CCATAAATTG TTGATTCCGG AGCTCGTTGG CGCGGAAATA
CGGCAAGAAA CAAGGTATCG GGTATTTAAC AACTAAGGCC TCGAGCAACC GCGCCTTTAT 16210      16220      16230      16240      16250      16260
GCCGGATAAG GGGAGCAACA ACCGTTGGCG AAAGCCGTCC CGCTCATTCA GTCCGGGTTT
CGGCCTATTC CCCTCGTTGT TGGCAACCGC TTTCGGCAGG GCGAGTAAGT CAGGCCCAAA 16270      16280      16290      16300      16310      16320
CGGTCCCAGT CGGACGTGTG ACCGTTGGGC AACGGAACGG CGTTTCACTG CCAAAATCGT
GCCAGGTCA GCCTGCACAC TGGCAACCCG TTGCCTTGCC GCAAAGTGAC GGTTTTAGCA 16330      16340      16350      16360      16370      16380
ATCGGGTAGT GTACGAGACG TCGGCGGGTGC AGAATGCGAC TCGGCGGGTA GCTCGCCGTC
TAGCCCATCA CATGCTCTGC AGCCGCCACG TCTTACGCTG AGCGCCGCAT CGAGCGGCAG 16390      16400      16410      16420      16430      16440
GCTATGCGGC TCGTCCTGGCT GTGGCCGGC CTGGCCGGCT GTCTGCCTCC AGATCTGTTG
CGATACGCCG AGCAGGCCA CACCGGCGCCC GACCGGCCGA CAGACGCAGG TCTAGACAAC 16450      16460      16470      16480      16490      16500
GCCTTTTGGT TCCTCTGGCT GCTGCTGCGT GTGTGCTTTG GTAGACGCGG TGGCAGTTTG
CGGAAAACCA AGGAGACCGA CGACGACGCA CACACGAAAC CATCTGCGCC ACCGTCAAAC 16510      16520      16530      16540      16550      16560
CGGTCTGCGG TAAGTGAGGA TGTCGCCGAG CAAACGCCACT TGCGGGCGCGT GGGCGGCACG
GCCAGACGCC ATTCACTCCT ACAGCGGCTC GTTTGCGTGA ACGCCGGCA CCCGCCGTGC
```

FIG._1R-1

```
    16570      16580      16590      16600      16610      16620
CGTGTCATTG TAGGTTCGTT GCCAGATGGC AAGTGCTGTC AACAGCAGGC GTTGTGGGCG
GCACAGTAAC ATCCAAGCAA CGGTCTACCG TTCACGACAG TTGTCGTCCG CAACACCCGC 16630      16640      16650      16660      16670      16680
GTCGGTGTAT TTTTGTGGGT TGCGGTGAGA GTCGGCACTC GGTGTTTTGT GAGTCATCTC
CAGCCACATA AAAACACCCA ACGCCACTCT CAGCCGTGAG CCACAAAACA CTCAGTAGAG 16690      16700      16710      16720      16730      16740
AACTATCTGT GTTGCTTTGA GCAGCGTCCA GAACAGCGAC GCGACTTTGG GGATGGCCTC
TTGATAGACA CAACGAAACT CGTCGCAGGT CTTGTCGCTG CGCTGAAACC CCTACCGGAG 16750      16760      16770      16780      16790      16800
GTGCTCACCT CCGCGGAGAG CGCCGCCGGA CCTGCTCGTC AGCAGCGAGC TACGCAGACG
CACGAGTGGA GGCGCCTCTC GCGGCGGCCT GGACGAGCAG TCGTCGCTCG ATGCGTCTGC 16810      16820      16830      16840      16850      16860
GAATATCTGG AGGAGAGTTA CGTGTGTCAC AGGAGAGCGC GGGTCTCCGG CGGTAACGAC
CTTATAGACC TCCTCTCAAT GCACACAGTG TCCTCTCGCG CCCAGAGGCC GCCATTGCTG 16870      16880      16890      16900      16910      16920
GGCGGTGTCG TCGACACGTG TGCGGCCTGT TGTGCTCTGC GGAAAAGTGC CGGTCTCGGA
CCGCCACAGC AGCTGTGCAC ACGCCGGACA ACACGAGACG CCTTTTCACG GCCAGAGCCT 16930      16940      16950      16960      16970      16980
GACCGTGGAC GAAAAAGAGA ACGCAGCAGC TACCGCTGGC GGCGGCGGGC TTAATGCAGC
CTGGCACCTG CTTTTTCTCT TGCGTCGTCG ATGGCGACCG CCGCCGCCCG AATTACGTCG
```

*FIG._1R-2*

```
       16990      17000      17010      17020      17030      17040
CGTTGATGTT CGACGTTGTG AGCACTCGGA AACAGCGGTG AGGCAGAAGG TCGATTCTCC
GCAACTACAA GCTGCAACAC TCGTGAGCCT TTGTCGCCAC TCCGTCTTCC AGCTAAGAGG 17050      17060      17070      17080      17090      17100
AGGGAACGAC AGTCGATGCG TGGTAGCCGC AGCAGGTGAG GTTGGGGCCG ACAACGTGTT
TCCCTTGCTG TCAGCTACGC ACCATCGGCG TCGTCCACTC CAACCCCGGC TGTTGCACAA 17110      17120      17130      17140      17150      17160
GCGGATTGTG GCGAGAACGT CGTCCTCCCC TTCTTCACCG CCCCACCCAC CCTCGGTTGG
CGCCTAACAC CGCTCTTGCA GCAGGAGGGG AAGAAGTGGC GGGGTGGGTG GGAGCCAACC 17170      17180      17190      17200      17210      17220
TGTTTCTTTT TTCTTGTGTC CTGCAGATAG TTCCACGGAC AGCGACGGCA AGTCCATAAT
ACAAAGAAAA AAGAACACAG GACGTCTATC AAGGTGCCTG TCGCTGCCGT TCAGGTATTA 17230      17240      17250      17260      17270      17280
CAGCGGTGTG CAAGTGGTGG AACACGACGA AGATATCATC GCGCCGCAGA GTTTGTTGTG
GTCGCCACAC GTTCACCACC TTGTGCTGCT TCTATAGTAG CGCGGCGTCT CAAACACCAC

17290 UL151   17300      17310      17320      17330      17340
CACGGCGTTC AAGGAAGCCC TCTGGGATGT GGCTCTGTTG GAAGTGCCGC GTTGGGCGTG
GTGCCGCAAG TTCCTTCGGG AGACCCTACA CCGAGACAAC CTTCACGGCG CAACCCGCAC 17350      17360      17370      17380      17390      17400
GCAGGGGCTGG AAGAGGTGGC GCAACAGCGA GGCCGGGCGT CGATGGAGTG CTGGGTCTGC
CGTCCCCGACC TTCTCCACCG CGTTGTCGCT CCGGCCCGCA GCTACCTCAC GACCCAGACG 17410      17420      17430      17440      17450      17460
GTCGGCTTCC AGCTTGTCTG ACTTGGCGGG CGAGGCCCGTT TGGAATTGG TGGGATCGGT
CAGCCGAAGG TCGAACAGAC TGAACCGCCC GCTCCGGCAA CCTCTTAACC ACCCTAGCCA
```

FIG._1S-1

FIG. 1S-2

```
17470      17480      17490      17500      17510      17520
CGTCGCGTAC GTGATCCTTG AACGTCTGTG GTTGGCAGCC AGAGGTTGGG TGTGCGAAAC
GCAGCGCATG CACTAGGAAC TTGCAGACAC CAACCGTCGG TCTCCAACCC ACACGCTTTG 17530      17540      17550      17560      17570      17580
AGGTGTGGAA GCCGAGGAGG CCATGTCGCG GCGGCGACAG CGCATGCTGT GGCGTATTGT
TCCACACCTT CGGCTCCTCC GGTACAGCGC CGCCGCTGTC GCGTACGACA CCGCATAACA 17590      17600      17610      17620      17630      17640
TCTCTCGTGG AGGCGACGGC GAATGCAGCA GACGGTGTTC GATGGAGATG GCGTGCGGGG
AGAGAGCACC TCCGCTGCCG CTTACGTCGT CTGCCACAAG CTACCTCTAC CGCACGCCCC 17650      17660      17670      17680      17690      17700
AAGAAAGCGC CGTGTTGTGA GCAGACGACG TAGGATGCGG GACGTCGGAG CACATGGGCC
TTCTTTCGCG GCACAACACT CGTCTGCTGC ATCCTACGCC CTGCAGCCTC GTGTACCCGG 17710      17720      17730      17740      17750      17760
ATGTGTGGTG GCAGATGGCG GTGTCCGCTG GTGTCTGCTG CGGCAGTGCA TAGACGAAGC
TACACACCAC CGTCTACCGC CACAGGCGAC CACAGACGAC GCCGTCACGT ATCTGCTTCG

UL150      17810      17820
17770      17780      17790      17800      ATGCAGCGTT GCGTGTATAA
AACATGTCGC TGTGAAGAGA TAGAGTGTGA GCATAGCTGC          GGCACATATT
TTGTACAGCG ACACTTCTCT ATCTCACACT CGTATCGACG TACGTCGCAA CGCACATATT
                                            →

17830      17840      17850      17860      17870      17880
GCGGSGGGGA TTAAGACGTT AATAAAGAAT AGCGGCGGTT CTGATAGGGC GACCGCTGAA
CGCCCCCCCT AATTCTGCAA TTATTCTTA  TCGCCGCCAA GACTATCCCG CTGGCGACTT 17890      17900      17910      17920      17930      17940
GTGAGCTGCG TGTGCGTGTG GTTTGTGGAG TCCCCGCCGC CCCCGGTCCC GTGTCCGCCG
CACTCGACGC ACACGCACAC CAAACACCTC AGGGGCGGCG GGGGCCAGGG CACAGGCGGC
```

```
       17950              17960              17970              17980              17990              18000
GCAAAGCCCC     CCGGNTCCGC  ACACTCCTGG  CCGGCGCAACC  CTCGTCGCTG  CAAAAGCCCC
CGTTTCGGGG     GGCCNAGGCG  TGTGAGGACC  GGCGCGTTGG  GAGCAGCGAC  GTTTTCGGGG 18010              18020              18030              18040              18050              18060
CCGTCCCCGC     ACACCCCCGC  GACCGCCGGT  CCCGGCGAGTC  CCCGTCCCCG  CCGCAAAAGG
GGCAGGGGCG     TGTGGGGGCG  CTGGCGGCCA  GGGCGCTCAG  GGGCAGGGGC  GGCGTTTTCC 18070              18080              18090              18100              18110              18120
CCCCCGTCCT     CGCCGCAAAC  ACCCCCGTCA  CCCCCGTCCC  TCAGNCCGGG  TCCGGCGAGTC
GGGGGCAGGA     GCGGCGTTTG  TGGGGGCAGT  GGGGGCAGGG  AGTCNGGCCC  AGGCGCTCAG 18130              18140              18150              18160              18170              18180
CCCGTTCCCA     GCGTAATCCC  CGTACCCGCA  ACGNCCCGGN  CCCACCGTCG  TCCCGCACAC
GGGCAAGGGT     CGCATTAGGG  GCATGGGCGT  TGCNGGGCCN  GGGTGGCAGC  AGGGCGTGTG 18190              18200              18210              18220              18230              18240
CCCCCGTCCC     CCAGCCCGGT  GCCCAGCCGTG  CGAAAAAAGC  TCCGTCCCTC  ACACCCGCAG
GGGGGCAGGG     GGTCGGGCCA  CGGGTCGCAC  GCTTTTTTCG  AGGCAGGGAG  TGTGGGCGTC 18250              18260              18270              18280              18290              18300
CAGCGCGGGTG   AAACCCCGTC   CCCAGCGCCG   TGCCGCTGAC   AAAGACCATG
GTCGCGCCAC    TTTGGGCAG    GGGTCGCGGC   ACGGCGACTG   TTTCTGGTAC
                                                      ↓ UL151

18310              18320
GGACGACACG     CACAGGCA..  ......  ......  ......  ......  18360
CCTGCTGTGC     GTGTCCGT..
```

FIG._1T

```
         10         20         30         40         50         60
ATCGGGCGCC AGAGCTAGAT CAGGGCGTATC AAATTCCACT GCCAGGCGAC CTGATTCTAA
TAGCCCGCGG TCTCGATCTA GTCCGCATAG TTTAAGGTGA CGGTCCGCTG GACTAAGATT 70         80         90        100        110        120
CGGTTCCACG ATCCGGGAGA GCGTTTCTAG ATATAGAGCA AAGCGTACCA CGTCTACCTG
GCCAAGGTGC TAGGCCCTCT CGCAAAGATC TATATCTCGT TTCGCATGGT GCAGATGGAC 130        140        150        160        170        180
CGGTGTAAAA AACTGTGTG GGCGTTCACC GTCGTTGACC ACGTAAGCCA CGTAGAGGCC
GCCACATTTT TTGACAACAC CCGCAAGTGG CAGCAACTGG TGCATTCGGT GCATTCCGG 190        200        210        220        230        240
AACATTTCC ACCACGGGTT CTAGCTGCAG GCGGCACGTA AAGCTTAGAA ACGACGGCTG
TTGTAAAAGG TGGTGCCCAA GATCGACGTC CGCCGTGCAT TTCGAATCTT TGCTGCCGAC 250        260        270        280        290        300
TACGGTTTGG TTCCCGTGAA GCTGAAGCGT CACTTCCTTG CCGGGGCTCA CCGTGCTGTA
ATGCCAAACC AAGGGCACTT CGACTTCGCA GTGAAGAAC GGCCCCGAGT GGCACGACAT 310        320        330        340        350        360
ACGCCGCACC GAGTCGGTCA TCTGCTCCAG ATCGGTAGAC TAGCTCGGTG TGCAATGCAT
TGCGGCGTGG CTCAGCCAGT AGACGAGGTC TAGCCATCTG GTCTTCCCGC ACGTTACGTA 370        380        390        400        410        420
ACTGTCCCAG TCGCGACACG CAGCCCAGCC TAGCTCGGTG AAGGGTCGAC GCACACCCGA
TGACAGGGTC AGCGCTGTGC GTCGGGTCGG ATCGAGCTG TTCCCAGCTG CGTGTGGGCT 430        440        450        460        470        480
AAAAGTGTGC TTGAAGACCA GGGGGTCGCC TCGGTAGCTC AGTAGCCGAA CATGCACATA
TTTTCACACG AACTTCTGGT CCCCCAGCGG AGCCATCGAG TCATCGGCTT GTACGTGTAT
```

*FIG._2A-1*

```
                                490        500        510        520        530        540
                         GTCCGGGCTA CGTTGACAGA CGGCCCGTAG ACAGGCAGGA CAAGCCGTGAA CAGCCAAGCGC
                         CAGCGCCCGAT GCAACTGTCT GCCGGGCATC TGTCCGTCCT GTTCGCACTT GTCGTTCGCG
                                550        560        570        580        590        600
                         AACATGCTGC GGGTTAGAAA ATGCGGCGTG CCCGGCCACCG CCCGACTCAT AAACGCTACC
                         TTGTACGACG CCCAATCTTT TACGCCGCAC GGCCGGTGGC GGGCTGAGTA TTTGCGATGG
                                610        620        630        640        650        660
                         AGCATGACGT CTCAGATCAC ACAAGTGACG AGGAGCGTAC CGCAAATCAC TAGGGAAAAG
                         TCGTACTGCA GAGTCTAGTG TGTTCACTGC TCCTCGCATG GCGTTTAGTG ATCCCTTTTC
                                670        680        690        700        710        720
                         GCCAGCAGAG CCCGATAGTC TTGCTCTTCG CGAACGATCT CGTCCGGTTC CTCGCAGTCT
                         CGGTCGTCTC GGGCTATCAG AACGAGAAGC GCTTGCTAGA GCAGGCCAAG GAGCGTCAGA
                                730        740        750        760        770        780
                         TCGTGGTCCA CAGAAGATGA GGAGCCAGGAT TCTTCGTTAA TTTCTGCCAG GATACTAGTG
                         AGCACCAGGT GTCTTCTACT CCTCGTCCTA AGAAGCAATT AAAGACGGTC CTATGATCAC
                                790        800        810        820        830        840
                         CTGTACCACA CCAGAGCGCT CAGCGTGCCC AGGGCTACCG CACGGTAAAA TAGGACATG
                         GACATGGTGT GGTCTCGCGA GTCGCACGGG TCCCGATGGC GTGCCATTTT ATCCCTGTAC
                    UL147 850        860        870        880        890        900
                         ATCACCAGCG CAATCTGAAG TGGTGGTAGT TCAGTTTCTT GGCGTATTTC CAGAGAAAGG
                         TAGTGGTCGC GTTAGACTTC ACCACCATCA AGTCAAAGAA CCGCATAAAG GTCTCTTTCC
                                910        920        930        940        950        960
                         CTTTGTAGGC CGTAGGGACT GGCCAGGCAC CGAACTCAAT ATTGGTAGAC ACTACGTCGT
                         GAAACATCCG GCATCCCTGA CCGGTCCGTG GCTTGAGTTA TAACCATCTG TGATGCAGCA
```

FIG._2A-2

```
      970        980        990       1000       1010       1020
AAATGCGTTG TTCCTCGTCT AAGATTAACC GAAAAAATAG CCGGTTGATG TGACGACGCA
TTTACGCAAC AAGGAGCAGA TTCTAATTGG CTTTTTTATC GGCCAACTAC ACTGCTGCGT 1030       1040       1050       1060       1070       1080
CGGCTTGCGC GTTAGGATTG AGACACTTGG TGCCCTTGTC CTTTAAAATA GCCAGCACTT
GCCGAACGCG CAATCCTAAC TCTGTGAACC ACGGGAACAG GAAATTTTAT CGGTCGTGAA 1090       1100       1110       1120       1130       1140
CCTGACGATT GCAGCTTTCG CTCGCCGCGA TTGGCTTAAG CAATTCAGTT CCGATTGGCA
GGACTGCTAA CGTCGAAAGC GAGCGGCGCT AACCGAATTC GTTAAGTCAA GGCTAACCGT 1150       1160       1170       1180       1190       1200
GAGTATTCAA CAGAATTTGG TTGTTACAAC GACAGCGTTT GTCGTAATCT TCCAATTCTA
CTCATAAGTT GTCTTAAACC AACAATGTTG CTGTCGCAAA CAGCATTAGA AGGTTAAGAT 1210       1220       1230       1240       1250       1260
AAAGATGGAC GGCTAGGGGA CATACGACAA ATAACATGTA TGCAGTCAAT TGCATATATC
TTTCTACCTG CCGATCCCCT GTATGCTGTT TATTGTACAT ACGTCAGTTA ACGTATATAG 1270       1280       1290       1300       1310       1320
GTACCGATAA AATGTTAGTG TGCGGATTCA GAATCGGATG ATGCAACCGT CTTAGCATCA
CATGGCTATT TTACAATCAC ACGCCTAAGT CTTAGCCTAC TACGTTGGCA GAATCGTAGT 1330       1340       1350       1360       1370       1380
TATCGAAAAA GTATACATAT TACCGATTCA TTATAATTAG GGAATTATTT CCAACGCGGA
ATAGCTTTTT CATATGTATA ATGGCTAAGT AATATTAATC CCTTAATAAA GGTTGCGCCT
UL147─►                                          UL152◄─

1390       1400       1410       1420       1430       1440
CGTTTGTTAG TGACAGCCGT TTCTTCTACA TGCGGTCCAT TACTATCCTT TACTTTTACC
GCAAACAATC ACTGTCGGCA AAGAAGATGT ACGCCAGGTA ATGATAGGAA ATGAAAATGG
```

FIG._2B-1

```
        1450       1460       1470       1480       1490       1500
AATACTCTGT GCCATGAGTT GTCTTTTTA CCATCCAGCC ATTTGACAA ATGATGATCG
TTATGAGACA CGGTACTCAA CAGAAAAAAT GGTAGGTCGG TAAACCTGTT TACTACTAGC 1510       1520       1530       1540       1550       1560
GGAGCTAAAC ATACAGGTTT ACCTCGAGGA GGCAATAGAT AATGTTGAGG TTTGTCACAC
CCTCGATTTG TATGTCCAAA TGGAGCTCCT CCGTTATCTA TTACAACTCC AAACAGTGTG 1570       1580       1590       1600       1610       1620
TCAGGAGGAT TGGGAGGGTC ACGACCAACC CAAAATAAGC CACCTATAGG ATGATGTAAA
AGTCCTCCTA ACCCTCCCAG TGCTGGTTGG GTTTTATTCG GTGGATATCC TACTACATTT 1630       1640       1650       1660       1670       1680
GCTTTGTGGG TACACGGACA ACGCAATTCT CTACTGTGAA CCCCATGGTA ATACATAAAT
CGAAACACCC ATGTGCCTGT TGCGTTAAGA GATGACACTT GGGGTACCAT TATGTATTTA 1690       1700       1710      UL152 1720  1730       1740
GCCATCAAAA GACTAATCAG CGAACCAAAA ATTAAATCGCA TTCTAATTTT ATTAACTACG
CGGTAGTTTT CTGATTAGTC GCTTGGTTTT TAATTTAGCGT AAGATTAAAA TAATTGATGC
                                              →

1750       1760       1770       1780       1790       1800
TCACTATCAG TAATTCGTAA TATCCGGTAT TCCCGGAAAA TCACTCAAAA CTGCGTCCAT
AGTGATAGTC ATTAAGCATT ATAGGCCATA AGGGCCTTTT AGTGAGTTTT GACGCAGGTA 1810       1820       1830       1840       1850       1860
GACACATCAA TTCCCGATAA GTACCCCCCT TTGAAATCGG ATCCCCCCAC ATACCAATCA
CTGTGTAGTT AAGGGCTATT CATGGGGGGA AACTTTAGCC TAGGGGGGTG TATGGTTAGT
```

FIG._2B-2

```
1870       1880       1890       1900       1910       1920
ATCACACAAC ACACAGGTTT AAAAATCGAT CACACGTCAA TTAGTTTCA  AAATCGATAC
TAGTGTGTTG TGTGTCCAAA TTTTTAGCTA GTGTGCAGTT AATCCAAAGT TTTAGCTATG 1930       1940       1950       1960       1970       1980
TGTTTATTAT CAGGAATCTA GACTAATTCT ACAATGACAG CTCTGAATTT CTCTCTCGTC
ACAAATAATA GTCCTTAGAT CTGATTAAGA TGTTACTGTC GAGACTTAAA GAGAGAGCAG 1990       2000       2010       2020       2030       2040
TTTCTTGTCA GGTTCTCATC ATCAATCTTC ACTTCCACCC ATCGAGGAGT CATCGTCGCT
AAAGAACAGT CCAAGAGTAG TAGTTAGAAG TGAAGGTGGG TAGCTCCTCA GTAGCAGCGA 2050       2060       2070       2080       2090       2100
CCAAAACCCT TTGGGGTCGC TGGTTGGAAA AGTCTCTGAC ACGATCCAGG CACCCCGTAC
GGTTTTGGGA AACCCCAGCG ACCAACCTTT TCAGAGACTG TGCTAGGTCC GTGGGCATG 2110       2120       2130       2140       2150       2160
CCAGTCCGAC TGATCTAGCT TACGGAGCAT CTCAACAGGC ATGAGCTGCA GGGCCACGGC
GGTCAGGCTG ACTAGATCGA ATGCCTCGTA GAGTTGTCCG TACTCGACGT CCCGGTGCCG 2170       2180       2190       2200       2210       2220
TGTCACGGCA GGGATTATTA CTACCGTTCA GGTAAACTGT ATCTCCCTGA GTTACCGTGA
ACAGTGCCGT CCCTAATAAT GATGGCAAGT CCATTTGACA TAGAGGGACT CAATGGCACT 2230       2240       2250       2260       2270       2280
TGGGTCTTTC TACATGTTGA CTTTGCGTAA AAAATCGCCG GTAAAAATGTT TTTTCTTGTT
ACCCAGAAAG ATGTACAACT GAAACGCATT TTTTAGCGGC CATTTTACAA AAAGAACAA 2290       2300       2310       2320       2330       2340
CATGTAAAAG TACCGGAACT AAAATGCTAG TTAGAATGGT TGCAGTTGCT ATTAGCGCGG
GTACATTTTC ATGGCCTTGA TTTTACGATC AATCTTACCA ACGTCAACGA TAATCGCGCC
```

FIG._2C-1

```
      2350              2360              2370              2380              2390              2400
CTAGTAACAG        TAGTTTAGTG        TTACATTGTA        TACCCATGTT        TTTAATAACT        ATGAATATTC
GATCATTGTC        ATCAAATCAC        AATGTAACAT        ATGGGTACAA        AAATTATTGA        TACTTATAAG 2410              2420              2430              2440              2450              2460
TGCTTCACAC        CATAAGTGCT        TAACCCACAA        AAACCACACG        GAGACATTAT        TGGCTAARAA
ACGAAGTGTG        GTATTCACGA        ATTGGGTGTT        TTTGGTGTGC        CTCTGTAATA        ACCGATTTTT 2470              2480              2490         2500   UL153 2510              2520
TAAAAACAAA        AGTTTATTGA        TGTGCATGTT        AGTTTTTAGT         CTAAAAATTCA       TCTGGTGTGT
ATTTTGTTT         TCAAATAACT        ACACGTACAA        TCCAAAAATCA       GATTTTAAGT        AGACCCAGCA
                                                                              ▼

2530              2540              2550              2560              2570              2580
ATTTGGAAG         TTTTGTATAA        CGCGGTCTTC        TGGGGACGCG        ACGGCTACCC        ATGTATAAGG
TAAACCCTTC        AAAACATATT        GCGCCAGAAG        ACCCCTGCGC        TGCCGATGGG        TACATATTCC 2590              2600              2610              2620              2630              2640
CTATAAGTGC        CACAGATACC        ACTATACCCG        CCCATACAGC        ATGAATTCCC        AGGGGAATGT
GATATTCACG        GTGTCTATGG        TGATATGGGC        GGGTATGTCG        TACTTAAGGG        TCCCCTTACA 2650              2660              2670              2680              2690              2700
CTATAAGTGC        TACAGTTTTT        ATTACATTGT        CCCACGTTCT        GCTATTATGC        TGGTTCTGATT
ATCACAAAAA        ATGTCAAAAA        TAATGTAACA        GGGTGCAAGA        CGATAATACG        ACCAGACTAA 2710              2720              2730              2740              2750              2760
CCTCTTTTGT        TTTACATTTA        TCAGTTATAG        GAGACGATGT        TGCAGTTCCT        GATAACACGG
GGAGAAAACA        AAATGTAAAT        AGTCCATATC        CTCTGCTACA        ACGTCAAGGA        CTATTGTGCC 2770              2780              2790              2800              2810              2820
TTAAATAGTA        GTTTTCCTTT        TTACCGTCAC        TGTAACGTTG        CAAAACGTAT        TTTCCAGCGT
AATTTATCAT        CAAAAGGAAA        AATGGCAGTG        ACATTGCAAC        GTTTGCATA         AAAGGTCGCA
```

FIG._2C-2

```
2830       2840       2850       2860       2870       2880
GTTCGGTAGT TACGTTGTAT ATAGTGAGAG AGGTCTTATT GCAGTCTAAA CACATGCCGT
CAAGCCATCA ATGCAACATA TATCACTCTC TCCAGAATAA CGTCAGATTT GTGTACGGCA 2890       2900       2910       2920       2930       2940
TCAGTGGGGA AGTTGAATAA TAATGTCCAA TGCTGCACAG TTGGTGTGCG CGAGGTCCAT
AGTCACCCCT TCAACTTATT ATTACAGGTT ACGACGTGTC AACCACACGC GCTCCAGGTA 2950       2960       2970       2980       2990       3000
ATTTTATCCA TTCTATATCG TGCCATACAT CCGTTCTACT GCAGTTTTTC AAAGTGACGT
TAAAATAGGT AAGATATAGC ACGGTATGTA GGCAAGATGA CGTCAAAAAG TTTCACTGCA 3010       3020       3030       3040       3050       3060
ATCCACCGAC ATATCCTGTT ACATTAATTA CTTCGTAATT TAAATTAGAG TGTTTATAAA
TAGGTGGCTG TATAGGACAA TGTAATTAAT GAAGCATTAA ATTTAATCTC ACAAATATTT 3070       3080       3090       3100       3110       3120
CGGTGTACAA ACTGCCATTG CAAGTTATGT TGCTGGTATT CAACCAGGGA GTAGTACTAT
GCCACATGTT TGACGGTAAC GTTCAATACA ACGACCATAA GTTGGTCCCT CATCATGATA 3130       3140       3150       3160       3170       3180
GAATGGTAGA AAACGTTAAT GTTGGCGTAG CGCTTGACGA TGATTTGAAG AGCGTTGAAG
CTTACCATCT TTTGCAATTA CAACCGCATC GCGAACTGCT ACTAAAACTT TCGCAACTTC 3190       3200       3210       3220       3230       3240
TGGTTGCTGA TGCGACTGAA GAAGCGGGTAG AGGGTTTGTG CGTGGTTCCA TTTGCGATAG
ACCAACGACT ACGCTGACTT CTTCGCCATC TCCCAAACAC GCACCAAGGT AAACGCTATC 3250       3260       3270       3280       3290       3300
CTGAAGTGCT GTTAGCATCG GTGACAGAGT TAGAAGAATT TGTGATAGTG GAGGCGGTGG
GACTTCACGA CAATCGTAGC CACTGTCTCA ATCTTCTTAA ACACTATCAC CTCCGCCACC
```

FIG._2D-1

FIG. 2D-2

```
3310       3320       3330            3340       3350       3360
AGGTAAAGGC AATTGCACGG ACAGGAGCAC GTGTCATTGC AACCTTCAGA TATCGTAATC
TCCATTTCCG TTAACGTGCC TGTCCTCGTG CACAGTAACG TTGGAAGTCT ATAGCATTAG
                                    UL153
                                         ↓

3370       3380       3390       3400       3410       3420
ATCAGTAACG TCCACTTAAC CGTAAATCTC CAGTCCATAA CGTTATTAAA TTTCGGTTAA
TAGTCATTGC AGGTGAATTG GCATTTAGAG GTCAGGTATT GCAATAATTT AAAGCCAATT 3430       3440       3450       3460       3470       3480
CGGGCATTGA TGTTTCTTCG GACGTTGTTG ATCTTTCTTG CCCGTTTATT TTCTGATATG
GCCCGTAACT ACAAAGAAGC CTGCAACAAC TAGAAAGAAC GGGCAAATAA AAGACTATAC 3490       3500       3510       3520       3530       3540
GTCTCATAAG ACATTATCC GGAAACGTTG CTTAGTCCTC GTGCTCAGGA TTGTATCGAA
CAGAGTATTC TGTAAATAGG CCTTTGCAAC GAATCAGGAG CACGAGTCCT AACATAGCTT
                                UL154
                                ↓

3550       3560       3570       3580       3590       3600
CTATGAATTC TGATTCACTT ATATCGTCAC TTAATGGATG ATATTTTTTA TTTAGAGCTC
GATACTTAAG ACTAAGTGAA TATAGCAGTG AATTACCTAC TATAAAAAAT AAATCTCGAG 3610       3620       3630       3640       3650       3660
GTCGGACGAA AAATAGGAGA ATGCAGGCTA CACAAATTAA TGCTAACGTC CACGTAGTGC
CAGCCTGCTT TTTATCCTCT TACGTCCGAT GTGTTTAATT ACGATTGCAG GTGCATCACG 3670       3680       3690       3700       3710       3720
GTCTGCCGTG TGATGTGTTA GAATGATTGT TATAGCGGTA TAAATGATCT ATAGATGATG
CAGACGGCAC ACTACACAAT CTTACTAACA ATATCGCCAT ATTTACTAGA TATCTACTAC 3730       3740       3750       3760       3770       3780
TGGCTGTATT GTCTTCATAA TTGGTCGGTT TATGAGAAGT GTCCCATTCG TGCTTTGGTT
ACCGACATAA CAGAAGTATT AACCAGCCAA ATACTCTTCA CAGGGTAAGC ACGAAACCAA
```

```
      3790        3800        3810        3820        3830        3840
CTTCACATAC  CCAGGGATTC  ACGTGTGTCC  CGTTTGTGTT  GTTTCTAGGA  TGTATTTGCA
GAAGTGTATG  GGTCCCTAAG  TGCACACAGG  GCAAACACAA  CAAAGATCCT  ACATAAACGT 3850        3860        3870        3880        3890        3900
GATTARAGTT  TTGATTTTGT  TCGGAGGGAT  GCCCAGTTTT  ATAACATCGA  AAGCTATATT
CTAATTTCAA  AACTAAAACA  AGCCTCCCTA  CGGGTCAAAA  TATTGTAGCT  TTCGATATAA 3910        3920        3930        3940        3950        3960
TACCAGAATG  AGTAAAATTA  AGACCGTACA  GAGATAAAGA  TAAATTACGA  TCGCATGTAA
ATGGTCTTAC  TCATTTTAAT  TCTGGCATGT  CTCTATTTCT  ATTTAATGCT  AGCTACATT 3970        3980        3990        4000        4010        4020
AACATAAATC  ATAGTGATGT  TTTAGATAAT  TTGTGTGCCA  CTCACATAGT  ATACGCGAAT
TTGTATTTAG  TATCACTACA  AAATCTATTA  AACACACGGT  GAGTGTATCA  TATGCGCTTA 4030        4040        4050        4060        4070        4080
GGAGGATTT   CAATGAATGG  TTATGATATT  TTCCATTTCT  TATGTTGGGA  TGGGTGTATT
CCTCCTAAAA  GTTACTTACC  AATACTATAA  AAGGTAAAGA  ATACAACCCT  ACCCACATAA 4090        4100        4110        4120        4130        4140
TTCCGTGTGT  GGATATATTA  AAATGTCTAA  GCCAGGCTGT  TTTGTAGCAC  GATGTGATGG
AAGGCACACA  CCTATATAAT  TTTACAGATT  CGGTCCGACA  AAACATCGTG  CTACACTACC 4150        4160        4170        4180        4190        4200
TTAGGTTGTG  TGTTATAGTA  ATATTGTCTC  CTTGTGCCGC  CTCCAATAAT  GTTTCAGATT
AATCCAACAC  ACAATATCAT  TATAACAGAG  GAACACGGCG  GAGGTTATTA  CAAAGTCTAA 4210        4220        4230        4240        4250        4260
CTTTTGATAT  CGTATTATTT  GTACTGTTAG  GCGATGAGCA  AGTTGGAAGC  GGTGTAGTGA
GAAAACTATA  GCATAATAAA  CATGACAATC  CGCTACTCGT  TCAACCTTCG  CCACATCACT
```

```
         4270                 4280                 4290                 4300                 4310                 4320
CGTTTTCATT           TGCATTTATC           ATAGTAGTAG           TGTTGGTTGA           TAATGATATA           GTTTGCAAAG
GCAAAAGTAA           ACGTAAATAG           TATCATCATC           ACAACCAACT           ATTACTATAT           CAAACGTTTC
         4330                 4340                 4350                 4360                 4370                 4380
TCACAGTACT           ATCGGTTACA           TGCTGTGTCG           ATGAATTCGT           GTCGCCGTTT           GGTGAAGTTG
AGTGTCATGA           TAGCCAATGT           ACGACACAGC           TACTTAAGCA           CAGCGGCAAA           CCACTTCAAC
         4390                 4400                 4410                 4420                 4430                 4440
TTATTACAGT           TACGTTAGTT           GTAGATGTTT           GGGTAGATAT           GGTGGAAATA           GTTGAGGTCA
AATAATGTCA           ATGCAATCAA           CATCTACAAA           CCCATCTATA           CCACCTTTAT           CAACTCCAGT
         4450                 4460                 4470                 4480                 4490                 4500
CGTCTGTGCC           TTTTACAGAG           CTTGCAGTGA           ATCCTGTGGA           TGTGTTGACG           TTGCCATTGG
GCAGACACGG           AAAATGTCTC           GAACGTCACT           TAGGACACCT           ACACAACTGC           AACGGTAACC
         4510                 4520                 4530                 4540                 4550                 4560
AGGATGTGAA           CATAGTGGTA           GACATTTCGG           TGGTTTGTAA           CGTAGATGTC           AGTTGTGTAG
TCCTACACTT           GTATCACCAT           CTGTAAAGCC           ACCAAACATT           GCATCTACAG           TCAACACATC
         4570                 4580                 4590                 4600                 4610                 4620
TAGATATTAA           GCTTGTGGGT           GTAATCGACG           TGGAAGTATT           GGCGATAGTG           GTGTTGTTAC
ATCTATAATT           CGAACACCCA           CATTAGCTGC           ACCTTCATAA           CCGCTATCAC           CACAACAATG
         4630                 4640                 4650                 4660                 4670                 4680
ACTTGCTTTT           CTGCAGAATC           CAAAAAATAA           TAAACATGCA           TATTATTTGC           GTATATGATG
TGAACGAAAA           GACGTCTTAG           GTTTTTTATT           ATTTGTACGT           ATAATAAACG           CATATACTAC
         4690                 4700                 4710                 4720                 4730                 4740
ACTTGTTCCA           CCGTCGATGT           TGTGTGCGCA  T.....    ........   ........   ........
TGAACAAGGT           GGCAGCTACA           ACACACGCGT  A.....
                                                   └UL154
```

FIG._2E-2

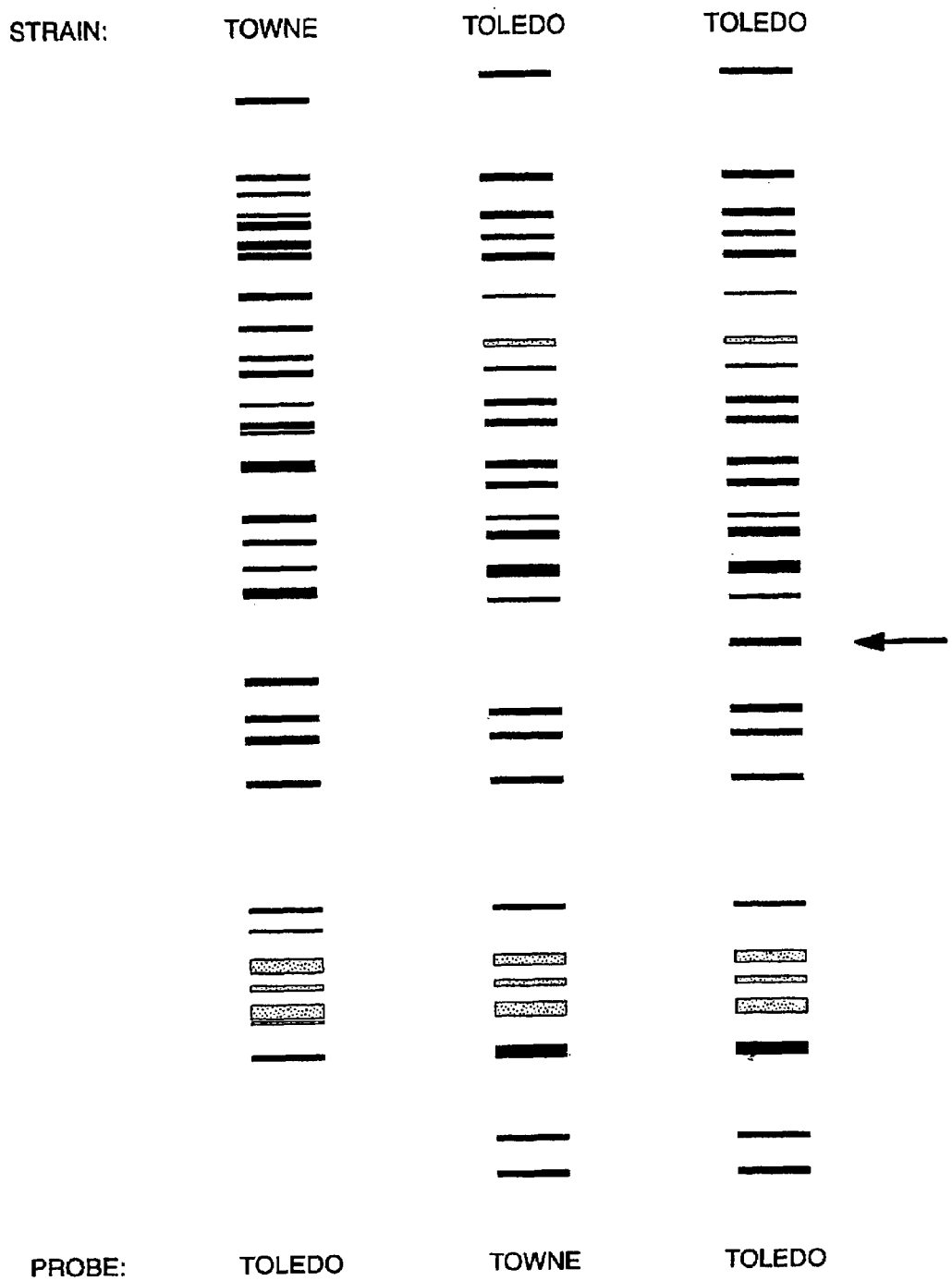
FIG._3

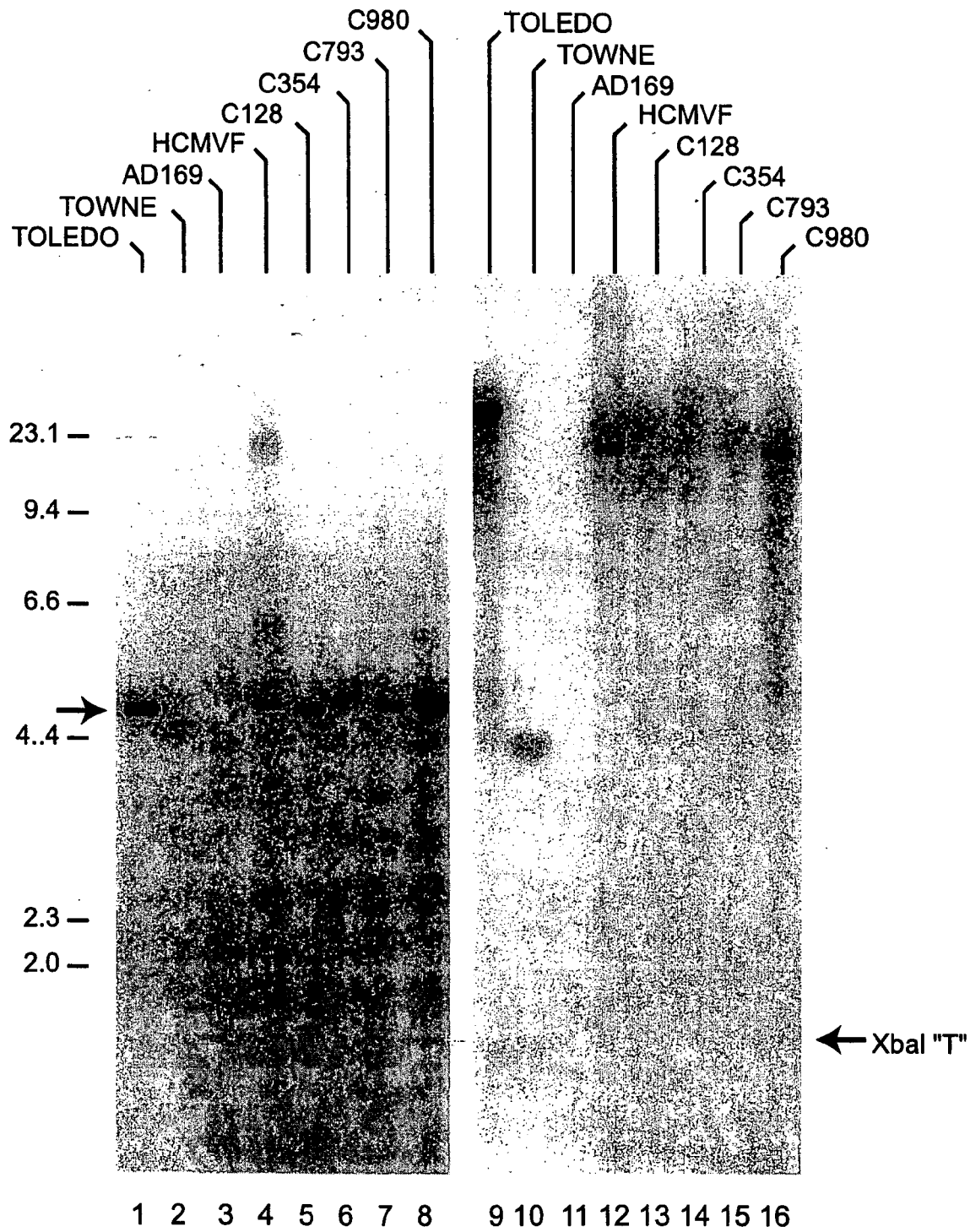
FIG._4

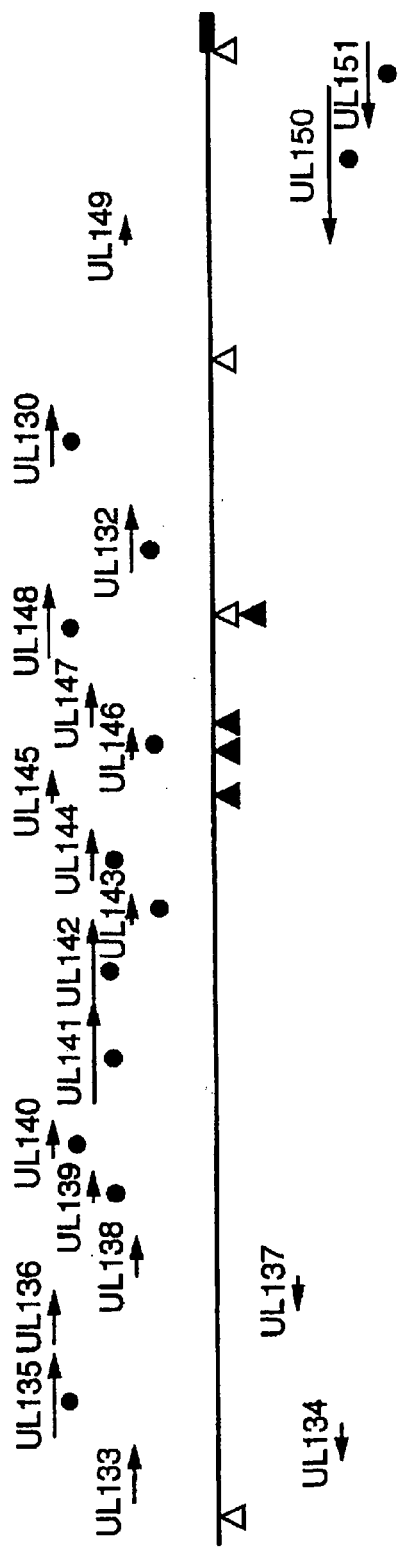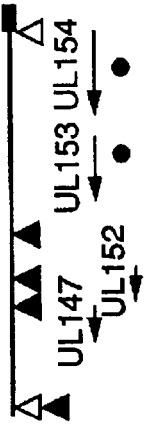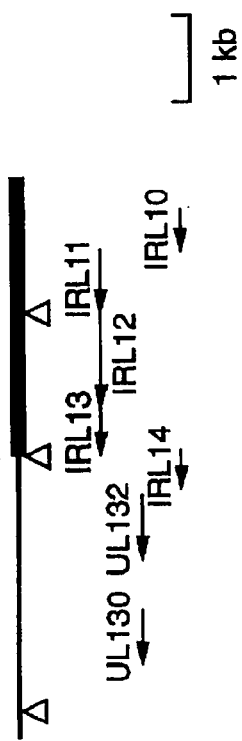
FIG._5

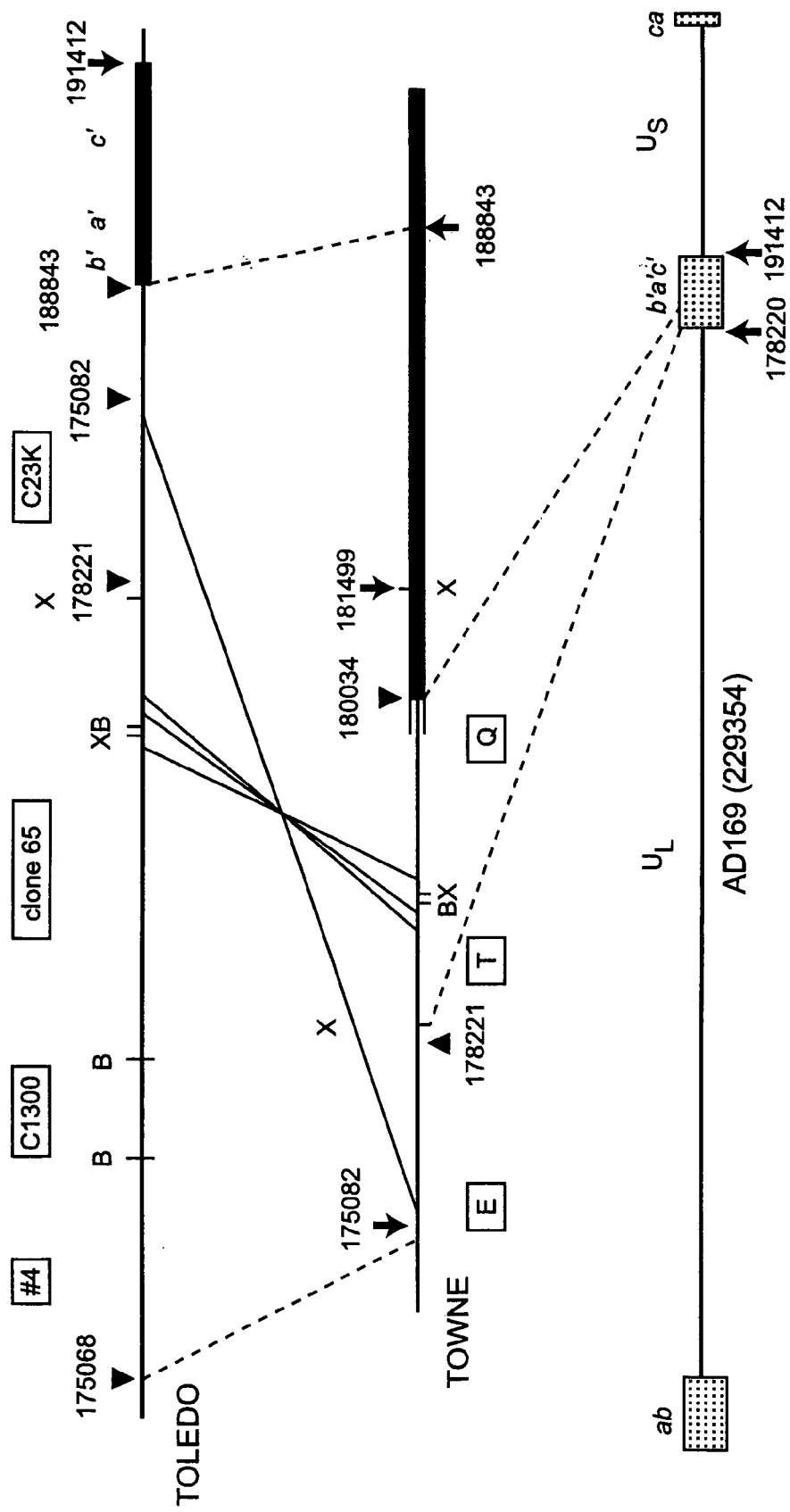
FIG._6

HUMAN CYTOMEGALOVIRUS DNA SEQUENCES

This is a continuation of application Ser. No. 10/394,848, filed Mar. 21, 2003, now abandoned, which is a divisional of application Ser. No. 09/892,100, filed Jun. 26, 2001 and issued as U.S. Pat. No. 6,635,477, which is a divisional of application Ser. No. 09/527,657, filed Mar. 17, 2000, now U.S. Pat. No. 6,291,236, which is a divisional of application Ser. No. 09/253,682, filed Feb. 18, 1999 and issued as U.S. Pat. No. 6,040,170, which is a divisional of application Ser. No. 08/926,922, filed Sep. 10, 1997 and issued as U.S. Pat. No. 5,925,751, which is a divisional of application Ser. No. 08/414,926, filed Mar. 31, 1995 and issued as U.S. Pat. No. 5,721,354.

TECHNICAL FIELD

This invention pertains to the field of virology, specifically to the diagnosis, treatment and prevention of viral infections in humans. More specifically, this invention relates to the diagnosis, treatment and prevention of human cytomegalovirus infections.

BACKGROUND

Human cytomegalovirus (HCMV) is a ubiquitous agent in human populations. Infections are generally asymptomatic, but there can be serious medical sequelae in immunocompromised individuals and in congenitally infected newborns. In immunocompromised individuals, HCMV infection can result in interstitial pneumonia, retinitis progressing to blindness and disseminated infection. Infections in newborns can be severely damaging, with multiple organ involvement including the central nervous system and may also result in auditory damage. The mechanisms of pathogenesis are not understood, although it is believed that host factors, such as cellular and/or humoral immune responses might be involved. See, Alford and Britt, "The Human Herpesviruses", eds Roizman, B., R. J. Whitley and C. Lopez, Raven Press, New York, 1993, pp 227–55. It has also been speculated that genetic variability (either structural or antigenic or both) among different strains of HCMV could be responsible for the variance in clinical manifestations observed. Pritchett, *J. Virol.* 36:152–61(1980); Lehner, *J. Clin. Microbiol.* 29:2494–2502(1991); Fries, *J. Infect. Dis.* 169:769–74(1994).

Considerable attention has been focused recently on the analysis of strain variation among HCMV isolates. Some twenty different HCMV strains have been isolated and differentiated by restriction analysis of PCR amplified DNA fragments. Chou, *J. Infect. Dis.* 162:738–42(1990).

One strain, the Towne strain, has been developed into a live, attenuated vaccine and administered with some success in renal transplant patients. See Quinnan, *Annals of Int. Med.* 101:478–83(1984); Plotkin, *Lancet* 1:528–30(1984). However, Towne strain vaccines who were directly challenged by low-passaged Toledo strain wild-type virus in one study were found to resist challenge doses of only 10 plaque-forming units (pfu) or less. Plotkin, *J. Infect. Dis.* 159: 860–65(1989). Therefore, it appears the Towne strain may be overly attenuated, i.e., genetically modified so extensively resulting from serial passage in cell culture that it has lost significant immunogenicity presumably due to the loss of genetic information during the cell passage. Advantageously however, the Towne strain has never been shown to reactivate.

DNA sequence heterogeneity between the Towne strain and another strain of HCMV, AD169, has been found. Pritchett, *J. Virol.* 36:152–61 (1980). (A restriction map of the AD169 HCMV genome is disclosed in U.S. Pat. No. 4,762,780.) Variation in the DNA content among other isolated strains of HCMV has also been detected. Huang, *Yale J. Biol. and Med.* 49:29–43 (1976). Cleavage patterns of restriction enzyme digests of HCMV DNA of various strains has been analyzed. Kilpatrick, *J. Virol.* 18:1095–1105 (1976); LaFemina, "Structural Organization of the DNA Molecules from Human Cytomegalovirus" in *Animal Virus Genetics*, eds. Field, B N and R. Jaenish, Academic Press, NY (1980); Chandler, *J. Gen. Virol.* 67:2179–92 (1986); Zaia, *J. Clin. Microbiol.* 28:2602–07 (1990). However, although the gross structural organization of the HCMV genome has been determined and strain-to-strain restriction site polymorphism mapped for many of the strains, strain-to-strain differences in the DNA sequences of the HCMV genome have not been determined. Only partial sequences have been deduced and compared. For example, the DNA and amino acid sequences of the envelope glycoprotein B [gpUL55(gB)] of both Towne and AD169 strains have been deduced, see Spaete, *Virology* 167:207–25 (1988), and compared with various clinical isolates, see Chou, *J. Infect. Dis.* 163:1229–34 (1991), to identify conserved regions and regions of variability. In addition, DNA sequence analysis of certain regions of the gp58/116 gene [gpUL55(gB)], the IMP gene and the IE-1/2 enhancer/promoter has been accomplished. Lehner, *J. Clin. Microbiol.* 29:2494–2502 (1991).

Whereas the complete DNA sequence of the AD169 strain of HCMV has been deduced, (EMBL Accession No. X17403), the complete DNA sequence of the Towne strain has not to our knowledge been deduced. However, it has been speculated that AD 169 and another laboratory strain, Davis, are missing two to four kilobase pairs (kb) of DNA sequence compared to the Towne strain at the extreme internal portions of both L repeats. LeFemina, supra, at 52–53.

The public health impact of HCMV infections has not been well controlled by current treatment strategies or available antiviral chemotherapies. Preventative vaccine strategies are likely to prove efficacious because of the observations that seropositive renal allograft recipients are protected from severe HCMV disease and maternal immunity protects the fetus from disease after intrauterine infection. Marshall and Plotkin, "Cytomegalovirus Vaccines" in The Human Herpesviruses, eds Roizman, B., R. J. Whitley and C. Lopez, Raven Press, New York, 1993, pps 381–95. However, an additional obstacle to the development of a vaccine for HCMV is the lack of an animal model system that can be used to test the safety and efficacy of vaccine candidates.

There remains a need in the art for efficacious vaccines for the prophylactic treatment of HCMV in humans.

SUMMARY OF THE INVENTION

In one aspect, the invention provides novel HCMV DNA sequences not heretofore recognized or known in the art. These novel HCMV sequences were isolated from the Toledo and Towne strains of HCMV and comprise DNA that is not shared by reference strain AD 169 of HCMV. Accordingly, in this aspect the invention provides novel, isolated, Toledo strain HCMV DNA sequences. As used herein, "isolated" means substantially free from other viral DNA sequences with which the subject DNA is typically found in its native, i.e., endogenous, state. These novel Toledo HCMV DNA sequences are characterized by comprising the same or substantially the same nucleotide sequence as in FIG. 1 (SEQ ID NO:6), or active fragments thereof. The DNA sequences may include 5' and 3' non-coding sequences flanking the coding sequence. The DNA sequences may be in inverted orientation with respect to the orientation shown in FIG. 1. Segments or fragments of the DNA sequence shown in FIG. 1 (SEQ ID NO:6) may be rearranged or inverted internally. The DNA sequences of the invention also comprise nucleotide sequences capable of hybridizing under stringent conditions, or which would be capable of hybridizing under said conditions but for the degeneracy of the genetic code to a sequence corresponding to the sequence of FIG. 1. FIG. 1 (SEQ ID NO:6) illustrates the DNA sequence of the novel Toledo strain HCMV. Twenty one open reading frames (ORFs) were identified in this sequence. The putative amino acid sequences of these novel Toledo strain HCMV ORFs are enumerated in sequence identification numbers 7 through 27, pages 58 through 78, infra. In FIG. 1, the beginning and ending of the 21 ORFs are identified by the arrows and the designations "UL133", "UL134", etc. (see infra.). In rearranged sequences of the invention, novel open reading frames may be created or destroyed.

In another aspect, the invention provides additional novel HCMV DNA sequences not heretofore recognized or known in the art. These additional sequences were isolated from the Towne strain of HCMV and comprise DNA that is not shared by the AD169 strain or by the Toledo strain of HCMV. Accordingly, in this aspect the invention provides novel Towne strain HCMV sequences. These novel Towne HCMV DNA sequences are characterized by as comprising the same or substantially the same nucleotide sequence as in FIG. 2 (SEQ ID NO:1), or active fragments thereof. The DNA sequence may include 5' and 3' non-coding sequences flanking the coding sequence. The DNA sequences of the invention also comprise nucleotide sequences capable of hybridizing under stringent conditions, or which would be capable of hybridizing under said conditions but for the degeneracy of the genetic code to a sequence corresponding to the sequence of FIG. 2 (SEQ ID NO:1). FIG. 2 (SEQ ID NO:1) illustrates the DNA sequence of the novel Towne strain HCMV. Four ORFs were identified in this sequence. The putative amino acid sequences of these novel ORFs are enumerated in sequence identification numbers 2 through 5, pages 42 through 45 infra. In FIG. 2, the beginning and ending of the 4 ORFs are identified by the arrows and the designations UL147, UL152, UL153 and UL154.

It is understood that the DNA sequences of this invention may exclude some or all of the signal and/or flanking sequences. In addition, the DNA sequences of the present invention may also comprise DNA capable of hybridizing under stringent conditions, or which would be capable of hybridizing under such conditions but for the degeneracy of the genetic code, to an isolated DNA sequence of FIG. 1 or FIG. 2. (SEQ ID NOS:6 and 1). As used herein, "stringent conditions" means conditions of high stringency, for example 6×SSC, 0.2% polyvinylpyrrolidone, 0.2% Ficoll, 0.2% bovine serum albumin, 0.1% sodium dodecyl sulfate, 100 μg/ml salmon sperm DNA and 15% formamide at 68 degrees C. (See Materials and Methods, Part C, infra.)

Accordingly, the DNA sequences of this invention may contain modifications in the non-coding sequences, signal sequences or coding sequences, based on allelic variation, species or clinical isolate variation or deliberate modification. Using the sequences of FIG. 1 and 2 (SEQ ID NOS:6 and 1), it is within the skill in the art to obtain other modified DNA sequences: the sequences can be truncated at their 3'-termini and/or their 5'-termini, the gene can be manipulated by varying individual nucleotides, while retaining the original amino acid(s), or varying the nucleotides, so as to modify amino acid(s). Nucleotides can be substituted, inserted or deleted by known techniques, including for example, in vitro mutagenesis and primer repair. In addition, short, highly degenerate oligonucleotides derived from regions of imperfect amino acid conservation can be used to identify new members of related viral and cellular families. RNA molecules, transcribed from a DNA of the invention as described above, are an additional aspect of the invention.

In another aspect, the invention provides novel HCMV proteins, which are substantially free from other HCMV proteins with which they are typically found in their native state. These novel HCMV proteins comprise the open reading frames (ORFs) UL133 (SEQ ID NO:7), UL134 (SEQ ID NO:8), UL135 (SEQ ID NO:9), UL136 (SEQ ID NO:10), UL137 (SEQ ID NO:11), UL138 (SEQ ID NO:12), UL139 (SEQ ID NO:13), UL140 (SEQ ID NO:14), UL141 (SEQ ID NO:15), UL142 (SEQ ID NO:16), UL143 (SEQ ID NO:17), UL144 (SEQ ID NO:18), UL145 (SEQ ID NO:19), UL146 (SEQ ID NO:20), UL147 (SEQ ID NO:21), UL148 (SEQ ID NO:22), UL149 (SEQ ID NO:24), UL150 (SEQ ID NO:25), and/or UL151 (SEQ ID NO:26) identified in the novel Toledo strain DNA sequence and UL147 (SEQ ID NO:2), UL152 (SEQ ID NO:3), UL153 (SEQ ID NO:4) and/or UL154 (SEQ ID NO:5) identified in the novel Towne strain DNA sequence. Two additional HCMV ORFs were identified in the novel Toledo strain DNA sequence, UL130 and UL132 (SEQ ID NOS:23 and 27). These two sequences are also present in AD169 (see FIG. 5). The proteins may be produced by recombinant genetic engineering techniques. They may additionally be purified from cellular sources infected with HCMV. They may also be synthesized by chemical techniques. One skilled in the art could apply a combination of the above-identified methodologies to synthesize the protein. Additionally, analogs of the HCMV proteins of the invention are provided and include truncated polypeptides, e.g., mutants in which there are variations in the amino acid sequence that retain biological activity, as defined below, and preferably have a homology of at least 80%, more preferably 90%; and most preferably 95%, with the corresponding regions of the HCMV Towne or Toledo amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27). Examples include polypeptides with minor amino acid variations from the native amino acid sequences of HCMV Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27); in particular, conservative amino acid replacements. Conservative replacements are those that take place within a family of amino acids that are related in their side chains. Genetically encoded amino acids are generally divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a major effect on activity or functionality.

Using the Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27) it is within the skill in the art to obtain other polypeptides or other DNA sequences encoding the HCMV Toledo or Towne protein from clinical isolates of HCMV. For example, the structural gene can be manipulated by varying individual nucleotides, while retaining the correct amino acid(s), or varying the nucleotides, so as to modify the amino acids, without loss of activity. Nucleotides can be substituted, inserted, or deleted by known techniques, including, for example, in vitro mutagenesis and primer repair. The structural gene can be truncated at its 3'-terminus and/or its 5'-terminus while retaining its activity. It also may be desirable to remove the region encoding the signal sequence, and/or to replace it with a heterologous sequence. It may also be desirable to ligate a portion of the HCMV Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27), particularly that which includes the amino terminal domain to a heterologous coding sequence, and thus to create a fusion peptide of HCMV Toledo or Towne.

In designing such modifications, it is expected that changes to nonconserved regions of the HCMV Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27) will have relatively smaller effects on activity, whereas changes in the conserved regions, and particularly in or near the amino terminal domain are expected to produce larger effects. Amino acid residues that are conserved between the HCMV Toledo or Towne amino acid sequences (SEQ ID NOS:2, 3, 4, 5, 7, 8, 9, 10, 11, 12, 14, 15, 17, 18, 19, 21, 22, 23, 24, 25, 26, and 27) and at least two other sequences, for example, from HCMV clinical isolates are not expected to be candidates for substitution. A residue which shows conservative variations among the HCMV sequences and at least two of the other sequences is expected to be capable of similar conservative substitution of the HCMV sequences. Similarly, a residue which varies nonconservatively among the HCMV sequences and at least three of the other sequences is expected to be capable of either conservative or nonconservative substitution. When designing substitutions to the HCMV sequences, replacement by an amino acid which is found in the comparable aligned position of one of the other sequences is especially preferred.

Additionally provided by this invention is a recombinant DNA vector comprising vector DNA and a DNA sequence encoding an HCMV Toledo polypeptide or HCMV Towne polypeptide. The vector provides the HCMV Toledo or Towne DNA in operative association with a regulatory sequence capable of directing the replication and expression of an HCMV Toledo or Towne protein in a selected host cell. Host cells transformed with such vectors for use in expressing recombinant HCMV Toledo or Towne proteins are also provided by this invention. Also provided is a novel process for producing recombinant HCMV Toledo or Towne proteins or active fragments thereof. In this process, a host cell line transformed with a vector as described above containing a DNA sequence (SEQ ID NOS:1 and 6) encoding expression of an HCMV Toledo or Towne protein in operative association with a suitable regulatory sequence capable of directing replication and controlling expression of an HCMV Toledo or Towne protein is cultured under appropriate conditions permitting expression of the recombinant DNA. The expressed protein is then harvested from the host cell or culture medium using suitable conventional means.

This novel process may employ various known cells as host cell lines for expression of the protein. Currently preferred cells are mammalian cell lines, yeast, insect and bacterial cells. Especially preferred are mammalian cell lines.

The practice of the invention will employ, unless otherwise indicated, conventional techniques of molecular biology, microbiology, recombinant DNA manipulation and production, and immunology, which are within the skill of the art. Such techniques are explained fully in the literature. See, e.g., Sambrook, *Molecular Cloning: A Laboratory Manual*, Second Edition (1989); *DNA Cloning*, Volumes I and II (D. N. Glover, Ed. 1985); *Oligonucleotide Synthesis* (M. J. Gait, Ed. 1984); *Nucleic Acid Hybridization* (B. D. Hames and S. J. Higgins, Eds. 1984); *Transcription and Translation* (B. D. Hames and S. J. Higgins, Eds. 1984); *Animal Cell Culture* (R. I. Freshney, Ed. 1986); *Immobilized Cells and Enzymes* (IRL Press, 1986); B. Perbal, *A Practical Guide to Molecular Cloning* (1984); the series, *Methods in Enzymology* (Academic Press, Inc.); *Gene Transfer Vectors for Mammalian Cells* (J. H. Miller and M. P. Calos, Eds. 1987, Cold Spring Harbor Laboratory), *Methods in Enzymology*, Volumes 154 and 155 (Wu and Grossman, and Wu, Eds., respectively), (Mayer and Walker, Eds.) (1987); *Immunochemical Methods in Cell and Molecular Biology* (Academic Press, London), Scopes, (1987); *Protein Purification: Principles and Practice*, Second Edition (Springer-Verlag, N.Y.); and *Handbook of Experimental Immunology*, Volumes I–IV (D. M. Weir and C. C. Blackwell, Eds 1986). All patents, patent applications and publications mentioned herein, both supra and infra, are hereby incorporated by reference.

Additionally provided by this invention are compositions for detecting HCMV infections in humans. These compositions comprise probes having at least one single-stranded fragment of at least 10 bases in length, more preferably 15 bases in length, of the novel Toledo sequence, and fragments hybridizing to these single-stranded fragments under stringent hybridization conditions and non-cross-hybridizing with human DNA. Additionally, these compositions comprise at least one single-stranded fragment of at least 10 bases in length, more preferably 15 bases in length, of the novel Towne sequence, and fragments hybridizing to these single-stranded fragments under stringent hybridizing with human DNA. Such probe compositions may additionally comprise a label, attached to the fragment, to provide a detectable signal, as is taught in U.S. Pat. No. 4,762,780.

Further provided by this invention are methods for detecting an HCMV infection in a human host. Such methods comprise combining under predetermined stringency conditions a clinical sample suspected of containing HCMV DNA with at least one single-stranded DNA fragment of the novel Toledo or Towne strain of HCMV having at least 10 bases, more preferably 15 bases, and being non-cross-hybridizing with human DNA, and detecting duplex formation between the single-stranded Toledo or Towne strain HCMV fragments and the sample DNA. Alternatively, PCR may be used to increase the viral nucleic acid copy number by amplification to facilitate the identification of HCMV in infected individuals. In such case, the single-stranded Toledo or Towne strain DNA sequence fragments of the present invention can be used to construct PCR primers for PCR-based amplification systems for the diagnosis of HCMV. Such systems are well known in the art. See for example, U.S. Pat. No. 5,008,182 (detection of AIDS associated virus by PCR) and Hedrum, PCR Methods and Applications 2:167–71 (1992) (detection of Chlamydia trachomatis by PCR and immunomagnetic recovery).

The DNA sequences of this invention may also be used to prepare immunizing compositions. The novel Toledo DNA sequences are recombined into the Towne strain or AD169 strain of HCMV and these recombinant viruses tested for growth properties in endothelial cells or in human tissues transplanted into SCID mice or tested in the rat eye model. Mocarski, *Proc. Nat. Acad. Sci* 90:104–08 (1993). Such recombinants will show increased immunogenicity over that shown by the Towne-125 strain currently in use in humans, without exhibiting the full virulence shown by the Toledo-i strain. Therefore, a further aspect of the invention is immunizing compositions comprising either the Towne strain or the AD169 reference strain of HCMV to which the novel Toledo DNA sequence, or analogs or fragments thereof, have been added, resulting in increased immunogenicity of the recombinant virus. The invention also includes a method for the prophylactic treatment of HCMV in humans comprising administering to a human patient an immunogenically inducing effective amount of an immunizing composition of the invention in a suitable pharmaceutical carrier. Still another aspect of the invention is a method of stimulating an immune response against CMV by administering to a patient an immunogenically inducing effective amount of an immunizing composition of the invention in a suitable pharmaceutical vehicle.

Other aspects and advantages of this invention are described in the following detailed description.

BRIEF DESCRIPTION OF THE DRAWINGS

FIG. 1 illustrates the novel Toledo DNA sequence of the invention isolated from the Toledo strain of HCMV. The arrows indicate the beginnings and ends of nucleotide sequences encoding the 21 putative amino acid sequences identified.

FIG. 2 illustrates the novel Towne DNA sequence of the invention isolated from the Towne strain of HCMV. The arrows indicate the beginnings and ends of the nucleotide sequences encoding the 4 putative amino acid sequences identified.

FIG. 3 is a schematic representation of a Southern blot of restriction enzyme digested Towne and Toledo HCMV strain DNA as detailed in Example 1. The arrow indicates a 5 kbp (kilobase pair) band of Toledo DNA on the BamHI digest that is lacking in the Towne DNA, signifying the presence of additional Toledo DNA sequence.

FIG. 4 illustrates a composite autoradiograph of the restriction enzyme digested DNA from AD169, Towne, Toledo and five clinical isolates of HCMV as described in Example 3.

FIG. 5 is a schematic presentation of the novel open reading frames identified in the novel Toledo and Towne DNA sequences.

FIG. 6 is a schematic illustration of the relative positions of novel sequences identified in Toledo genomic DNA, Towne genomic DNA in a comparison with AD169 strain genomic DNA.

DETAILED DESCRIPTION

A. Introduction

The invention provides two novel HCMV DNA sequences, termed Toledo sequence and Towne sequence, not heretofore recognized or known in the art. The invention also provides immunization compositions and methods using the novel HCMV DNA sequences of the invention and also provides other diagnostic and therapeutic uses for the sequences and their protein products. The new DNA sequences were originally found in the Toledo and Towne strains of HCMV. Details of the sequences and structural characteristics are provided in the Examples below.

Most desirably, HCMV immunogenic compositions are provided that comprise reference strain AD169 or Towne to which the novel Toledo DNA sequences, or analogs or fragments thereof, have been added in order to increase the immunogenicity of the overly-attenuated strain. Thus, one aspect of this invention includes isolated DNA and corresponding RNA sequences as disclosed in FIGS. 1 and 2 (SEQ ID NOS:6 and 1). As used herein, "isolated" means substantially free from other nucleotide or polypeptide sequences with which the subject nucleotide sequence or polypeptide sequence is typically found in its native, i.e., endogenous, state. In another aspect, the invention comprises isolated HCMV Towne or Toledo protein encoded by the respective HCMV Towne or Toledo DNA sequences (SEQ ID NOS:2, 3, 4, 5, 7, 8, 9, 10, 11, 12, 13, 14, 15, 16, 17, 18, 19, 20, 21, 22, 23, 24, 25, 26, and 27).

Another aspect of this invention includes diagnostic assays for the detection of HCMV strain variants. In brief, such diagnostic assays include the use of DNA sequence fragments of the invention as primers for amplifying HCMV related nucleic acids in a polymerase chain reaction (PCR) or by direct detection by hybridization. The diagnostic assays of the invention may also include the use of specific antibodies against the novel ORFs encoded by the Toledo or Towne DNA sequences disclosed here. Yet another aspect of the invention is the use of the novel DNA sequences modified with a unique restriction site, to act as vaccine markers.

It is anticipated that the invention will enable the production of vaccines that offer advantages over the current HCMV vaccine, which is overly attenuated and therefore not consistently effective in eliciting an immune response. More specifically, the introduction or insertion of the novel Toledo strain sequences of the present invention into the Towne strain or into the AD169 strain will result in the introduction of specific DNA sequences in the HCMV Towne genome that are not possible using the cell passage vaccines. Importantly for vaccine production, this enables precise measurement of the degree of attenuation introduced by different fragments of the DNA sequences of the invention, thereby enabling the controlled modification in the attenuation of the Towne strain that is needed in the art to correct the Towne's strain's overly attenuated characteristic and improve its function as an immunogenic composition.

B. Recombinant AD169 or Towne HCMV

Recombinant AD169 or Towne DNA is derived by co-transfecting a plasmid containing the novel Toledo sequence, or analogs or fragments thereof, and a selectable marker such as gpt or β-galactosidase in primary fibroblast cells, or other cell lines known to be permissive for growth of CMV. Recombinant viruses are selected by growth in media containing mycophenolic acid or identified by blue plaque phenotypes after applying a chromogenic substrate such as X-gal. Recombinant viruses are plaque purified and characterized by restriction enzyme analysis and Southern blotting procedures. The novel HCMV Toledo sequence, or analogs or fragments thereof, may be used unmodified with respect to the endogenous promoter and transcription termination signals. Alternatively, the HCMV Toledo strain DNA coding region can be placed under transcriptional control of a promoter such as the CMV (cytomegalovirus)

major immediate early promoter, the SV40 early promoter or some other viral or cellular promoter that generates adequate levels of expression, as discussed herein.

Modified Towne or AD169 strain HCMV is grown in tissue culture cells. For experiments with mammals, not including humans, cells such as human foreskin fibroblasts (HF) or MRC-5 cells are used to propagate the virus. The virus is harvested from cultures of these cells and the isolated recombinant virus is then be further studied for its ability to elicit an immune response and provide protection against HCMV infection.

For use in humans, the recombinant virus is produced from an FDA approved cell line in large scale amounts. Such cells include MRC-5 or WI-38 cells (both are primary human diploid fibroblasts). The recombinant virus is generated in the production cell line by transfection of viral DNA or capsids prepared from recombinant virus isolated from another cell line. The method of transfection should prevent the contamination of FDA approved cells with adventitious agents or contaminants from a non-qualified cell line. A HCMV virus produced from the above cell lines will be used to infect progressively larger flasks of tissue culture cells. Infected cells will be used as subsequent inoculums. Viable infected tissue culture cells are removed from the tissue culture vessels using trypsin and added to a 1 to 100 fold (or more) excess of uninfected cells to accomplish progressively larger inoculations. Once an optimal yield is obtained the virus will be harvested from the tissue culture cells. This process can be repeated until a large scale production is achieved. Infected cells will be removed from the tissue culture vessel and disrupted using for example, sonication, dounce homogenization or some combination of the above. The viruses are then isolated from cellular material using centrifugation techniques known in the art. Once the virus is isolated a stabilizing agent is added, such as a carbohydrate or carbohydrate derivative and the virus is then aliquoted and lyophilized.

C. Immunogenic Compositions

Immunogenic compositions can be administered to subjects to prevent HCMV infections. The immunogenic compositions prevent HCMV infections by stimulating the immune system with an attenuated virus incapable of fully manifesting the disease. A major advantage of the HCMV immunogenic compositions provided herein is that its increased degree of immunogenicity will result in move effective prevention of an HCMV infection in the population.

The Towne strain of HCMV will preferably serve as the parent strain due to its proven inability to reactivate. To make HCMV immunogenic compositions, full, truncated and/or modified novel Toledo DNA sequences are introduced into a HCMV AD169 or Towne strain virus as discussed herein. The effectiveness of the immunogenic composition in preventing HCMV infections will be measured in humans. Humans will be first inoculated with PFU's ranging from 100–20,000 PFU of mutant virus per inoculation, PFUs are measured as discussed herein. After the first inoculation, a second booster injection of similar or increased dosage usually may be given. Subjects will be exposed to wild-type HCMV after the first or second inoculation and the occurrence of CMV infections observed. Potential side effects of the vaccine will be monitored in volunteer adults previously exposed to CMV, before inoculating subjects that have not ever developed CMV infections. Attenuated virus is used without an adjuvant and with a physiologically suitable carrier.

As is known in the art and discussed herein, the novel DNA is inserted into the Towne or AD169 viral genome using, for example, homologous recombination techniques. The insertion is generally made into a gene which is non-essential in nature. Plasmid shuttle vectors that greatly facilitate the construction of recombinant viruses have been described. See, for example, Spaete and Mocarski, *Proc. Nat. Acad. Sci* 84:7213–17(1987). Expression of the polypeptide encoded by the novel Toledo DNA then occurs in cells or individuals which are immunized with the live recombinant virus.

Alternatively, the purified novel HCMV proteins may be employed in therapeutic and/or subunit immunogenic compositions for preventing and treating HCMV related conditions. Such pharmaceutical compositions comprise an immunogenically-inducing effective amount of one or more of the proteins of the present invention in admixture with a pharmaceutically acceptable carrier, for example an adjuvant/antigen presentation system such as alum. Other adjuvant/antigen presentation systems, for instance, MF59 (Chiron Corp.), QS-21 (Cambridge Biotech Corp.), 3-DMPL (3-Deacyl-Monophosphoryl Lipid A) (RibiImmunoChem Research, Inc.), clinical grade incomplete Freund's adjuvant (IFA), fusogenic liposomes, water soluble polymers or Iscoms (Immune stimulating complexes) may also be used. Other exemplary pharmaceutically acceptable carriers or solutions are aluminum hydroxide, saline and phosphate buffered saline. The composition can be systemically administered, preferably subcutaneously or intramuscularly, in the form of an acceptable subcutaneous or intramuscular solution. Also inoculation can be effected by surface scarification or by inoculation of a body cavity. The preparation of such solutions, having due regard to pH, isotonicity, stability and the like is within the skill in the art. The dosage regimen will be determined by the attending physician considering various factors known to modify the action of drugs such as for example, physical condition, body weight, sex, diet, severity of the condition, time of administration and other clinical factors. Exemplary dosage ranges comprise between about 1 μg to about 1000 μg of protein.

In practicing the method of treatment of this invention, an immunologically-inducing effective amount of protein is administered to a human patient in need of therapeutic or prophylactic treatment. An immunologically inducing effective amount of a composition of this invention is contemplated to be in the range of about 1 microgram to about 1 milligram per dose administered. The number of doses administered may vary, depending on the above mentioned factors.

D. Diagnostic Assays and Use as a Vaccine Marker

The novel Toledo and Towne DNA sequences of the present invention can be used in diagnostic assays to detect HCMV in a sample, to detect Toledo and Towne-like sequences and to detect strain differences in clinical isolates of HCMV using either chemically synthesized or recombinant Toledo or Towne DNA fragments. Additionally, the novel sequences can be used as a vaccine marker to differentiate between an individual or sample infected with or containing wild type HCMV and an individual or sample infected with or containing a HCMV vaccine, i.e., a live attenuated HCMV vaccine currently in use such as the Towne vaccine. In yet another embodiment, fragments of the DNA sequences can also be linked to secondary nucleic acids with sequences that either bind a solid support or other detection probes for use in diagnostic assays. In one aspect of the invention, fragments of the novel Toledo or Towne DNA sequences (SEQ ID NOS:1 and 3) comprising at least between 10 and 20 nucleotides can be used as primers to amplify nucleic acids using polymerase chain reaction (PCR) methods well known in the art and as probes in nucleic acid hybridization assays to detect target genetic material such as HCMV DNA in clinical specimens (with or without PCR). See for example, U.S. Pat. Nos. 4,683,202; 4,683,195; 5,091,310; 5,008,182 and 5,168,039. In an exemplary assay, a conserved region of the novel DNA sequence among virus variants is selected as the sequence to be amplified and detected in the diagnostic assay. Oligonucleotide primers at least substantially complementary to (but preferably identical with) the sequence to be amplified are constructed and a sample suspected of containing a HCMV nucleic acid sequence to be detected is treated with primers for each strand of HCMV nucleic acid sequence to be detected, four different deoxynucleotide triphosphates and a polymerization agent under appropriate hybridization conditions such that an extension product of each primer is synthesized that is complementary to the HCMV nucleic acid sequences suspected in the sample, which extension products synthesized from one primer, when separated from its complement can serve as a template for synthesis of the extension product of the other primer in a polymerase chain reaction. After amplification, the product of the PCR can be detected by the addition of a labeled probe, likewise constructed from the novel DNA sequence; capable of hybridizing with the amplified sequence as is well known in the art. See, e.g. U.S. Pat. No. 5,008,182.

In another embodiment the probes or primers can be used in a vaccine marker assay to detect a vaccine or wild type infection. Alternatively, introduction of a restriction site into the novel DNA sequence will provide a vaccine marker that can be used with PCR fragments to detect such differences in a restriction digest. Such procedures and techniques for detecting sequence variants, such as, point mutations with the expected location or configuration of the mutation, are known in the art and have been applied in the detection of sickle cell anemia, hemoglobin C disease, diabetes and other diseases and conditions as disclosed in U.S. Pat. No. 5,137,806. These methods are readily applied by one skilled in the art to detect and differentiate between wild type and vaccine infections in HCMV.

In another embodiment the novel Toledo or Towne DNA sequences can be used in their entirety or as fragments to detect the presence of DNA sequences, related sequences, or transcription products in cells, tissues, samples and the like using hybridization probe techniques known in the art or in conjunction with one of the methods discussed herein. When used as a hybridization probe, fragments of the novel DNA sequences of the invention are preferably 50–200 nucleotides long, more preferably 100–300 nucleotides long and most preferably greater than 300 nucleotides long.

E. Vectors and Chimeric Virus Production

The novel DNA sequences of the invention can be expressed in different vectors using different techniques known in the art resulting in the generation of chimeric virus. Useful and known techniques include marker transfer or homologous recombination, direct in vitro ligation, defective vector technology and amplicon generation (see, e.g., Frenkel, N. et al., *Gene Transfer and Cancer*, edited by M. L. Pearson and N. L. Sternberg (1984), Kwong, A. D. and Frenkel, *Virology* 142, 421–425 (1985); U.S. patent (Ser. No. 07/923,015 by Roizman). Vectors used in such techniques include cosmids, plasmids, and infective or defective viruses. Such vectors are known in the art. (A cosmid as used herein is a plasmid containing a lambda bacteriophage cos site. The cos site is the cis signal for packaging lambda DNA. Therefore, a cosmid, unlike a plasmid, can be packaged with high efficiency into a lambda head in vitro. This technique allows cloning of very large (30–45 kbp) fragments of DNA.) The vectors can be either single stranded or double stranded and made of either DNA or RNA.

Generally, the DNA sequence is inserted into the vector alone or linked to other HCMV genomic DNA. In direct in vitro ligation applications, the isolated sequence alone is used. In homologous recombination and marker transfer flanking nucleic acid sequences are required to effect transfer of the sequence into a HCMV viral genome. For use in viral complementation using cosmids and other vectors discussed herein the sequence (or a fragment thereof) in a vector is preferably operatively linked to at least 1 kb of HCMV genomic nucleic acid and more preferably at least 5 kb of HCMV nucleic acid. The HCMV genomic nucleic acid can be on one side or both sides of the open reading frame. If only a specific region of the open reading frame is to be used to generate a mutant virus, an open reading frame or fragment thereof is inserted into a vector.

F. Novel Toledo and Towne Protein

Another aspect of the invention includes the isolated proteins encoded by the Toledo or Towne DNA sequence as taught herein. The proteins can be used to study and modify the life cycle of HCMV because they may encode surface glycoproteins that may be immunogenic and responsible for tissue tropism or influence the immune response in an infected individual. Such proteins could therefore be used in the production of a subunit vaccine against CMV. The construction of such CMV subunits vaccine candidates is known in the art. See, for example, Spaete, *Virology* 167: 207–25 (1988).

Twenty-one novel Toledo and four novel Towne proteins have been identified by ORF analysis. The novel Toledo proteins include UL130 (SEQ ID NO:23), UL132 (SEQ ID NO:27), UL133 (SEQ ID NO:7), UL134 (SEQ ID NO:8), UL135 (SEQ ID NO:9), UL136 (SEQ ID NO:10), UL137 (SEQ ID NO:11), UL138 (SEQ ID NO:12), UL139 (SEQ ID NO:13), UL140 (SEQ ID NO:14), UL141 (SEQ ID NO:15), UL142 (SEQ ID NO:16), UL143 (SEQ ID NO:17), UL144 (SEQ ID NO:18), UL145 (SEQ ID NO:19), UL146 (SEQ ID NO:20), UL147 (SEQ ID NO:21), UL148 (SEQ ID NO:22), UL149 (SEQ ID NO:24), UL150 (SEQ ID NO:25), and/or UL151 (SEQ ID NO:26). UL130 is encoded by nucleotides 13109 through 13753, as shown in FIG. 1. UL132 is encoded by nucleotides 11673 through 12485, as shown in FIG. 1. UL133 is encoded by nucleotides 51 through 824, as shown in FIG. 1. UL134 is encoded by nucleotides 541 through 1068, as shown in FIG. 1. UL135 is encoded by nucleotides 941 through 1927, as shown in FIG. 1. UL136 is encoded by nucleotides 2018 through 2740, as shown in FIG. 1. UL137 is encoded by nucleotides 2599 through 2890, as shown in FIG. 1. UL138 is encoded by nucleotides 2823 through 3332, as shown in FIG. 1. UL139 is encoded by nucleotides 3895 through 4302, as shown in FIG. 1. UL140 is encoded by nucleotides 4484 through 4828, as shown in FIG. 1. UL141 is encoded by nucleotides 5098 through 6375, as shown in FIG. 1. UL142 is encoded by nucleotides 6448 through 7368, as shown in FIG. 1. UL143 is encoded by nucleotides 7353 through 7631, as shown in FIG. 1. UL144 is encoded by nucleotides 8008 through 8538, as shown in FIG. 1. UL145 is encoded by nucleotides 8867 through 9169, as shown in FIG. 1. UL146 is encoded by nucleotides 9450 through 9803, as shown in FIG. 1.

UL147 is encoded by nucleotides 9868 through 10347, as shown in FIG. 1. UL148 is encoded by nucleotides 10646 through 11596, as shown in FIG. 1. UL149 is encoded by nucleotides 15756 through 16124, as shown in FIG. 1. UL150 is encoded by nucleotides 15874 through 17802, as shown in FIG. 1. UL151 is encoded by nucleotides 17289 through 18299, as shown in FIG. 1.

The novel Towne proteins include UL147, UL152, UL153 and UL154 (SEQ ID NOS:2, 3, 4 and 5, respectively). UL147 is encoded by nucleotides 841 through 1321, as shown in FIG. 2. UL152 is encoded by nucleotides 1365 through 1721, as shown in FIG. 2. UL153 is encoded by nucleotides 2501 through 3337, as shown in FIG. 2. UL154 is encoded by nucleotides 3512 through 4711, as shown in FIG. 2.

"Toledo and/or Towne protein or proteins" as used herein refer to the above sequences, also enumerated in the sequence listing. "Toledo and/or Towne protein or proteins" also refers to an homologous protein from any strain or clinical isolate of HCMV, including HCMV proteins that are at least 90% homologous to the Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27). The Toledo or Towne protein can be modified to affect HCMV life cycle by deletion, insertion and substitution into the DNA sequence, as discussed herein, or by chemical synthesis of different amino acid sequence or by chemical modification. Truncated proteins can be formed by deletion of a portion of the DNA sequence or the introduction of termination signal(s) into the DNA sequence. Preferred deletions to the protein correspond to deleted amino acid sequence or sequences that contain at least one amino acid selected from the group consisting of Glu, Asp, Arg, Lys, Cys and Pro. More preferably at the deleted amino acid sequence or sequences contain at least two amino acids selected from the group consisting of Glu, Asp, Arg, Lys, Cys and Pro. More preferably the deleted amino acid sequence or sequences contain at least two prolines.

Other mutations of the protein useful in modifying HCMV life cycle include, but are not limited to, modification of cAMP phosphorylation (Arg/Lys-Arg/Lys-X-X-Asp/Glu) and/or, myristylization sites (Glycine-X1-X2-X3-Ser/Thr-X-X-Asp/Glu; where X1 is not Glu,Asp,Arg, Lys, His Pro, Phe, Tyr, Trp, where X2 is any amino acid and where X3 is not Pro), or modification of the PKC phosphorylation sites (Ser/Thr-X-Arg/Lys) and/or N-linked glycosylation sites (Asn-X-Ser/Thr; where X is not Pro).

The Toledo or Towne DNA sequences, analogs or fragments thereof can be expressed in a mammalian, insect, or microorganism host. The polynucleotide is inserted into a suitable expression vector compatible with the type of host cell employed and is operably linked to the control elements within that vector. Vector construction employs techniques which are known in the art. Site-specific DNA cleavage involved in such construction is performed by treating with suitable restriction enzymes under conditions which generally are specified by the manufacturer of these commercially available enzymes. A suitable expression vector is one that is compatible with the desired function (e.g., transient expression, long term expression, integration, replication, amplification) and in which the control elements are compatible with the host cell.

Mammalian Cell Expression

Vectors suitable for replication in mammalian cells are known in the art, and can include viral replicons, or sequences that ensure integration of the sequence encoding the Toledo or Towne DNA into the host genome. Exemplary vectors include those-derived from SV40, retroviruses, bovine papilloma virus, vaccinia virus, other herpesviruses and adenovirus.

Such suitable mammalian expression vectors contain a promoter to mediate transcription of foreign DNA sequences and, optionally, an enhancer. Suitable promoters are known in the art and include viral promoters such as those from SV40, cytomegalovirus (CMV), Rous sarcoma virus (RSV), adenovirus (ADV), and bovine papilloma virus (BPV).

The optional presence of an enhancer, combined with the promoter described above, will typically increase expression levels. An enhancer is any regulatory DNA sequence that can stimulate transcription up to 1000-fold when linked to endogenous or heterologous promoters, with synthesis beginning at the normal mRNA start site. Enhancers are also active when placed upstream or downstream from the transcription initiation site, in either normal or flipped orientation, or at a distance of more than 1000 nucleotides from the promoter. See Maniatis, *Science* 236:1237 (1987), Alberts, *Molecular Biology of the Cell,* 2nd Ed. (1989). Enhancers derived from viruses may be particularly useful, because they typically have a broader host range. Examples include the SV40 early gene enhancer (see Dijkema, *EMBO J.* 4:761 (1985)) and the enhancer/promoters derived from the long terminal repeat (LTR) of the RSV (see Gorman, *Proc. Natl. Acad. Sci.* 79:6777 (1982b)) and from human cytomegalovirus (see Boshart, *Cell* 41:521 (1985)). Additionally, some enhancers are regulatable and become active only in the presence of an inducer, such as a hormone or metal ion (see Sassone-Corsi and Borelli, *Trends Genet.* 2:215 (1986)); Maniatis, *Science* 236:1237 (1987)). In addition, the expression vector can and will typically also include a termination sequence and poly(A) addition sequences which are operably linked to the Toledo or Towne coding sequence.

Sequences that cause amplification of the gene may also be desirably included in the expression vector or in another vector that is co-translated with the expression vector containing a Towne or Toledo DNA sequence, as are sequences which encode selectable markers. Selectable markers for mammalian cells are known in the art, and include for example, thymidine kinase, dihydrofolate reductase (together with methotrexate as a DHFR amplifier), aminoglycoside phosphotransferase, hygromycin B phosphotransferase, asparagine synthetase, adenosine deaminase, metallothionien, and antibiotic resistant genes such as neomycin.

The vector that encodes a novel Toledo or Towne protein or polypeptide of this invention can be used for transformation of a suitable mammalian host cell. Transformation can be by any known method for introducing polynucleotide into a host cell, including, for example packaging the polynucleotide in a virus and transducing a host cell with the virus. The transformation procedure used depends upon the host to be transformed. Methods for introduction of heterologous polynucleotide into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines.

Insect Cell Expression

The components of an insect cell expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media. Exemplary transfer vectors for introducing foreign genes into insect cells include pAc373 and pVL985. See Luckow and Summers, *Virology* 17:31 (1989).

The plasmid can also contains the polyhedron polyadenylation signal and a procaryotic ampicillin-resistance (amp) gene and origin of replication for selection and propagation in *E. coli*. See Miller, *Ann. Rev. Microbiol.* 42:177 (1988).

Baculovirus transfer vectors usually contain a baculovirus promoter, i.e., a DNA sequence capable of binding a baculovirus RNA polymerase and initiating the downstream (5' to 3') transcription of a coding sequence (e.g., structural gene) into mRNA. The promoter will have a transcription initiation region which is usually placed proximal to the 5' end of the coding sequence and typically includes an RNA polymerase binding site and a transcription initiation site. A baculovirus transfer vector can also have an enhancer, which, if present, is usually distal to the structural gene. Expression can be either regulated or constitutive.

Yeast And Bacteria Expression

A yeast expression system can typically include one or more of the following: a promoter sequence, fusion partner sequence, leader sequence, transcription termination sequence. A yeast promoter, capable of binding yeast RNA polymerase and initiating the downstream (3') transcription of a coding sequence (e.g. structural gene) into mRNA, will have a transcription initiation region usually placed proximal to the 5' end of the coding sequence. This transcription initiation region typically includes an RNA polymerase binding site (a "TATA Box") and a transcription initiation site. The yeast promoter can also have an upstream activator sequence, usually distal to the structural gene. The activator sequence permits inducible expression of the desired heterologous DNA sequence. Constitutive expression occurs in the absence of an activator sequence. Regulated expression can be either positive or negative, thereby either enhancing or reducing transcription.

Particularly useful yeast promoters include alcohol dehydrogenase (ADH) (EP Patent Pub. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK)(EP Patent Pub. No. 329 203). The yeast PHO5 gene, encoding acid phosphatase, also provides useful promoter sequences. See Myanohara, *Proc. Natl. Acad. Sci. USA* 80:1 (1983).

A Toledo or Towne DNA sequence, analog or an active fragment thereof can be expressed intracellularly in yeast. A promoter sequence can be directly linked with the sequence or fragment, in which case the first amino acid at the N-terminus of the recombinant protein will always be a methionine, which is encoded by the ATG start codon. If desired, methionine at the N-terminus can be cleaved from the protein by in vitro incubation with cyanogen bromide.

Intracellularly expressed fusion proteins provide an alternative to direct expression of a sequence. Typically, a DNA sequence encoding the N-terminal portion of a stable protein, a fusion partner, is fused to the 5' end of heterologous DNA encoding the desired polypeptide. Upon expression, this construct will provide a fusion of the two amino acid sequences. For example, the yeast or human superoxide dismutase (SOD) gene, can be linked at the 5' terminus of a sequence and expressed in yeast. The DNA sequence at the junction of the two amino acid sequences may or may not encode a clearable site. See, e.g., EP Patent Pub. No. 196 056. Alternatively, the polypeptides can also be secreted from the cell into the growth media by creating a fusion protein comprised of a leader sequence fragment that provides for secretion in yeast or bacteria of the polypeptides. Preferably, there are processing sites encoded between the leader fragment and the sequence that can be cleaved either in vivo or in vitro. The leader sequence fragment typically encodes a signal peptide comprised of hydrophobic amino acids which direct the secretion of the protein from the cell. DNA encoding suitable signal sequences can be derived from genes for secreted yeast proteins, such as the yeast invertase gene (EP Patent Pub. No. 12 873) and the A-factor gene (U.S. Pat. No. 4,588,684). Alternatively, leaders of non-yeast origin, such as an interferon leader, can be used to provide for secretion in yeast (EP Patent Pub. No. 60057). Transcription termination sequences recognized by yeast are regulatory regions located 3' to the translation stop codon. Together with the promoter they flank the desired heterologous coding sequence. These flanking sequences direct the transcription of an mRNA which can be translated into the polypeptide encoded by the DNA.

Typically, the above described components, comprising a promoter, leader (if desired), coding sequence of interest, and transcription termination sequence, are put together in plasmids capable of stable maintenance in a host, such as yeast or bacteria. The plasmid can have two replication systems, so it can be maintained as a shuttle vector, for example, in yeast for expression and in a procaryotic host for cloning and amplification. Examples of such yeast-bacteria shuttle vectors include YEp24 (see Botstein, *Gene* 8:17–24 (1979)), pCl/1 (see Brake, *Proc. Natl. Acad. Sci. USA* 81:46424646 (1984)), and YRp17 (see Stinchcomb, *J. Mol. Biol.* 158:157 (1982)). In addition, the plasmid can be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20. Either a high or low copy number vector may be selected, depending upon the effect on the host of the vector and the polypeptides. See, e.g., Brake, et al., supra.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. See Orr-Weaver, *Methods in Enzymol.* 101:228–245 (1983) and Rine, *Proc. Natl. Acad. Sci. USA* 80:6750 (1983).

Typically, extrachromosomal and integrating expression vectors can contain selectable markers to allow for the selection of yeast strains that have been transformed. Selectable markers can include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker can also provide yeast with the ability to grow in the presence of toxic compounds, such as metal. For example, the presence of CUP1 allows yeast to grow in the presence of copper ions. See Butt, *Microbiol. Rev.* 51:351 (1987).

Alternatively, some of the above described components can be put together into transformation vectors. Transformation vectors are typically comprised of a selectable marker that is either maintained in a replicon or developed into an integrating vector, as described above. Expression and transformation vectors, either extrachromosomal or integrating, have been developed for transformation into many yeasts. Exemplary yeasts cell lines are *Candida albicans* (Kurtz, *Mol. Cell. Biol.* 6:142 (1986), *Candida maltosa* (Kunze, *J. Basic Microbiol.* 25:141 (1985), *Hansenula polymorpha* (Gleeson, *J. Gen. Microbiol.* 132:3459 (1986) and Roggenkamp, *Mol. Gen. Genet.* 202:302 (1986), *Kluyveromyces fragilis* (Das, *J. Bacteriol.* 158:1165 (1984), *Kluyveromyces lactis* (De Louvencourt, *J. Bacteriol.* 154: 737 (1983) and Van den Berg, *Bio/Technology* 8:135 (1990), *Pichia guillerimondii* (Kunze, *J. Basic Microbiol.* 25:141 (1985), *Pichia pastoris* (Cregg, *Mol. Cell. Biol.* 5:3376 (1985), *Saccharomyces cerevisiae* (Hinnen, *Proc. Natl. Acad. Sci. USA* 75:1929 (1978) and Ito, *J. Bacteriol.* 153: 163 (1983), *Schizosaccharomyces pombe* (Beach and Nurse, *Nature* 300:706 (1981), and *Yarrowia lipolytica* (Davidow, *Curr. Genet.* 10:380471 (1985) and Gaillardin, *Curr. Genet.* 10:49 (1985).

Methods of introducing exogenous DNA into yeast hosts are well-known in the art, and typically include either the transformation of spheroplasts or of intact yeast cells treated with alkali cations. Transformation procedures usually vary with the yeast species to be transformed. See the publications listed in the foregoing paragraph for appropriate transformation techniques.

Additionally, the gene or fragment thereof can be expressed in a bacterial system. In such system, a bacterial promoter is any DNA sequence capable of binding bacterial RNA polymerase and initiating the downstream (3') transcription of a coding sequence (e.g. a desired heterologous gene) into MRNA. A promoter will have a transcription initiation region which is usually placed proximal to the 5' end of the coding sequence. This transcription initiation region typically includes an RNA polymerase binding site and a transcription initiation site. A bacterial promoter can also have a second domain called an operator, that can overlap an adjacent RNA polymerase binding site at which RNA synthesis begins. The operator permits negative regulated (inducible) transcription, as a gene repressor protein can bind the operator and thereby inhibit transcription of a specific gene. Constitutive expression can occur in the absence of negative regulatory elements, such as the operator. In addition, positive regulation can be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*). See Raibaud, *Ann. Rev. Genet.* 18:173 (1984). Regulated expression can therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (ac) (see Chang, *Nature* 198:1056 (1977), and maltose. Additional examples include promoter sequences derived from biosynthetic enzymes such as tryptophan (trp) (see Goeddel, *Nuc. Acids Res.* 8:4057 (1981), Yelverton, *Nuc. Acids Res.* 9:731 (1981), U.S. Pat. No. 4,738,921 and EP Patent Pub. Nos. 36 776 and 121 775). The lactomase (bla) promoter system (see Weissmann, *Interferon* 3 (ed. I. Gresser), the bacteriophage lambda PL promoter system (see Shimatake, *Nature* 292: 128 (128) and the T5 promoter system (U.S. Pat. No. 4,689,406) also provides useful promoter sequences.

In addition, synthetic promoters which do not occur in nature also function as bacterial promoters. For example, transcription activation sequences of one bacterial or bacteriophage promoter can be joined with the operon sequences of another bacterial or bacteriophage promoter, creating a synthetic hybrid promoter such as the tac promoter (see U.S. Pat. No. 4,551,433, Amann, *Gene* 25:167 (1983) and de Boer, *Proc. Natl. Acad. Sci.* 80:21 (1983)). A bacterial promoter can include naturally occurring promoters of non-bacterial origin that have the ability to bind bacterial RNA polymerase and initiate transcription. A naturally occurring promoter of non-bacterial origin can be coupled with a compatible RNA polymerase to produce high levels of expression of some genes in prokaryotes. The bacteriophage T7 RNA polymerase/promoter system is exemplary. (see Studier, *J. Mol. Biol.* 189:113 (1986) and Tabor, *Proc. Natl. Acad. Sci.* 82:1074 (1985)).

In addition to a functioning promoter sequence, an efficient ribosome binding site is also useful for the expression of the DNA sequence or fragment thereof in prokaryotes. In *E. coli*, the ribosome binding site is called the Shine-Dalgarno (SD) sequence and includes an initiation codon (ATG) and a sequence 3–9 nucleotides in length located 3–11 nucleotides upstream of the initiation codon (see Shine, *Nature* 254:34 (1975). The SD sequence is thought to promote binding of MRNA to the ribosome by the pairing of bases between the SD sequence and the 3' and of *E. coli* 16S rRNA (see Steitz, *Biological Regulation and Development: Gene Expression* (ed. R. F. Goldberger)(1979)).

The novel Toledo or Towne proteins of the invention can be expressed intracellularly. A promoter sequence can be directly linked with a novel Toledo or Towne DNA sequence, analog or a fragment thereof, in which case the first amino acid at the N-terminus will always be a methionine, which is encoded by the ATG start codon. If desired, methionine at the N-terminus can be cleaved from the protein by in vitro incubation with cyanogen bromide or by either in vivo on in vitro incubation with a bacterial methionine N-terminal peptidase. See EP Patent Pub. No. 219 237.

Fusion proteins provide an alternative to direct expression. Typically, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of an sequence fragment thereof and expressed in bacteria. The resulting fusion protein preferably retains a site for a processing enzyme (factor Xa) to cleave the bacteriophage protein from the sequence or fragment thereof (see Nagai, *Nature* 309:810 (1984). Fusion proteins can also be made with sequences from the lacZ gene (Jia, *Gene* 60:197 (1987),the trpE gene (Allen, *J. Biotechnol.* 5:93 (1987) and Makoff, *J. Gen. Microbiol.* 135:11 (1989), and the Chey gene (EP Patent Pub. No. 324 647) genes. The DNA sequence at the junction of the two amino acid sequences may or may not encode a clearable site. Another example is a ubiquitin fusion protein. Such a fusion protein is made with the ubiquitin region that preferably retains a site for a processing enzyme (e.g., ubiquitin specific processing-protease) to cleave the ubiquitin from the polypeptide. Through this method, mature Towne or Toledo polypeptides can be isolated. See Miller, *Bio/Technology* 7:698 (1989).

Alternatively, proteins or polypeptides can also be secreted from the cell by creating chimeric DNA molecules that encode a fusion protein comprised of a signal peptide sequence fragment that provides for secretion of the proteins or polypeptides in bacteria. (See, for example, U.S. Pat. No. 4,336,336). The signal sequence fragment typically encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the protein or polypeptide.

DNA encoding suitable signal sequences can be derived from genes for secreted bacterial proteins, such as the *E. coli* outer membrane protein gene (ompA) (Masui, Experimental Manipulation of Gene Expression (1983) and Ghrayeb, *EMBO J.* 3:2437 (1984)) and the *E. coli* alkaline phosphatase signal sequence (phoA) (see Oka, *Proc. Natl. Acad. Sci.* 82:7212 (1985). The signal sequence of the alpha-amylase gene from various *Bacilus* strains can be used to secrete heterologous proteins from *B. subtilis* (see Palva, *Proc. Natl. Acad. Sci.* 79:5582 (1982) and EP Patent Pub. No. 244 042).

Transcription termination sequences recognized by bacteria are regulatory regions located 3' to the translation stop codon. Together with the promoter they flank the coding sequence. These sequences direct the transcription of an mRNA which can be translated into the Towne or Toledo protein or polypeptide encoded by the DNA sequence. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Typically, the promoter, signal sequence (if desired), coding sequence of interest, and transcription termination sequence are maintained in an extrachromosomal element (e.g., a plasmid) capable of stable maintenance in the bacterial host. The plasmid will have a replication system, thus allowing it to be maintained in the bacterial host either for expression or for cloning and amplification. In addition, the plasmid can be either a high or low copy number plasmid. A high copy number plasmid will generally have a copy number ranging from about 5 to about 200, and typically about 10 to about 150. A host containing a high copy number plasmid will preferably contain at least about 10, and more preferably at least about 20 plasmids.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. See e.g., EP Patent Pub. No. 127 328.

Typically, extrachromosomal and integrating expression constructs can contain selectable markers to allow for the selection of bacterial strains that have been transformed. Selectable markers can be expressed in the bacterial host and can include genes which render bacteria resistant to drugs such as ampicillin, chloramphenicol, erythromycin, kanamycin (neomycin), and tetracycline (see Davies, *Ann. Rev. Microbiol.* 32:469 (1978). Selectable markers can also include biosynthetic genes, such as those in the histidine, tryptophan, and leucine biosynthetic pathways.

Alternatively, some of the above described components can be put together in transformation vectors. Transformation vectors are typically comprised of a selectable marker that is either maintained in an extrachromosal vector or an integrating vector, as described above.

Expression and transformation vectors, either extra-chromosomal or integrating, have been developed for transformation into many bacteria. Exemplary are the expression vectors disclosed in Palva, *Proc. Natl. Acad. Sci.* 79:5582 (1982), EP Patent Pub. Nos. 036 259 and 063 953 and PCT Patent Publication WO 84/04541 (for *B.subtilis*); in Shimatake, *Nature* 292:128 (1981), Amann, *Gene* 40:183 (1985), Studier, *J. Mol. Biol.* 189:113 (1986) and EP Patent Pub. Nos. 036 776, 136 829 and 136 907 (for *E. coli*); in Powell, *Appl. Environ. Microbiol.* 54:655 (1988) and U.S. Pat. No. 4,745,056 (for *Streptococcus*).

Methods of introducing exogenous DNA into bacterial hosts are well-known in the art, and typically include either the transformation of bacteria treated with $CaCl_2$ or other agents, such as divalent cations and DMSO. DNA can also be introduced into bacterial cells by electroporation. Exemplary methodologies can be found in Masson, *FEMS Microbiol. Let.* 60:273 (1989), Palva, *Proc. Natl. Acad. Sci.* 79:5582 (1982), EP Patent Pub. Nos. 036 259 and 063 953 and PCT Patent Pub. WO 84/04541 for *Bacillus* transformation. For campylobacter transformation, see e.g., Miller, *Proc. Natl. Acad. Sci.* 85:856 (1988) and Wang, *J. Bacteriol.* 172:949 (1990). For *E. coli*, see e.g., Cohen, *Proc. Natl. Acad. Sci.* 69:2110 (1973), Dower, *Nuc. Acids Res.* 16:6127 (1988), Kushner, *Genetic Engineering: Proceedings of the International Symposium on Genetic Engineering* (eds. H. W. Boyer and S. Nicosia), Mandel, *J. Mol. Biol.* 53:159 (1970) and Taketo, *Biochem. Biophys. Acta* 949:318 (1988). For *Lactobacillus* and *Pseudomonas*, see e.g., Chassy, *FEMS Microbiol. Let.* 44:173 (1987) and Fiedler, *Anal. Biochem.* 170:38 (1988), respectively. For *Streptococcus*, see e.g., Augustin, *FEMS Microbiol. Let.* 66:203 (1990), Barany, *J. Bacteriol.* 144:698 (1980), Harlander, *Streptococcal Genetics* (ed. J. Ferretti and R. Curtiss III)(1987), Perry, *Infec. Immun.* 32:1295 (1981), Powell, *Appl. Environ. Microbiol.* 54:655 (1988) and Somkuti, *Proc. 4th Evr. Cong. Biotechnology* 1:412 (1987).

The present invention is illustrated by the following examples.

MATERIALS AND METHODS

A. Cells and Virus

Human CMV strains AD169, Towne and Toledo were obtained from E. S. Mocarski (Stanford University) and were used for all experiments. Two of these strains are also available through the ATCC, Accession Nos. VR-538 (AD169) and VR-977 (Towne). Virus was grown in cultures of human foreskin fibroblast (HF) cells with Dulbecco's modified Eagle's medium (DME) (JRH Biosciences, Lenexa, Kans.) as previously described in Spaete and Mocarski, *J. Virol* 56:135–43 (1985), but supplemented with 10% fetal calf serum (FCS) (JRH Biosciences, Lenexa, Kans.), L-glutamine (2 mM), penicillin (100 units/ml), streptomycin (0.1 mg/ml) and pyruvate (1 mM). To prepare AD169, Towne and Toledo strain CMV DNAs by centrifugation to equilibrium on NaI gradients as previously described in Spaete and Mocarski, *J. Virol* 54:817–24 (1985), roller bottles were infected with the CMV strains at a multiplicity of infection (MOI) of 0.001 plaque forming units (pfu)/cell to minimize the production of defective virus particles. The infected cells were refed at four days post infection with medium. At eight days post infection when the monolayer was well infected, cells were scraped into a 50 ml conical tube in 10 mls media per roller bottle and pelleted at 1000 revolutions per minute (rpm) for 10 minutes. Pellets were resuspended in 2.0 ml 0.01 M Tris and 0.01 EDTA (TE) (pH 7.4) with 1% NP40, 1% deoxycholate and incubated on ice until all cellular nuclei were lysed when viewed under a microscope. Lysates were transferred to a 2059 tube (Falcon) and spun at 2600 rpm for 5 minutes at 4° C. Supernatants were transferred to another 2059 tube and RNAse (Worthington-DNase free) was added at 50 µg/ml followed immediately by Proteinase K (200 µg/ml) and 1% sodium dodecyl sulfate (SDS). Supernatants were incubated in a 65° C. water bath for 60 minutes, brought to 16 ml with TE, pH 7.4, added to 24 mls of saturated NaI and 0.15 ml ethidium bromide (5 mg/ml). Samples were centrifuged to equilibrium at 55,000 rpm at 20° C. for 24 hours in a Beckman Ti70 rotor. Fractions containing the viral DNA were extracted with butanol equilibrated with TE with gentle rocking followed by centrifugation at 3,000 rpm for 10 min at 20° C. and further extracted 2 to 3 times with butanol to reduce volume. Samples were extracted with an equal volume of isoamyl alcohol equilibrated with TE, spun and re-extracted. DNA was dialyzed against three changes of TE with 1% phenol and 1M NaCl. The $OD_{260}$ and $OD_{280}$ were read to determine purity of the AD169, Toledo and Towne DNA.

Clinical isolates were obtained from M. Fiala (Rancho Mirage, Calif.), and S. Chou (Oregon Health Sciences University). Rapid isolation of HCMV infected cell viral DNA was carried out as previously described in Spaete and Frenkel, Cell 30:295–304 (1982), except that DNA was not radiolabeled before purification. Briefly, infected cell monolayers (25 cm² flasks) were rinsed twice with phosphate-buffered saline (PBS) and lysed in a 1.0 ml solution of 0.1 M NaCl, TE, pH 8.0, 0.05% SDS and 0.1 mg/ml Proteinase K. Lysates were incubated 2–24 hours at 37° C., extracted twice with 1 volume of phenol, 1 volume of chloroform followed by centrifugation at 2500 rpm for 5 minutes to separate phases. The aqueous phase was extracted twice with 1 volume of ether and the DNA was precipitated with 0.1 volume 3M NaAC and two volumes of ethanol or isopropanol. DNA was chilled, collected by centrifugation or spooled on a glass rod, dried and resuspended in TE.

B. Plasmid DNA

Plasmids pXbaI E, pXbaI T and pXbaI Q (Thomsen and Stinski, 1981), representing Towne strain map units 0.69 to 0.8, were obtained from M. Stinski (University of Iowa).

Clone 65 was derived by cloning a gel extracted BamHI digested Toledo DNA fragment into the BamHI site of plasmid, pGEM®-3Zf+ (Promega, Madison, Wis.). Briefly, five µg of Toledo DNA was digested with 40 units of BamHI and electrophoresed in a preparative 1% low-melting-point agarose gel for 490 volt hours in 1X TAE buffer. Toledo DNA migrating at ca. 5 kilobase pairs (kbp) was excised and the agarose was digested with 2 units of β-agarase I (New England BioLabs, Beverly, Mass.). This DNA fragment was precipitated with 2 volumes of isopropanol, chilled to −20° C., spun in an Eppendorf centrifuge for 15 minutes, dried and resuspended in 50 µl TE. The gel extracted fragment was ligated to BamHI digested pGEM®-3Zf+ using T4 DNA ligase (New England BioLabs, Berverly, Mass.), and an aliquot of the ligation mixture was used to transform competent Escherichia coli XL-1 Blues (Stratagene, La Jolla, Calif.) by the calcium shock method (Mandel and Higa, 1970), or by electroporation using methods as written in the Pulse Controller Guide published by BioRad (Richmond, Calif.).

Cosmid 1 is a ca. 53 kbp partially digested HindIII fragment of Toledo DNA spanning 0.69 to 0.87 map units cloned into cosmid pHC79 (Hohn and Collins, 1980) obtained from E. S. Mocarski (Stanford University). Subcloned from cosmid 1 were the following:

Clones 4 and C1300 were derived by cloning BamH1 digested fragments from Cosmid 1 cloned into a Bluescript M13+ plasmid vector. As such, these clones represent Toledo DNA sequence spanning portions of Cosmid 1.

Clone C23K was derived as a complete BamH1 digested fragment of Cosmid 1 DNA and circularized by ligation.

C. Preparation of Radioactively Labeled Probes and Hybridization.

Plasmid or viral DNA was radioactively labeled in vitro by nick translation (Rigby et al., 1977) with a kit (Boehringer Mannheim), and using [$\alpha^{32}$P]dCTP (Amersham Corp.). Hybridizations to immobilized CMV DNA were performed essentially as described by Spaete and Mocarski, J. Virol 54:817–24 (1985), but at 68° C. in a solution of 6xSSC (1xSSC is 0.15 M NaCl plus 0.015 M sodium citrate), 0.2% polyvinylpyrrolidone, 0.2% Ficoll, 0.2% bovine serum albumin, and 0.1% sodium dodecyl sulfate, with the amount of salmon sperm DNA being changed from 25 µg/ml to 100 µg/ml and 30% formamide being reduced to 15%.

DNA was transferred to Hybond-N+ nylon transfer membranes (Amersham Corp.), after restriction enzyme digestion and electrophoresis in 1% agarose gels by standard techniques (Maniatis et al., 1982). DNA was cross-linked to the membrane with 120,000 microjoules/cm² of UV irradiation using a UV Crosslinker 1000 (Hoefer Scientific Instruments, San Francisco, Calif.). Membranes were prehybridized 1 hour at 68° C. in solution A (6xSSC, 0.2% polyvinylpyrrolidone, 0.2% Ficoll, 0.2% bovine serum albumin, 0.1% sodium dodecyl sulfate, 100 µg/ml salmon sperm DNA and 15% formamide), then nick-translated [$\alpha^{32}$P]-labeled probe in a solution containing 100 µg/ml salmon sperm DNA was denatured by boiling for five minutes, snap-cooled on ice, added to the membrane and allowed to hybridize overnight at 68° C. After hybridization, unannealed probe was removed by rinsing the membrane 3x with 2xSSC followed by reincubation in solution A lacking salmon sperm DNA at 68° C. for 15 minutes. The washing procedure was repeated, the blot was rinsed in a large volume of 2xSSC at room temperature, the membrane was air dried and autoradiographed using Kodak X-AR film.

D. Nucleotide Sequence Determination and Analysis.

All nucleic acid sequences were determined by the dideoxynucleotide chain termination method (Sanger et al., 1977). A variety of templates were prepared for sequencing; they included single-stranded phage DNA, double-stranded plasmid and cosmid DNA, viral genomic DNA, and PCR products. Manual and automated sequencing (with an ABI 373A instrument) were employed. Both one-cycle and multi-cycle sequencing protocols were used. The sequence was determined for both strands. Ambiguous regions were corrected by additional sequencing after proofreading. The primers used for sequencing were synthesized on an ABI 392 instrument (Applied Biosystems). The contig and analysis of the sequence were performed using MacDNASIS (Hitachi). The homology searches were performed using the BLAST program through NCBI services.

EXAMPLE 1

Identification of Novel Sequences in the Genomes of CMV Towne and Toledo Strain Isolates.

To determine the cross representation of DNA sequences in the Towne and Toledo strains of CMV, viral DNA from each strain was digested to completion with XbaI, ClaI, BamHI, BglII, EcoRI, and HindIII. After electrophoresis through a 1% agarose gel, the CMV DNAs were denatured in 0.2M NaCl/0.6M NaOH, neutralized in 0.6M NaCl/1M Tris, pH 7.5, in situ, and the gel was soaked in 20×SSC for 30 minutes. Stereo blots were prepared by placing identically sized Hybond-N+ nylon membranes (Amersham Corp.), on either side of the gel and transferring the DNAs to the membranes in both directions using the capillary action of paper towels. After blotting overnight in 20×SSC, the membranes were washed in 2×SSC and the DNA was immobilized on the membrane by UV irradiation as described above.

DNA probes of Towne and Toledo DNA with an average size of 500 bp were prepared by sonicating 10 µg of each DNA in a 2063 tube (Falcon Plastics) using 4 pulses of 10 seconds each at a setting of 3 on a Heat Systems, Inc. sonicator (Farmingdale, N.Y.). Following sonication, the viral DNAs were digested with the restriction enzymes AvaI, BanI and BfaI, to further reduce the size complexity of the probe DNA. These enzymes were chosen because a search of the AD169 DNA database sequences (EMBL accession number X17403), revealed abundant cut sites (326, 386, and 341, respectively); their restriction enzyme digestion buffers are compatible; and their sites do not overlap. Ethidium bromide stained gels of the sheared viral DNAs prepared in this manner revealed a range of DNA sizes from 1300 bp to less than 100 bp, with the majority of DNA migrating at approximately 300 bp as judged by comigration with a HaeIII digested ØX174 DNA standard marker (New England BioLabs, Beverly, Mass.). The Towne and Toledo sheared probe DNA was then nick translated using [$\alpha^{32}P$] dCTP (Amersham Corp.) as described above and each probe was applied to stereo blots of immobilized, restriction enzyme digested, Towne and Toledo DNAs. After hybridization and autoradiography, the hybridization patterns were analyzed to determine the fragments on each DNA profile which did not hybridize with the heterologous strain probe but did hybridize with the homologous strain probe. For example, the loss of a signal for a prominent 5 kbp band on the BamHI digest of Toledo DNA when using the Towne probe, which was present when the Toledo DNA was used to probe itself, revealed a region of sequence divergence between the two isolates (see FIG. 3).

This 5 kbp fragment was cloned by gel extraction as described above and designated clone 65. The clone 65 Toledo DNA was sequenced in its entirety and compared to Towne DNA sequence generated from the pXbaI T clone which was shown to be divergent from AD169 DNA sequences (see Example 2 below). The full sequence of clone 65 is shown in FIG. 1. In FIG. 1, Clone 65 begins with nucleotide 4664 and ends with nucleotide 9327. Surprisingly, the DNA from the pXbaI T clone of Towne DNA (1,856 bp) and clone 65 of Toledo DNA (4,668 bp) shared 104 bp of sequence identity. This small stretch of sequence homology allowed mapping of the region of Toledo DNA divergence to the boundary of the Unique Long ($U_L$) component and the inverted repeats (alternatively termed IRL or b' sequences) on the AD169 and Towne DNA maps. These newly isolated Toledo strain nucleotide sequences from clone 65 were not represented in the reference laboratory strain, AD169, which has been sequenced in its entirety by Chee and colleagues (EMBL accession number X17403).

EXAMPLE 2

Identification of Novel Sequences in the Genome of CMV Towne not Found in Reference Strain AD169.

DNA sequence heterogeneity between the Towne strain and the AD169 strain has been found. See, Pritchett, *J. Virology* 36:152–61 (1980). However, although the gross structural organization of the CMV genome has been determined and strain to strain restriction site polymorphisms have been mapped for many strains, strain-to-strain differences on the nucleotide level have not been determined. The laboratory strain AD169 was the first CMV isolate to be sequenced and has served as the reference strain in defining the genetic complexity of the CMV genome.

In order to examine nucleotide sequence differences between Towne and AD169, we focused on the region shown to be divergent in the Toledo strain, i.e. the boundary between the $U_L$ component and the b' sequences, as explained in detail in Example 1. Plasmid pXbaI T was labeled using the NEBlot™ Phototope™ Detection Kit (New England Biolabs, Beverly, Mass.), and used as a probe on blots of immobilized restriction enzyme digested Towne, Toledo and AD169 DNAs. Briefly, pXbaI T was linearized with PvuII, ethanol precipitated and resuspended in 34 µl of nuclease free water. The plasmid was denatured in boiling water for five minutes, snap cooled on ice for five minutes and centrifuged briefly at 4° C. The following reagents were added to the tube in the order listed: 10 µl of 5× labeling mix, 5 µl of dNTP mix, 1 µl of DNA polymerase I (Klenow fragment). The mix was incubated at 37° C. for 6 hours and the reaction was terminated by adding 5 µl of 0.2 M EDTA, pH 8.0. The probe was precipitated by adding 5 µl of 4M LiCl and 150 µl of ethanol, chilling to −80° C. for 30 minutes, pelleted in an Eppendorf centrifuge, washed with 70% ethanol and resuspended in 20 µl of Resuspension Buffer as supplied by the kit. The hybridization reaction was essentially as described above except that after hybridization the membrane was washed twice in 2×SSC, 0.1% SDS at room temperature for 5 minutes each followed by two washes in 0.1×SSC, 0.1% SDS at 68° C. for 15 minutes. The detection reactions link the biotinylated probes to alkaline phosphatase through a strepavidin bridge and the hybridized probe was visualized by cleavage of the Lumigen-PPD substrate. The blocking steps, strepavidin incubation, alkaline phosphatase incubation and Lumigen-PPD reaction were carried out as described in the kit manual. Exposure of the blots to Kodak XAR film revealed that, as expected, (i) an XbaI digested fragment of sized 1.85 kbp (XbaI T) was hybridized on Towne DNA probed with pXbaI T and (ii) a comigrating XbaI digested fragment was present in Toledo DNA. The AD169 DNA failed to show any hybridization signal on any of the restriction enzyme digestion patterns. Nucleotide sequence of pXbaI T confirmed the total lack of identity of the Towne DNA and AD169 DNA. Nucleotide sequencing of cosmid 1 DNA (see B. Plasmid DNA in Material and Methods, above) from Toledo revealed extensive sequence identity between the newly identified Towne DNA and the Toledo DNA of cosmid 1 in this region. Surprisingly, the orientation of the sequence was reversed in Toledo relative to Towne.

EXAMPLE 3

Identification of Novel Toledo DNA Sequences in the Genomes of Recent Clinical Isolates and not Found in Reference Strain AD169.

To determine the penetrance of sequences represented by clone 65 in recent clinical isolates, five representative clinical isolates (HCMVF, C128, C354, C793 and C980) were digested with restriction enzymes BamHI and XbaI along with the Toledo, Towne and AD169 DNAs prepared as described in the Materials and Methods section above, electrophoresed through agarose, transferred to a Hybond-N+ nylon transfer membrane, and probed with nick-translated [$\alpha^{32}$P]-labeled clone 65 according to the procedures outlined in the Materials and Methods section. As can be seen in FIG. 4, the autoradiographs revealed that homology was detected in all of the clinical isolates. In FIG. 4, a band at ca. 5 kbp is visible in lane 1 (the Toledo DNA), appears in Towne DNA (lane 2), is missing from lane 3 (the AD 169 DNA), and visible in lanes 4 through 8 (the clinical isolates HCMVF, C128, C354, C793 and C980). These results demonstrate that the newly isolated sequence found in the Toledo strain of HCMV is also present in the recent clinical isolates but is not present in the AD169 reference strain. Nucleotide sequence analysis reveals the reason for the weak hybridization signal to the Towne DNA fragment is due to the existence of only 151 nucleotides of sequence identity with Towne DNA. The shared 104 bp sequence identity in Example 1 is responsible for a weak hybridization signal to XbaI "T" sized fragments from both Towne and Toledo DNAs seen in the XbaI digests (lanes 9 and 10). The XbaI digest of the clinical isolates (lanes 12 through 16) also reveals hybridization to multiple high molecular weight bands. Analysis of these and other clinical isolate genomes with other probes in the region has revealed that the shared sequences may be in inverted orientation in some isolates relative to the orientation in the Toledo strain.

FIG. 6 is a schematic illustration of the relative positions of novel sequences identified in Toledo genomic DNA, Towne genomic DNA in a comparison with AD169 strain genomic DNA. The dashed lines delimit the region of the genome where homologous and divergent sequences are found. The top line illustrates a Toledo DNA restriction map showing BamHI (indicated by "B") and XbaI (indicated by "X") restriction enzyme sites extending between the homology breakpoints identified by inverted triangles at nucleotides 175068 and 188843 (numbered with reference to the AD169 DNA sequence—EMBL accession number X17403). Subclones 4, 1300, C23K and 65 of the Toledo DNA sequence are shown in boxes above the map. An inverted region of homology with respect to Towne is shown by the inverted triangles between nucleotides 178221 and 175082. Unique sequences are shown by a thin line, and inverted repeat sequences denoted by thick lines, b'a'c'. The end of the c' repeats is shown with an arrow at nucleotide 191412. The middle line illustrates a Towne DNA restriction map showing BamHI (B) and XbaI (X) restriction enzyme sites as described above for Toledo and showing XbaI clones E, T, and Q in boxes below. Shaded area refers to homologous regions shared with Toledo DNA but inverted in orientation. Nucleotide numbers shown are with reference to the AD169 DNA sequence. Undetermined extent of b' repeat sequences in the Towne strain is shown by thin lines at AD169 strain nucleotide reference 180034. The bottom line illustrates the AD169 genome displayed in the prototype orientation. Unique sequences are displayed by a thin line, and inverted repeats of the long ($U_L$) and short ($U_S$) components are denoted by boxes, ab-b'a', and a'c'-ca. The a sequence, is a terminal direct repeat with an inverted copy (a'), at the junction of the long and short components. The length of the AD169 DNA sequence is indicated as 229354 nucleotides and the map position of the internal repeats are shown with the nucleotide reference numbers and arrows.

EXAMPLE 4

Open Reading Frame Analysis of the Novel Toledo and Towne DNA Sequences

The novel Toledo and Towne sequences encoded potential open reading frames (ORFs). Using an arbitrarily chosen parameter of 10 kiloDaltons as the minimum calculated protein molecular weight, a total of 36 ORFs were identified in the novel Toledo sequence and a total of 4 ORFs were identified in-the novel Towne sequence. The putative amino acid sequences of these ORFs are set forth in the sequence listing (SEQ ID NOS:2, 3, 4, 5, 7, 8, 9, 10, 11, 12, 13, 14, 15, 16, 17, 18, 19, 20, 21, 22, 23, 24, 25, 26, and 27). FIG. 5 shows the schematic presentation of these ORFs in the novel Toledo and Towne DNA sequences, together with previously reported AD169 ORFs of the corresponding region. Names were assigned for these ORFs starting from UL133 as the first ORF at the left side of the UL in Toledo sequence. The first ORF in the novel Towne sequence was assigned as UL147, which was determined to be present in the novel Toledo sequence disclosed here. UL130 and UL132 in AD169 were determined to be present in the novel Toledo sequence. Additionally, UL153 and UL154 exhibited regions of homology to IRL14 and IRL12, respectively. All ORFs were searched for homologous sequence in the non-redundant databases of NCBI using the BLASTP program. Among all ORFs searched, only UL132 identified a homologue in the database, which was HCMV mtrIII (GenBank Accession No. X75606), exhibiting 76% identity at the amino acid level. The solid circle identified the ORFs that contained the potential N-linked glycosylation site sequence, N-X(-P)-S/T. These potential glycoproteins may be biologically significant as antigenic or immunogenic molecules.

The present investigation is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed is:

1. A recombinant human cytomegalovirus comprising a human cytomegalovirus viral genome that encodes an infectious human cytomegalovirus, and further comprising a polynucleotide selected from the group consisting of,
   a. the polynucleotide of SEQ ID NO: 6; or
   b. at least one open reading frame of the polynucleotide of SEQ ID NO: 6.

2. The recombinant human cytomegalovirus of claim 1, wherein said human cytomegalovirus viral genome is not a complete Toledo strain cytomegalovirus genome.

3. The recombinant human cytomegalovirus of claim 1, wherein said human cytomegalovirus viral genome is derived from a Towne strain cytomegalovirus.

4. The recombinant human cytomegalovirus of claim 1, wherein said human cytomegalovirus viral genome is derived from a Towne-125 strain cytomegalovirus.

5. The recombinant human cytomegalovirus of claim 1, wherein said human cytomegalovirus viral genome is derived from a AD169 strain cytomegalovirus.

6. The recombinant human cytomegalovirus of claim 1, wherein said human cytomegalovirus viral genome is derived from a Towne strain cytomegalovirus and a Toledo strain cytomegalovirus genome.

7. An immunogenic composition comprising the recombinant human cytomegalovirus of claim 1 in admixture with a pharmaceutically acceptable carrier.

8. The recombinant human cytomegalovirus of claim. 1, wherein said human cytomegalovirus viral genome is derived from a Towne strain cytomegalovirus and wherein the recombinant human cytomegalovirus further comprises the polynucleotide of SEQ ID NO: 6.

9. An immunogenic composition comprising the recombinant human cytomegalovirus of claim 8 in admixture with a pharmaceutically acceptable carrier.

10. A method of inducing an immune response in a human comprising administering to a patient the immunogenic composition of claim 7 in an amount sufficient to stimulate an immune response in said human.

11. A method of inducing an immune response in a human comprising administering to a patient the immunogenic composition of claim 9 in an amount sufficient to stimulate an immune response in said human.

* * * * *

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
      (A) LENGTH: 4711 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Human CMV
      (B) STRAIN: Towne (ix) FEATURE:
      (A) NAME/KEY: CDS
      (B) LOCATION: complement (845..1321)
      (D) OTHER INFORMATION: /product= "UL147"

(ix) FEATURE:
      (A) NAME/KEY: CDS
      (B) LOCATION: complement (1368..1721)
      (D) OTHER INFORMATION: /product= "UL152"

(ix) FEATURE:
      (A) NAME/KEY: CDS
      (B) LOCATION: complement (2504..3337)
      (D) OTHER INFORMATION: /product= "UL153"

(ix) FEATURE:
      (A) NAME/KEY: CDS
      (B) LOCATION: complement (3515..4711)
      (D) OTHER INFORMATION: /product= "UL154"

(xi) SEQUENCE DESCRIPTION: SEQ ID NO: 1:

```
ATCGGGCGCC AGAGCTAGAT CAGGCGTATC AAATTCCACT GCCAGGCGAC CTGATTCTAA      60

CGGTTCCACG ATCCGGGAGA GCGTTTCTAG ATATAGAGCA AAGCGTACCA CGTCTACCT     120

CGGTGTAAAA AACTGTTGTG GGCGTTCACC GTCGTTGACC ACGTAAGCCA CGTAGAGGC     180

AACATTTTCC ACCACGGGTT CTAGCTGCAG GCGGCACGTA AAGCTTAGAA ACGACGGCT     240

TACGGTTTGG TTCCCGTGAA GCTGAAGCGT CACTTCCTTG CCGGGGCTCA CCGTGCTGT     300

ACGCCGCACC GAGTCGGTCA TCTGCTCCAG ATCGGTAGAC CAGAAGGGCG TGCAATGCA     360

ACTGTCCCAG TCGCGACACG CAGCCCAGCC TAGCTCGGTG AAGGGTCGAC GCACACCCG     420

AAAAGTGTGC TTGAAGACCA GGGGGTCGCC TCGGTAGCTC AGTAGCCGAA CATGCACAT     480

GTCGCGGCTA CGTTGACAGA CGGCCCGTAG ACAGGCAGGA CAAGCGTGAA CAGCAAGCG     540

AACATGCTGC GGGTTAGAAA ATGCGGCGTG CCGGCCACCG CCCGACTCAT AAACGCTAC     600

AGCATGACGT CTCAGATCAC ACAAGTGACG AGGAGCGTAC CGCAAATCAC TAGGGAAAA     660

GCCAGCAGAG CCCGATAGTC TTGCTCTTCG CGAACGATCT CGTCCGGTTC CTCGCAGTC     720

TCGTGGTCCA CAGAAGATGA GGAGCAGGAT TCTTCGTTAA TTTCTGCCAG GATACTAGT     780

CTGTACCACA CCAGAGCGCT CAGCGTGCCC AGGGCTACCG CACGGTAAAA TAGGGACAT     840

ATCACCAGCG CAATCTGAAG TGGTGGTAGT TCAGTTTCTT GGCGTATTTC CAGAGAAAG     900

CTTTGTAGGC CGTAGGGACT GGCCAGGCAC CGAACTCAAT ATTGGTAGAC ACTACGTCG     960
```

```
AAATGCGTTG TTCCTCGTCT AAGATTAACC GAAAAAATAG CCGGTTGATG TGACGACG      1020

CGGCTTGCGC GTTAGGATTG AGACACTTGG TGCCCTTGTC CTTTAAAATA GCCAGCAC      1080

CCTGACGATT GCAGCTTTCG CTCGCCGCGA TTGGCTTAAG CAATTCAGTT CCGATTGG      1140

GAGTATTCAA CAGAATTTGG TTGTTACAAC GACAGCGTTT GTCGTAATCT TCCAATTC      1200

AAAGATGGAC GGCTAGGGGA CATACGACAA ATAACATGTA TGCAGTCAAT TGCATATA      1260

GTACCGATAA AATGTTAGTG TGCGGATTCA GAATCGGATG ATGCAACCGT CTTAGCAT      1320

TATCGAAAAA GTATACATAT TACCGATTCA TTATAATTAG GGAATTATTT CCAACGCG      1380

CGTTTGTTAG TGACAGCGTT TTCTTCTACA TGCGGTCCAT TACTATCCTT TACTTTTA      1440

AATACTCTGT GCCATGAGTT GTCTTTTTTA CCATCCAGCC ATTTGGACAA ATGATGAT      1500

GGAGCTAAAC ATACAGGTTT ACCTCGAGGA GGCAATAGAT AATGTTGAGG TTTGTCAC      1560

TCAGGAGGAT TGGGAGGGTC ACGACCAACC CAAAATAAGC CACCTATAGG ATGATGTA      1620

GCTTTGTGGG TACACGGACA ACGCAATTCT CTACTGTGAA CCCCATGGTA ATACATAA      1680

GCCATCAAAA GACTAATCAG CGAACCAAAA ATTAATCGCA TTCTAATTTT ATTAACTA      1740

TCACTATCAG TAATTCGTAA TATCCGGTAT TCCCGGAAAA TCACTCAAAA CTGCGTCC      1800

GACACATCAA TTCCCGATAA GTACCCCCCT TTGAAATCGG ATCCCCCCAC ATACCAAT      1860

ATCACACAAC ACACAGGTTT AAAAATCGAT CACACGTCAA TTAGGTTTCA AAATCGAT      1920

TGTTTATTAT CAGGAATCTA GACTAATTCT ACAATGACAG CTCTGAATTT CTCTCTCG      1980

TTTCTTGTCA GGTTCTCATC ATCAATCTTC ACTTCCACCC ATCGAGGAGT CATCGTCG      2040

CCAAAACCCT TTGGGGTCGC TGGTTGGAAA AGTCTCTGAC ACGATCCAGG CACCCCGT      2100

CCAGTCCGAC TGATCTAGCT TACGGAGCAT CTCAACAGGC ATGAGCTGCA GGGCCACG      2160

TGTCACGGCA GGGATTATTA CTACCGTTCA GGTAAACTGT ATCTCCCTGA GTTACCGT      2220

TGGGTCTTTC TACATGTTGA CTTTGCGTAA AAAATCGCCG GTAAAATGTT TTTTCTTG      2280

CATGTAAAAG TACCGGAACT AAAATGCTAG TTAGAATGGT TGCAGTTGCT ATTAGCGC      2340

CTAGTAACAG TAGTTTAGTG TTACATTGTA TACCCATGTT TTTAATAACT ATGAATAT      2400

TGCTTCACAC CATAAGTGCT TAACCCACAA AAACCACACG GAGACATTAT TGGCTAAA      2460

TAAAAACAAA AGTTTATTGA TGTGCATGTT AGGTTTTAGT CTAAAATTCA TCTGGGTC      2520

ATTTGGGAAG TTTTGTATAA CGCGGTCTTC TGGGGACGCG ACGGCTACCC ATGTATAA      2580

CTATAAGTGC CACAGATACC ACTATACCCG CCCATACAGC ATGAATTCCC AGGGGAAT      2640

TAGTGTTTTT TACAGTTTTT ATTACATTGT CCCACGTTCT GCTATTATGC TGGTCTGA      2700

CCTCTTTTGT TTTACATTTA TCAGGTATAG GAGACGATGT TGCAGTTCCT GATAACAC      2760

TTAAATAGTA GTTTTCCTTT TTACCGTCAC TGTAACGTTG CAAAACGTAT TTTCCAGC      2820

GTTCGGTAGT TACGTTGTAT ATAGTGAGAG AGGTCTTATT GCAGTCTAAA CACATGCC      2880

TCAGTGGGA AGTTGAATAA TAATGTCCAA TGCTGCACAG TTGGTGTGCG CGAGGTCC       2940

ATTTTATCCA TTCTATATCG TGCCATACAT CCGTTCTACT GCAGTTTTTC AAAGTGAC      3000

ATCCACCGAC ATATCCTGTT ACATTAATTA CTTCGTAATT TAAATTAGAG TGTTTATA      3060

CGGTGTACAA ACTGCCATTG CAAGTTATGT TGCTGGTATT CAACCAGGGA GTAGTACT      3120

GAATGGTAGA AAACGTTAAT GTTGGCGTAG CGCTTGACGA TGATTTTGAA AGCGTTGA      3180

TGGTTGCTGA TGCGACTGAA GAAGCGGTAG AGGGTTTGTG CGTGGTTCCA TTTGCGAT      3240

CTGAAGTGCT GTTAGCATCG GTGACAGAGT TAGAAGAATT TGTGATAGTG GAGGCGGT      3300
```

-continued

```
AGGTAAAGGC AATTGCACGG ACAGGAGCAC GTGTCATTGC AACCTTCAGA TATCGTAA       3360

ATCAGTAACG TCCACTTAAC CGTAAATCTC CAGTCCATAA CGTTATTAAA TTTCGGTT       3420

CGGGCATTGA TGTTTCTTCG GACGTTGTTG ATCTTTCTTG CCCGTTTATT TTCTGATA       3480

GTCTCATAAG ACATTTATCC GGAAACGTTG CTTAGTCCTC GTGCTCAGGA TTGTATCG       3540

CTATGAATTC TGATTCACTT ATATCGTCAC TTAATGGATG ATATTTTTA  TTTAGAGC       3600

GTCGGACGAA AAATAGGAGA ATGCAGGCTA CACAAATTAA TGCTAACGTC CACGTAGT       3660

GTCTGCCGTG TGATGTGTTA GAATGATTGT TATAGCGGTA TAAATGATCT ATAGATGA       3720

TGGCTGTATT GTCTTCATAA TTGGTCGGTT TATGAGAAGT GTCCCATTCG TGCTTTGG       3780

CTTCACATAC CCAGGGATTC ACGTGTGTCC CGTTTGTGTT GTTTCTAGGA TGTATTTG       3840

GATTAAAGTT TTGATTTTGT TCGGAGGGAT GCCCAGTTTT ATAACATCGA AAGCTATA       3900

TACCAGAATG AGTAAAATTA AGACCGTACA GAGATAAAGA TAAATTACGA TCGCATGT       3960

AACATAAATC ATAGTGATGT TTTAGATAAT TTGTGTGCCA CTCACATAGT ATACGCGA       4020

GGAGGATTTT CAATGAATGG TTATGATATT TTCCATTTCT TATGTTGGGA TGGGTGTA       4080

TTCCGTGTGT GGATATATTA AAATGTCTAA GCCAGGCTGT TTTGTAGCAC GATGTGAT       4140

TTAGGTTGTG TGTTATAGTA ATATTGTCTC CTTGTGCCGC CTCCAATAAT GTTTCAGA       4200

CTTTTGATAT CGTATTATTT GTACTGTTAG GCGATGAGCA AGTTGGAAGC GGTGTAGT       4260

CGTTTTCATT TGCATTTATC ATAGTAGTAG TGTTGGTTGA TAATGATATA GTTTGCAA       4320

TCACAGTACT ATCGGTTACA TGCTGTGTCG ATGAATTCGT GTCGCCGTTT GGTGAAGT       4380

TTATTACAGT TACGTTAGTT GTAGATGTTT GGGTAGATAT GGTGGAAATA GTTGAGGT       4440

CGTCTGTGCC TTTTACAGAG CTTGCAGTGA ATCCTGTGGA TGTGTTGACG TTGCCATT       4500

AGGATGTGAA CATAGTGGTA GACATTTCGG TGGTTTGTAA CGTAGATGTC AGTTGTGT       4560

TAGATATTAA GCTTGTGGGT GTAATCGACG TGGAAGTATT GGCGATAGTG GTGTTGTT       4620

ACTTGCTTTT CTGCAGAATC CAAAAAATAA TAAACATGCA TATTATTTGC GTATATGA       4680

ACTTGTTCCA CCGTCGATGT TGTGTGCGCA T                                    4711
```

(2) INFORMATION FOR SEQ ID NO: 2:

(i) SEQUENCE CHARACTERISTICS:
        (A) LENGTH: 159 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Met Leu Arg Arg Leu His His Pro Ile Leu Asn Pro His Thr Asn
 1               5                  10                  15

Ile Leu Ser Val Arg Tyr Met Gln Leu Thr Ala Tyr Met Leu Phe Val
                20                  25                  30

Val Cys Pro Leu Ala Val His Leu Leu Glu Leu Glu Asp Tyr Asp Lys
            35                  40                  45

Arg Cys Arg Cys Asn Asn Gln Ile Leu Leu Asn Thr Leu Pro Ile Gly
        50                  55                  60

Thr Glu Leu Leu Lys Pro Ile Ala Ala Ser Glu Ser Cys Asn Arg Gln
65                  70                  75                  80

Glu Val Leu Ala Ile Leu Lys Asp Lys Gly Thr Lys Cys Leu Asn Pro
                85                  90                  95

Asn Ala Gln Ala Val Arg Arg His Ile Asn Arg Leu Phe Phe Arg Leu
```

-continued

```
                    100                 105                 110
Ile Leu Asp Glu Glu Gln Arg Ile Tyr Asp Val Val Ser Thr Asn Ile
            115                 120                 125

Glu Phe Gly Ala Trp Pro Val Pro Thr Ala Tyr Lys Ala Phe Leu Trp
        130                 135                 140

Lys Tyr Ala Lys Lys Leu Asn Tyr His His Phe Arg Leu Arg Trp
145                 150                 155
```

(2) INFORMATION FOR SEQ ID NO: 3:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO: 3:

```
Met Arg Leu Ile Phe Gly Ser Leu Ile Ser Leu Leu Met Ala Phe Met
1               5                   10                  15

Tyr Tyr His Gly Val His Ser Arg Glu Leu Arg Cys Pro Cys Thr His
            20                  25                  30

Lys Ala Leu His His Pro Ile Gly Gly Leu Phe Trp Val Gly Arg Asp
        35                  40                  45

Pro Pro Asn Pro Pro Glu Cys Asp Lys Pro Gln His Tyr Leu Leu Pro
    50                  55                  60

Pro Arg Gly Lys Pro Val Cys Leu Ala Pro Asp His His Leu Ser Lys
65                  70                  75                  80

Trp Leu Asp Gly Lys Lys Asp Asn Ser Trp His Arg Val Leu Val Lys
                85                  90                  95

Val Lys Asp Ser Asn Gly Pro His Val Glu Glu Asn Ala Val Thr Asn
            100                 105                 110

Lys Arg Pro Arg Trp Lys
        115
```

(2) INFORMATION FOR SEQ ID NO: 4:

(i) SEQUENCE CHARACTERISTICS:
        (A) LENGTH: 278 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Thr Arg Ala Pro Val Arg Ala Ile Ala Phe Thr Ser Thr Ala Ser
1               5                   10                  15

Thr Ile Thr Asn Ser Ser Asn Ser Val Thr Asp Ala Asn Ser Thr Ser
            20                  25                  30

Ala Ile Ala Asn Gly Thr Thr His Lys Pro Ser Thr Ala Ser Ser Val
        35                  40                  45

Ala Ser Ala Thr Thr Ser Thr Leu Ser Lys Ser Ser Ser Ser Ala Thr
    50                  55                  60

Pro Thr Leu Thr Phe Ser Thr Ile His Ser Thr Thr Pro Trp Leu Asn
65                  70                  75                  80

Thr Ser Asn Ile Thr Cys Asn Gly Ser Leu Tyr Thr Val Tyr Lys His
                85                  90                  95

Ser Asn Leu Asn Tyr Glu Val Ile Asn Val Thr Gly Tyr Val Gly Gly
            100                 105                 110
```

```
Tyr Val Thr Leu Lys Asn Cys Ser Arg Thr Asp Val Trp His Asp Ile
            115                 120                 125

Glu Trp Ile Lys Tyr Gly Pro Arg Ala His Gln Leu Cys Ser Ile Gly
    130                 135                 140

His Tyr Tyr Ser Thr Ser Pro Leu Asn Gly Met Cys Leu Asp Cys Asn
145                 150                 155                 160

Lys Thr Ser Leu Thr Ile Tyr Asn Val Thr Thr Glu His Ala Gly Lys
                165                 170                 175

Tyr Val Leu Gln Arg Tyr Ser Asp Gly Lys Lys Glu Asn Tyr Tyr Leu
            180                 185                 190

Thr Val Leu Ser Gly Thr Ala Thr Ser Ser Pro Ile Pro Asp Lys Cys
            195                 200                 205

Lys Thr Lys Glu Glu Ser Asp Gln His Asn Ser Arg Thr Trp Asp Asn
    210                 215                 220

Val Ile Lys Thr Val Lys Asn Thr Asn Ile Pro Leu Gly Ile His Ala
225                 230                 235                 240

Val Trp Ala Gly Ile Val Ser Val Ala Leu Ile Ala Leu Tyr Met
                245                 250                 255

Gly Ser Arg Arg Val Pro Arg Arg Pro Arg Tyr Thr Lys Leu Pro Lys
            260                 265                 270

Tyr Asp Pro Asp Glu Phe
            275

(2) INFORMATION FOR SEQ ID NO: 5:

(i) SEQUENCE CHARACTERISTICS:
        (A) LENGTH: 399 amino acids
        (B) TYPE: amino acid
        (D) TOPOLOGY: linear (ii) MOLECULE TYPE: protein (xi) SEQUENCE DESCRIPTION: SEQ ID NO: 5:

Met Arg Thr Gln His Arg Arg Trp Asn Lys Ser Ser Tyr Thr Gln Ile
1               5                   10                  15

Ile Cys Met Phe Ile Ile Phe Trp Ile Leu Gln Lys Ser Lys Cys Asn
                20                  25                  30

Asn Thr Thr Ile Ala Asn Thr Ser Thr Ser Ile Thr Pro Thr Ser Leu
            35                  40                  45

Ile Ser Thr Thr Gln Leu Thr Ser Thr Leu Gln Thr Thr Glu Met Ser
        50                  55                  60

Thr Thr Met Phe Thr Ser Ser Asn Gly Asn Val Asn Thr Ser Thr Gly
65                  70                  75                  80

Phe Thr Ala Ser Ser Val Lys Gly Thr Asp Val Thr Ser Thr Ile Ser
                85                  90                  95

Thr Ile Ser Thr Gln Thr Ser Thr Thr Asn Val Thr Val Ile Thr Thr
                100                 105                 110

Ser Pro Asn Gly Asp Thr Asn Ser Ser Thr Gln His Val Thr Asp Ser
            115                 120                 125

Thr Val Thr Leu Gln Thr Ile Ser Leu Ser Thr Asn Thr Thr Thr Met
        130                 135                 140

Ile Asn Ala Asn Glu Asn Val Thr Thr Pro Leu Pro Thr Cys Ser Ser
145                 150                 155                 160

Pro Asn Ser Thr Asn Asn Thr Ile Ser Lys Glu Ser Glu Thr Leu Leu
                165                 170                 175
```

-continued

```
Glu Ala Ala Gln Gly Asp Asn Ile Thr Ile Thr His Asn Leu Thr Ile
            180                 185                 190

Thr Ser Cys Tyr Lys Thr Ala Trp Leu Arg His Phe Asn Ile Ser Thr
        195                 200                 205

His Gly Lys Tyr Thr His Pro Asn Ile Arg Asn Gly Lys Tyr His Asn
    210                 215                 220

His Ser Leu Lys Ile Leu His Ser Arg Ile Leu Cys Glu Trp His Thr
225                 230                 235                 240

Asn Tyr Leu Lys His His Tyr Asp Leu Cys Phe Thr Cys Asp Arg Asn
                245                 250                 255

Leu Ser Leu Ser Leu Tyr Gly Leu Asn Phe Thr His Ser Gly Lys Tyr
            260                 265                 270

Ser Phe Arg Cys Tyr Lys Thr Gly His Pro Ser Glu Gln Asn Gln Asn
        275                 280                 285

Phe Asn Leu Gln Ile His Pro Arg Asn Asn Thr Asn Gly Thr His Val
    290                 295                 300

Asn Pro Trp Val Cys Glu Glu Pro Lys His Glu Trp Asp Thr Ser His
305                 310                 315                 320

Lys Pro Thr Asn Tyr Glu Asp Asn Thr Ala Thr Ser Ser Ile Asp His
                325                 330                 335

Leu Tyr Arg Tyr Asn Asn His Ser Asn Thr Ser His Gly Arg Arg Thr
            340                 345                 350

Thr Trp Thr Leu Ala Leu Ile Cys Val Ala Cys Ile Leu Leu Phe Phe
        355                 360                 365

Val Arg Arg Ala Leu Asn Lys Lys Tyr His Pro Leu Ser Asp Asp Ile
    370                 375                 380

Ser Glu Ser Glu Phe Ile Val Arg Tyr Asn Pro Glu His Glu Asp
385                 390                 395

(2) INFORMATION FOR SEQ ID NO: 6:

(i) SEQUENCE CHARACTERISTICS:
        (A) LENGTH: 18318 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Human CMV
        (B) STRAIN: Toledo (ix) FEATURE:
        (A) NAME/KEY: CDS
        (B) LOCATION: 511..1281
        (D) OTHER INFORMATION: /product = "UL133"

(ix) FEATURE:
        (A) NAME/KEY: CDS
        (B) LOCATION: 1401..2384
        (D) OTHER INFORMATION: /product = "UL135"

(ix) FEATURE:
        (A) NAME/KEY: CDS
        (B) LOCATION: 2478..3197
        (D) OTHER INFORMATION: /product = "UL136"

(ix) FEATURE:
        (A) NAME/KEY: CDS
        (B) LOCATION: 3283..3789
```

-continued

```
        (D) OTHER INFORMATION: /product = "UL138"

(ix) FEATURE:
        (A) NAME/KEY: CDS
        (B) LOCATION: 4355..4759
        (D) OTHER INFORMATION: /product = "UL139"

(ix) FEATURE:
        (A) NAME/KEY: CDS
        (B) LOCATION: 4944..5285
        (D) OTHER INFORMATION: /product = "UL140"

(ix) FEATURE:
        (A) NAME/KEY: CDS
        (B) LOCATION: 5558..6832
        (D) OTHER INFORMATION: /product = "UL141"

(ix) FEATURE:
        (A) NAME/KEY: CDS
        (B) LOCATION: 6908..7825
        (D) OTHER INFORMATION: /product = "UL142"

(ix) FEATURE:
        (A) NAME/KEY: CDS
        (B) LOCATION: 7813..8088
        (D) OTHER INFORMATION: /product = "UL143"

(ix) FEATURE:
        (A) NAME/KEY: CDS
        (B) LOCATION: 8468..8995
        (D) OTHER INFORMATION: /product = "UL144"

(ix) FEATURE:
        (A) NAME/KEY: CDS
        (B) LOCATION: 9327..9626
        (D) OTHER INFORMATION: /product = "UL145"

(ix) FEATURE:
        (A) NAME/KEY: CDS
        (B) LOCATION: 9910..10260
        (D) OTHER INFORMATION: /product = "UL146"

(ix) FEATURE:
        (A) NAME/KEY: CDS
        (B) LOCATION: 10328..10804
        (D) OTHER INFORMATION: /product = "UL147"

(ix) FEATURE:
        (A) NAME/KEY: CDS
        (B) LOCATION: 11106..12053
        (D) OTHER INFORMATION: /product = "UL148"

(ix) FEATURE:
        (A) NAME/KEY: CDS
        (B) LOCATION: 12133..12942
        (D) OTHER INFORMATION: /product = "UL132"

(ix) FEATURE:
        (A) NAME/KEY: CDS
        (B) LOCATION: 13569..14210
        (D) OTHER INFORMATION: /product = "UL130"

(ix) FEATURE:
        (A) NAME/KEY: CDS
        (B) LOCATION: 16216..16581
        (D) OTHER INFORMATION: /product = "UL149"

(ix) FEATURE:
        (A) NAME/KEY: CDS
        (B) LOCATION: 1004..1528
        (D) OTHER INFORMATION: /product = "UL134"

(ix) FEATURE:
        (A) NAME/KEY: CDS
        (B) LOCATION: 3063..3350
        (D) OTHER INFORMATION: /product = "UL137"

(ix) FEATURE:
        (A) NAME/KEY: CDS
```

```
        (B) LOCATION: 16337..18262
        (D) OTHER INFORMATION: /product = "UL150"

(ix) FEATURE:
        (A) NAME/KEY: CDS
        (B) LOCATION: 17752..18759
        (D) OTHER INFORMATION: /product = "UL151"

(xi) SEQUENCE DESCRIPTION: SEQ ID NO: 6:
```

| | | | | | |
|---|---|---|---|---|---|
| CGCTGTAGGG | ATAAATAGTG | CGATGGCGTT | TGTGGGAGAA | CGCAGTAGCG | ATGGGTTGCG | 60 |
| ACGTGCACGA | TCCTTCGTGG | CAATGCCAAT | GGGGCGTTCC | CACGATTATC | GTGGCCTGG | 120 |
| TAACATGCGC | GGCTTTAGGA | ATTTGGTGTT | TGCGGGATC | GTCGGCGGAT | GTCTCTTCG | 180 |
| GACCCGGCAT | CGCAGCCGTA | GTCGGCTGTT | CTGTTTTCAT | GATTTTCCTC | TGCGCGTAT | 240 |
| TCATCCGTTA | CCGGGAATTC | TTCAAAGACT | CCGTAATCGA | CCTCCTTACC | TGCCGATGG | 300 |
| TTCGCTACTG | CAGCTGCAGC | TGTAAGTGCA | GCTGCAAATG | CATCTCGGGC | CCCTGTAGC | 360 |
| GCTGCTGTTC | AGCGTGTTAC | AAGGAGACGA | TGATTTACGA | CATGGTCCAA | TACGGTCAT | 420 |
| GACGGCGTCC | CGGACACGGC | GACGATCCCG | ACAGGGTGAT | CTGCGAGATA | GTCGAGAGT | 480 |
| CCCCGGTTTC | GGCGCCGACG | GTGTCCGTCC | CCCCGCCGTC | GGAGGAGTCC | CACCAGCCC | 540 |
| TCATCCCACC | GCAGCCGCCA | GCACCGACAT | CGGAACCCAA | ACCGAAGAAA | GGTAGGGCG | 600 |
| AAGATAAACC | GAAGGGTAGA | CCGAAAGACA | AACCTCCGTG | CGAACCGACG | GTGAGTTCA | 660 |
| AACCACCGTC | GCAGCCGACG | GCAATGCCCG | GCGGTCCGCC | CGACGCGCCT | CCCCCCGCC | 720 |
| TGCCGCAGAT | GCCACCCGGC | GTGGCCGAGG | CGGTACAAGC | TGCCGTGCAG | GCGGCCGTG | 780 |
| CCGCGGCTCT | ACAACAACAG | CAGCAGCATC | AGACCGGAAC | GTAACCCGCC | CCCGGTGCG | 840 |
| TAAGGAATTT | TCCGACTTGG | CGCACATCTC | CTTCCTCAAT | GTTTGGACAA | TAAACACAT | 900 |
| CCTTGCCAAA | AAATGACGTT | TCCAGAAATC | CAAGGCATAA | ATGTCCGTAC | ACCGGCCCT | 960 |
| CCCAACACGG | AGTTTGAGAT | TCCAAGCAGG | AGAGAAGATC | ATGGTGTGGA | TATGGCTC | 1020 |
| CATCGGGCTC | CTCGGCGGTA | CCGGACTGGC | TTCCCTGGTC | CTGGCCATTT | CCTTATTT | 1080 |
| CCAGCGCCGA | GGCCGCAAGC | GATCCGACGA | GACTTCGTCG | CGAGGCCGGC | TCCCGGGT | 1140 |
| TGCTTCTGAT | AAGCGTGGTG | CCTGCGCGTG | CTGCTATCGA | AATCCGAAAG | AAGACGTC | 1200 |
| CGAGCCGCTG | GATCTGGAAC | TGGGGCTCAT | GCGGGTGGAC | ACCCACCCGC | CGACGCCG | 1260 |
| GGTGCCGCGG | TGTACGTCGC | TCTACATAGG | AGAGGATGGT | CTGCCGATAG | ATAAACCC | 1320 |
| GTTTCCTCCG | GCGCGGTTCG | AGATCCCCGA | CGTATCCACG | CCGGGAACGC | CGACCAGC | 1380 |
| CGGCCGATCT | CCGTCGCATT | GCTCCTCGTC | GAGCTCTTTG | TCGTCCTCGA | CCAGCGTC | 1440 |
| CACGGTGCTG | TATCAGCCGC | CGCCATCCTG | GAAGCCACCT | CCGCCGCCCG | GGCGCAAG | 1500 |
| GCGGCCGCCT | ACGCCGCCGG | TCCGGGCCCC | CACCACGCGG | CTGTCGTCGC | ACAGACCC | 1560 |
| GACGCCGATA | CCCGCGCCGC | GTAAGAACCT | GAGCACGCCG | CCCACCAAGA | AAACGCCG | 1620 |
| GCCCACGAAA | CCCAAGCCGG | TCGGCTGGAC | ACCGCCGGTG | ACACCCAGGC | CCTTCCCG | 1680 |
| AACGCCGACG | CCACAAAAGC | CGCCGCGGAA | TCCGAGACTA | CCGCGCACCG | TCGGTCTG | 1740 |
| GAATCTCTCG | AAGGTGGGAC | TCTCGTGTCC | CTGTCCCCGA | CCCCGCACGC | CGACGGAG | 1800 |
| GACCACGCTG | CCTATCGTGT | CGGTTTCCGA | GCTAGCCCCG | CCTCCTCGAT | GGTCGGAC | 1860 |
| CGAGGAACTC | TTGGAACAGG | CGGTGCAGAG | CGTCATGAAG | GACGCCGAGT | CGATGCAG | 1920 |
| GACCTGAGAC | CGAAAGAGCG | AGCGCGTCCG | TTGTACAGTT | GTATAGCAGC | ACACGCCT | 1980 |
| CCTCTTTTTC | ACCGCAGCTA | AGAGAGAGAA | AGAGAGTATG | TCAGTCAAGG | GCGTGGAG | 2040 |
| GCCAGAAATG | ACGTGGGACT | TGGACGTTAG | AAATAAATGG | CGGCGTCGAA | AGGCCCTG | 2100 |

```
TCGCATTCAC CGGTTCTGGG AATGTCGGCT ACGGGTGTGG TGGCTGAGTG ACGCCGGC      2160

AAGAGAAACC GACCCACCGC GTCCCCGACG CCGCCCGACT TGGATGACCG CGGTGTTT      2220

CGTTATCTGT GCCGTTTTGC TTACGCTTAT GATTATGGCC ATCGGCGCGC TCATCGCG      2280

CTTAAGATAT TACCACCAGG ACAGTTGGCG AGACATGCTC CACGATCTAT TTTGCGGC      2340

TCATTATCCC GAGAAGTGCC GTCGGCACCA CGAGCGGCAG AGAAGGAGAC GGCAAGCC      2400

GGATGTGCCC GACCCGGAAC TCGGCGACCC GGCCCGCCGG CCGTTGAACG GAGCTATG      2460

CTACGGCAGC GGCTGTCGCT TCGACACGGT GGAAATGGTG GACGAGACGA GACCCGCG      2520

GCCGGCGCTG TCATCGCCCG AAACCGGCGA CGATAGCAAC GACGACGCGG TTGCCGGC      2580

AGGTGCTGGC GGGGTAACAT CACCCGCGAC TCGTACGACG TCGCCGAACG CACTGCTG      2640

AGAATGGATG GATGCGGTGC ATGTGGCGGT CCAAGCCGCC GTTCAAGCGA CCGTGCAA      2700

AAGTGGCCCG CGGGAGAACG CCGTATCTCC CGCTACGTAA GAGGGTTGAG GGGGCCGT      2760

CCGCGCGAGT GCTGTACAAA AGAGAGAGAC TGGGACGTAG ATCCGGACAG AGGACGGT      2820

CCATGGACGA TCTGCCGCTG AATGTCGGGT TACCCATCAT CGGCGTGATG CTCGTGCT      2880

TCGTGGCCAT CCTCTGCTAT CTGGCTTACC ACTGGCACGA CACCTTCAAA CTGGTGCG      2940

TGTTTCTGAG CTACCGCTGG CTGATCCGCT GTTGCGAGCT GTACGGGGAG TACGAGCG      3000

GGTTCGCGGA CCTGTCGTCT CTGGGCCTCG GCGCCGTACG GCGGGAGTCG GACAGACG      3060

ACCGTTTCTC CGAACGGCCC GACGAGATCT TGGTCCGTTG GGAGGAAGTG TCTTCCCA      3120

GCAGCTACGC GTCGTCGCGG ATAACAGACC GCCGTGTGGG TTCATCGTCT TCGTCGTC      3180

TCCACGTCGC TAGCCAGAGA AACAGCGTGC CTCCGCCGGA CATGGCGGTG ACGGCGCC      3240

TGACCGACGT CGATCTGTTG AAACCCGTGA CGGGATCCGC GACGCAGTTC ACCACCGT      3300

CCATGGTACA TTATCATCAA GAGTACACGT GAATGAGAAA AGAAAAAAG AGGGGAGC      3360

ATCGCGATAA TGTCGCTTTG ACATTCTCTG CTCGATCTAC TCAGCGTCTG CACGAAAC      3420

CATCCGCACG GAGGCGAGCC CAAGCGTATC TGCAGCAAGC GGTTCTTTCC CTCGGTGA      3480

GTGGCAGCAT CGGTGGCGGG AGCTTGTTCG ACGATGGAC GGTGAGGAGT CCCTGGCG      3540

CAGGCGGCTC CCGGGTGTGG AGTTCAACGG GTGGTAATGG TGGCGGTGAT CGGTGTTA      3600

AAACGGTGGC CCTGGCAAAC ATATATCTAC TGTAAACCCT CTGCTCTGTT AATAAAAA      3660

ACACTTTTCA CATGAGTTCG TAATTTTATT GTGTAGTGGA AATTTTTACG TCATTGGG      3720

ACCCCAGAAT GAAAGAGTAT AATGTGCATA TCACCGGGGG TTCCCTGTCA GTACGAAT      3780

ACACAACGCG GGTTACATTA CGATAAACTT TCCGGTAAAA CGATGCCGAT ACAGCGTG      3840

TAACGCTGAT TGTTACGACA AACGAGTTGG TATATCCATT ATATAGTAAC GAACATGC      3900

TGGATATTAG TTTTATTTGC ACTCGCCGCA TCGGCGAGTG AAACCACTAC AGGTACCA      3960

TCTAATTCCA GTCAATCTAC TAGTGCTACC GCCAACACGA CCGTATCGAC ATGTATTA      4020

GCCTCTAACG GCAGTAGCTG GACAGTACCA CAGCTCGCGC TGCTTGCCGC TAGCGGCT      4080

ACATTATCTG GACTCCTTCT CTTATTTACC TGCTGCTTTT GCTGCTTTTG GCTAGTAC      4140

AAAATCTGCA GCTGCTGCGG CAACTCCTCC GAGTCAGAGA GCAAAACAAC CCACGCGT      4200

ACCAATGCCG CATTCACTTC TTCCGACGCA ACGTTACCCA TGGCACTAC AGGGTCGT      4260

ACTCCCCCAC AGGACGGCTC ATTTCCACCT CCGCCTCGGT GACGTAGGCT AAACCGAA      4320

CCACGTTGAA CCTAACGCGG TTTCGGAAGG CCTGAGACGT CACTTTCACA ATGACGTC      4380

TATACACGTT CATCATAAAA CACCGTAGAG GCTAAGGCTT CGGTAGGGAG AGACCTCA      4440
```

| | |
|---|---|
| TGTTCCTGAT GAGCACCCGT GCTCTCATCT CTTCAGACTT GTCATGACCC CCGCTCAG | 4500 |
| TAACGCGACT ACCACCGTGC ACCCGCACGA CGCAAAAAAC GGCAGCGGCG GTAGTGCC | 4560 |
| GCCGACCCTC GTCGTTTTCG GCTTTATCGT TACGCTACTT TTCTTTCTCT TTATGCTC | 4620 |
| CTTTTGGAAC AACGACGTGT TCCGTAAGCT GCTCCGTGCG CTTGGATCCA GCGCTGTT | 4680 |
| GACCGCTTCG ACGCGTGGCA AGACGAGGTC ATCTACCGTC GTCCATCACG TCGTTCCC | 4740 |
| AGCGACGACG AGAGTCGTAC TAACAGCGTG TCATCGTACG TTCTTTTATC ACCCGCGT | 4800 |
| GATGGCGGTT TTGACAACCC GGCACTGACA GAGGCCGTCG ACAGCGTGGA CGACTGGG | 4860 |
| ACCACCTCGG TTTTCTACGC CACGTCCGAC GAAACGGCGG ACGCCGAGCG CCGAGACT | 4920 |
| CAGCAACTGC TCATCGAGCT TCCGCCGGAG CCGCTCCCGC CCGACGTGGT GGCGGCCA | 4980 |
| CAGAAAGCAG TGAAACGCGC TGTACAGAAC GCACTACGAC ACAGCCACGA CTCTTGGC | 5040 |
| CTTCATCAGA CCCTGTGACG CCAGATGAAC GTTCCTTCTT AAACATCCGA GGTAGCAA | 5100 |
| AGACAGGTCG CGTACCGCCG GCGACGCGAG AGTTCCTGCG CGGTGCTGGT CCACCACG | 5160 |
| GGCCGCGACG GCGACGGCGA GGGGGAGGCA GCAAAAAAGA CCTGCAAAAA AACCGGAC | 5220 |
| TCAGTTGCGG GCATCCCGGG CGAGAAGCTG CGTCGCACGG TGGTCACCAC CACGCCGG | 5280 |
| CGACGTTTGA GCGGCCGACA CACGGAGCAG GAGCAGGCGG GCATGCGTCT CTGTGAAA | 5340 |
| GGGAAGAAAA GAATCATCAT GTGCCGCCGG GAGTCGCTCC GAACTCTGCC GTGGCTGT | 5400 |
| TGGGTGCTGT TGAGCTGCCC GCGACTCCTC GAATATTCTT CCTCTTCGTT CCCCTTCG | 5460 |
| ACCGCTGACA TTGCCGAAAA GATGTGGGCC GAGAATTATG AGACCACGTC GCCGGCGC | 5520 |
| GTGTTGGTCG CCGAGGGAGA GCAAGTTACC ATCCCCTGCA CGGTCATGAC ACACTCCT | 5580 |
| CCCATGGTCT CCATTCGCGC ACGTTTCTGT CGTTCCCACG ACGGCAGCGA CGAGCTCA | 5640 |
| CTGGACGCCG TCAAAGGCCA TCGGCTGATG AACGGACTCC AGTACCGCCT GCCGTACG | 5700 |
| ACTTGGAATT TCTCGCAATT GCATCTCGGC CAAATATTCT CGCTTACTTT TAACGTAT | 5760 |
| ATGGACACAG CCGGCATGTA CGAATGCGTG CTACGCAACT ACAGCCACGG CCTCATCA | 5820 |
| CAACGCTTCG TAATTCTCAC GCAGCTGGAG ACGCTCAGCC GGCCCGACGA ACCTTGCT | 5880 |
| ACACCGGCGT TAGGTCGCTA CTCGCTGGGA GACCAGATCT GGTCGCCGAC GCCCTGGC | 5940 |
| CTACGGAATC ACGACTGCGG AACGTACCGC GGCTTTCAAC GCAACTACTT CTATATCG | 6000 |
| CGCGCCGACG CCGAGGATTG CTGGAAACCC GCATGTCCGG ACGAGGAACC CGACCGCT | 6060 |
| TGGACAGTGA TACAGCGTTA CCGGCTCCCC GGCGACTGCT ACCGTTCGCA GCCACACC | 6120 |
| CCGAAATTTT TACCGGTGAC GCCAGCACCG CCGGCCGACA TAGACACCGG GATGTCTC | 6180 |
| TGGGCCACTC GGGGAATCGC GGCGTTTTTG GGGTTTTGGA GTATTTTTAC CGTATGTT | 6240 |
| CTATGCTACC TGTGTTATCT GCAGTGTTGT GGACGCTGGT GTCCCACGCC GGGAAGGG | 6300 |
| CGACGAGGCG GTGAGGGCTA TCGACGCCTA CCGACTTACG ATAGTTACCC CGGTGTTA | 6360 |
| AAGATGAAGA GGTGAGAACA CGTATAAAAT AAAAAAATAA TATGTTAAAA AATGCAGT | 6420 |
| GTGAAGTGTG AATAGTGTGA TTAAAATATG CGGATTGAAT GGGTGTGGTG GTTATTCG | 6480 |
| TACTTTGTGT CATCCGTTGG GAGCGAACGG TCATTATCCT ATCGTTACCA CTTGGAAT | 6540 |
| AATTCATCTA CCAACGTGGT TTGCAACGGA ACATTTCCG TGTTTGTAAA CGGCACCC | 6600 |
| GGTGTGCGGT ATAACATTAC GGTAGGAATC AGTTCGTCTT TATTAATAGG ACACCTTA | 6660 |
| ATACAAGTAT TGGAATCATG GTTCACACCC TGGGTCCAAA ATAAAAGTTA CAACAAAC | 6720 |
| CCCCTAGGTG ACACTGAAAC GCTTTATAAT ATAGATAGCG AAAACATTCA TCGCGTAT | 6780 |
| CAATATTTTC ACACAAGATG GATAAAATCT CTGCAAGAGA ATCACACTTG CGACCTCA | 6840 |

-continued

```
AACAGTACAC CTACCTATAC ATATCAAGTA AACGTGAACA ACACGAATTA CCTAACAC      6900
ACATCCTCGG GATGGCAAGA CCGTCTAAAT TACACCGTCA TAAATAGTAC ACACTTTA      6960
CTCACAGAAT CGAACATAAC CAGCATTCAA AAATATCTCA ACACTACCTG CATAGAAA      7020
CTCCGTAACT ACACCTTGGA GTCCGTATAC ACCACAACTG TGCCTCAAAA CATAACAA      7080
TCTCAACACG CAACAACCAC TATGCACACA ATACCTCCAA ATACAATAAC AATTCAAA      7140
ACAACTCAAA GCCATACTGT ACAGACGCCG TCTTTTAACG ACACACATAA CGTGACGA      7200
CACACGTTAA ACATAAGCTA CGTTTTATCA CAAAAAACGA ATAACACAAC ATCACCGT      7260
ATATATGCCA TACCTATGGG CGCTACAGCC ACAATAGGCG CCGGTTTATA TATCGGGA      7320
CACTTTACGC CGGTTAAGTT CGTATACGAG GTATGGCGCG GTCAGTAAAG ACGATTCG      7380
TTCAACACAT ATACTCCCCA CGATCCTCGA ACACCTTACA GCATATGAGC AAAAAACA      7440
AAAGTATAGC CACAATCACA TTTGGGCGAA TAACATGCTG TCATCCACTA GCGTCTAT      7500
ATCTAATGTT TAACGGGAGC TGTACTGTCA CCGTTAAAAT ATCCATGGGA ATCAACGG      7560
CAACCAACGT CCATCAGCTT GTGATTGTGC TCCATCTGGG TAACCGCTGT CAGCCTTG      7620
GACAGGTGTA ATCACAGCTG TCACATAACT CACGAAGCCT CCAATCACAG CAGCACAC      7680
AGTCCTAACG CCATTGGCGT GTATAAAAGT TCGGAAAACT TGACGGTTGT ACGGCACG      7740
AAATCGATGT AGTGGTATGT TTTTCCAGCA GAGACCGTGT GCGGTCTCTT AGGTTCGC      7800
TACTGTGGCT GGAAACTGGT TACCTGTGAA GATGGCTAAC TATCCTGTTC TGTCCTGG      7860
AAACTTTTGG CGTCGTAGGT GGACTTTGCA GTATGCGGGT TAGTGAAGTT ATGTCATT      7920
TTTACGTTTA CGATCTCGTA TTACAAACCG CGGAGAGGAT GATACCGTTC GGCCCCAT      7980
GTTATTTTTA TTCTTCCGGT AGGAGGCATG AAGCCTCTGA TAATGCTCAT CTGCTTTG      8040
GTGATATTAT TGCAGCTTGG AGTGACTAAA GTGTGTCAGC ATAATGAAGT GCAACTGG      8100
AATGAGTGCT GCCCTCCGTG TGGTTCGGGA CAAAGAGTTA CTAAAGTATG CACGGATT      8160
ACCAGTGTAA CGTGTACCCC TTGCCCCAAC GGCACGTATG TATCGGGACT TTACAACT      8220
ACCGATTGCA CTCAATGTAA CGTCACTCAG GTCATGATTC GTAACTGCAC TTCCACCA      8280
AATACCGTAT GCGCACCTAA GAACCATACG TACTTTTCCA CTCCAGGCGT CCAACATC      8340
AAACAACGAC AGCAAAATCA TACCGCACAT ATAACCGTCA AACAAGGAAA AAGCGGTC      8400
CATACTCTAG CCTGGTTGTC TCTCTTTATC TTTCTTGTGG GTATCATACT TTTAATTC      8460
TATCTTATAG CCGCCTATCG GAGTGAGAGA TGCCAACAGT GTTGCTCAAT CGGCAAAA      8520
TTCTACCGCA CCCTGTAAGC TTCCTGTTGT TGTTTTTACA TCACGGTACG ATGAAGTC      8580
ACAGATAATT ACAGATGAGC TGTTCATATT TTTTATTATT TTTTCCAATT CCTGCACT      8640
AAAAAGAAGC ACTTTACGGA ACCGTGTCTG AGTATCTGTG GGAATTTAG GTACTTTT      8700
CCGACGTCAG GAAAAATAAG TGTCGCCTAC ATAAGAGCCC GGTGCTATCG TGCTGTCA      8760
CTTTCTTGTT GCCTTCGATG TACGGCGTCC TGGCTCATTA CTACTCCTTC ATCAGTAG      8820
CCAGCGTTAT GGTTAATTTT AAGCATCATA ACGCCGTGCA GCTGTTATGT GCACGGAC      8880
GAGACGCACT GCCGGATGGG AACGTTTAAC CCATCATGCG TCGTATCACG CGAACTAC      8940
GGCATACGCC GTGTTGATGG CTACATCGCA AAGAAAGTCC CTAGTGTTAC ATCGATAC      9000
TGCCGTGACA GCCGTGGCCC TGCAGCTCAT GCCTGTTGAG ATCGTCCGCA AGCTAGAT      9060
GTCGGACTGG GTGCGGGGTG CCTGGATCGT GTCAGAGACT TTTCCAACTA GCGACCCC      9120
AGGAGTTTGG AGCGACGATG ACTCCTCGAT GGGTGGAAGT GATGATTGAT GATGAGAA      9180
```

| | |
|---|---|
| TGACAAGAAA GACGAGAGAG AAATTTAGAG CTGTCATTGT AGAATTAGTC TAGATTCC | 9240 |
| ATAATAAACA GTATCGATTT TGAAACCTAA TTGACGTGTG ATCGATTTTT AAACCTCT | 9300 |
| GTTGTGTGAT TGATTGGTAT GTGGGGGGAT CCGATTTCAA AGGGGGGTAC TTATCGGG | 9360 |
| TTGATGTGTC ATGGACGCAG TTTTGAGCGA TTTTCCGGGA ATACCGGATA TTACGAAT | 9420 |
| CTGGTAGTGA CGTAGATAAT AAAATTATAA TGCGATTAAT TTTTGGTGCG TTGATTAT | 9480 |
| TTTTAGCATA TGTGTATCAT TATGAGGTGA ATGGAACAGA ATTACGCTGC AGATGTCT | 9540 |
| ATAGAAAATG GCCGCCTAAT AAAATTATAT TGGGTAATTA TTGGCTTCAT CGCGATCC | 9600 |
| GAGGGCCCGG ATGCGATAAA AATGAACATT TATTGTATCC AGACGGAAGG AAACCGCC | 9660 |
| GACCTGGAGT ATGTTTATCG CCCGATCACC TCTTCTCAAA ATGGTTAGAC AAACACAA | 9720 |
| ATAATAGGTG GTATAATGTT AACATAACGA AATCACCAGG ACCGAGACGA ATAAATAT | 9780 |
| CCTTGATAGG TGTTAGAGGA TAATATTTAA TGTATGTTTT CAAACAGACA AGTTCGTT | 9840 |
| AACAAAATAT TACAGTATGT GTTTAATATG GTGCTAACAT GGTTCACCA TCCGGTTT | 9900 |
| AACTCGCATA TCAATCTGTT ATCGGTACGA CACCTGTCAT TAATCGCATA TATGTTAC | 9960 |
| ACCATATGTC CCCTAGCCGT CCATGTTTTA GAACTAGAAG ATTACGACAG GCGCTGC | 10020 |
| TGCAACAACC AAATTCTGTT GAATACCCTG CCGGTCGGAA CCGAATTGCT TAAGCCA | 10080 |
| GCAGCGAGCG AAAGCTGCAA TCGTCAGGAA GTGCTGGCTA TTTTAAAGGA CAAGGGA | 10140 |
| AAGTGTCTCA ATCCTAACGC GCAAGCCGTG CGTCGTCACA TCAACCGGCT ATTTTTT | 10200 |
| TTAATCTTAG ACGAGGAACA ACGCATTTAC GACGTAGTGT CTACCAATAT TGAGTTC | 10260 |
| GCCTGGCCAG TCCCTACGGC CTACAAAGCC TTTCTTTGGA AATACGCCAA GAGACTG | 10320 |
| TACCACCACT TCAGACTGCG CTGGTGATCA TGTCCCTATT TTACCGTGCG GTAGCTC | 10380 |
| GCACGCTAAG CGCTTTGGTG TGGTACAGCA CTAGCATCCT CGCAGAGATT AACGAAA | 10440 |
| CCTGCTCCTC ATCTTCTGCG GATCACGAAG ACTGCGAGGA ACCGGACGAG ATCGTTC | 10500 |
| AAGAGCAAGA CTATCGGGCT CTGCTGGCCT TTTCCCTAGT GATTTGCGGT ACGCTCC | 10560 |
| TCACTTGTGT GATCTGAGAC GTCATGCTGG TAGCGTTTAT GAGTCGGGCG GTGGCCG | 10620 |
| CGCCGCATTT CCTAACCCGC GCAGCATGTT GCGCTTGCTG TTCACGCTCG TCCTGCT | 10680 |
| CCTCCACGGG CAGTCTGTCG GCGCTAGCCG CGACTATGTG CATGTTCGGC TACTGAG | 10740 |
| CCGAGGCGAC CCCCTGGTCT TCAAGCACAC TTTCTCGGGT GTGCGTCGAC CCTTCAC | 10800 |
| GCTAGGCTGG GCTGCGTGTC GCGACTGGGA CAGTATGCAT TGCACACCCT TCTGGTC | 10860 |
| CGATCTGGAG CAGATGACCG ACTCGGTGCG GCGTTACAGC ACGGTGAGCC CCGGCAA | 10920 |
| AGTGACGCTT CAGCTTCACG GGAACCAAAC CGTACAGCCG TCGTTTCTAA GCTTTAC | 10980 |
| CCGCCTGCAG CTAGAACCCG TGGTGGAAAA TGTTGGCCTC TACGTGGCCT ACGTGGT | 11040 |
| CGACGGCGAA CGCCCACAAC AGTTTTTTAC ACCGCAGGTA GACGTGGTAC GCTTTGC | 11100 |
| ATATCTAGAA ACACTCTCCC GGATCGTGGA ACCGTTAGAA TCAGGTCGCC TGGCAGT | 11160 |
| ATTTGATACG CCTGACCTAG CTCTGGCGCC CGATTTAGTA AGCAGCCTCT TCGTGGC | 11220 |
| ACACGGCGAG ACCGACTTTT ACATGAACTG GACGCTGCGT CGCAGTCAGA CCCACTA | 11280 |
| GGAGGAGATG GCCTTACAGG TGGAGATTCT AAAACCCCGC GGCGTACGTC ACCGCGC | 11340 |
| TATCCACCAT CCGAAGCTAC AGCCGGGCGT TGGCCTGTGG ATAGATTTCT GCGTGTA | 11400 |
| CTACAACGCG CGCCTGACCC GCGGCTACGT ACGATACACC CTGTCACCGA AAGCGCG | 11460 |
| GCCCGCAAAA GCAGAGGGTT GGCTGGTGTC ACTAGACAGA TTCATCGTGC AGTACCT | 11520 |
| CACATTGCTG ATTACAATGA TGGCGGCGAT ATGGGCTCGC GTTTTGATAA CCTACCT | 11580 |

| | |
|---|---|
| GTCGCGGCGT CGGTAGAGGC TTGCGGAAAC CACGTCCTCG TCACACGTCG TTCGCGG | 11640 |
| TAGCAAGAAA TCCACGTCGC CACATCTCGA GAATGCCGGC CTTGCGGGGT CCCCTTC | 11700 |
| CAACATTCCT GGCCCTGGTC GCGTTCGGGT TGCTGCTTCA GATAGACCTC AGCGACG | 11760 |
| CGAATGTGAC CAGCAGCACA AAAGTCCCTA CTAGCACCAG CAACAGAAAT AACGTCG | 11820 |
| ACGCCACGAG TAGCGGACCC ACAACCGGGA TCAACATGAC CACCACCCAC GAGTCTT | 11880 |
| TTCACAACGT GCGCAATAAC GAGATCATGA AAGTGCTGGC TATCCTCTTC TACATCG | 11940 |
| CAGGCACCTC CATTTTCAGC TTCATAGCGG TACTGATCGC GGTAGTTTAC TCCTCGT | 12000 |
| GCAAGCACCC GGGCCGCTTT CGTTTCGCCG ACGAAGAGGC CGTCAACCTG TTGGACG | 12060 |
| CGGACGACAG TGGCGGCAGC AGCCCGTTTG GCAGCGGTTC CCGACGAGGT TCTCAGA | 12120 |
| CCGCCGGATT TTGTTCCTCG AGCCCTTATC AGCGGTTGGA AACTCGGGAC TGGGACG | 12180 |
| AGGAGGAGGC GTCCGCGGCC CGCGAGCGCA TGAAACATGA TCCTGAGAAC GTCATCT | 12240 |
| TCAGAAAGGA TGGCAACTTG GACACGTCGT TCGTGAATCC CAATTATGGG AGAGGCT | 12300 |
| CTTTGACCAT CGAATCTCAC CTCTCGGACA ATGAGGAGGA CCCCATCAGG TACTACG | 12360 |
| CGGTGTACGA TGAACTGACC GCCTCGGAAA TGGAAGAACC TTCGAACAGC ACCAGCT | 12420 |
| AGATTCCCAA ACTAATGAAA GTTGCCATGC AACCCGTCTC GCTCAGAGAT CCCGAGT | 12480 |
| ACTAGGCTTT TTTTTTTGTC TTTCGGTTCC AACTCTTTCC CCGCCCCATC ACCTCGC | 12540 |
| TACTATGTGT ATGATGTCTC ATAATAAAGC TTTCTTTCTC AGTCTGCAAC ATGCAGC | 12600 |
| GTCGGGTGTG GCTGTCTGTT TGTCTGTGCG CCGTGGTGCT GGGTCAGTGC CAGCGGG | 12660 |
| CCGCGGAAAA AAACGATTAT TACCGAGTAC CGCATTACTG GGACGCGTGC TCTCGCG | 12720 |
| TGCCCGACCA AACCCGTTAC AAGTATGTGG AACAGCTCGT GGACCTCACG TTGAACT | 12780 |
| ACTACGATGC GAGCCACGGC TTGGACAACT TTGACGTGCT CAAGAGGTGA GGGTACG | 12840 |
| TAAAGGTGCA TGACAACGGG AAGGTAAGGG CGAACGGGTA ACGGCTAAGT AACCGCA | 12900 |
| GGTATGAAAT GACGTTTGGA ACCTGTGCTT GCAGAATCAA CGTGACCGAG GTGTCGT | 12960 |
| TCATCAGCGA CTTTAGACGT CAGAACCGTC GCGGCGGCAC CAACAAAAGG ACCACGT | 13020 |
| ACGCCGCCGG TTCGCTGGCG CCACACGCCC GGAGCCTCGA GTTCAGCGTG CGGCTCT | 13080 |
| CCAACTAGCC TGCGTCACGG GAAATAATAT GCTGCGGCTT CTGCTTCGTC ACCACTT | 13140 |
| CTGCCTGCTT CTGTGCGCGG TTTGGGCAAC GCCCTGTCTG GCGTCTCCGT GGTCGAC | 13200 |
| AACGGCAAAC CAGAATCCGT CCCCGCCATG GTCTAAACTG ACGTATTCCA AACCGCA | 13260 |
| CGCGGCGACG TTTTACTGTC CTTTTCTCTA TCCCTCGCCC CCACGGTCCC CCTTGCA | 13320 |
| CTCGGGTTC CAGCAGGTAT CAACGGGTCC CGAGTGTCGC AACGAGACCC TGTATCT | 13380 |
| GTACAACCGG GAAGGCCAGA CCTTGGTGGA GAGAAGCTCC ACCTGGGTGA AAAAGGT | 13440 |
| CTGGTATCTG AGCGGTCGCA ACCAGACCAT CCTCCAACGG ATGCCCCAAA CGGCTTC | 13500 |
| ACCGAGCGAC GGAAACGTGC AGATCAGCGT GGAAGACGCC AAGATTTTTG GAGCGCA | 13560 |
| GGTGCCCAAG CAGACCAAGC TGCTACGCTT CGTCGTCAAC GATGGCACGC GTTATCA | 13620 |
| GTGTGTGATG AAGCTGGAGA GCTGGGCCCA CGTCTTCCGG GACTACAGCG TGTCTTT | 13680 |
| GGTGCGATTG ACGTTCACCG AGGCCAATAA CCAGACTTAC ACCTTCTGTA CCCATCC | 13740 |
| TCTCATCATT TGAGCCCGTC GCGCGCGCAG GGAATTTTGA AAACCGCGCG TCATGAG | 13800 |
| CAAAGACCTG ACGCCGTTCT TGACGACGTT GTGGCTGCTA TTGGGTCACA GCCGCGT | 13860 |
| GCGGGTGCGC GCAGAAGAAT GTTGCGAATT CATAAACGTC AACCACCCGC CGGAACG | 13920 |

| | |
|---|---|
| TTACGATTTC AAAATGTGCA ATCGCTTCAC CGTCGCGTAC GTATTTTCAT GATTGTC | 13980 |
| GTTCTGTGGT GCGTCTGGAT TTGTCTCTCG ACGTTTCTGA TAGCCATGTT CCATCGA | 14040 |
| TCCTCGGGAA TGCCAGAGTA GATTTTCATG AATCCACAGG CTGCGGTGTC CGGACGG | 14100 |
| AGTCTGCTAC AGTCCCGAGA AAACGGCTGA GATTCGCGGG ATCGTCACCA CCATGAC | 14160 |
| TTCATTGACA CGCCAGGTCG TACACAACAA ACTGACGAGC TGCAACTACA ATCCGTA | 14220 |
| CTCTTCCTCG AGGGCCTTAC AGCCTATGGG AGAGTAAGAC AGAGAGGGAC AAAACAT | 14280 |
| TAAAAAAAAA AGTCTAATTT CACGTTTTGT ACCCCCCTTC CCCTCCGTGT TGTAGCC | 14340 |
| CGGCCGCGGC GATCTCCTAG TAACACTCGT CCGACACTTC CACCATCTCC AGCTCGG | 14400 |
| GCGGTTCGGC ATCCTCTACC AGCGGCGTCG TCTCATCTTT GCCGCAGCAG CGGACGC | 14460 |
| CCTTCTCCAG GCAGAACGCC ACCAGCTGCC GCCGAACGTA CCACAGGTAC ACGTGCA | 14520 |
| CTGCGAACAG GACTACGGAG GTCATGACCA CCACGACGCA CACGGGAATC CAGGGAT | 14580 |
| GATTGTTGCT GGAACTCATG GCTATCGCCA CCGACGTGCC CGCGTCTGTC TCACCGC | 14640 |
| TCGCCCGATG TCGCGCGGCT TGTTATACGC TAGCCCGTCG CCGCCTCGGG GCACGGT | 14700 |
| CTCCTACCCA CGTAACTTCC TCCGTGACTT AAAGTCGCGT GTGGTAGATC TCCTGCT | 14760 |
| TGGACGAACC GTCCGGCAGG ATAGCGGTTA AGGATTCGGT GCTAAGGCCG TGTCGCC | 14820 |
| GTCGAATGCT ACGTTGCAAC AGCTTCGACG GACGGCCATC CCCTCTCTCA TCGCAAT | 14880 |
| AAAACACCAG CAGCGCGCAC GACGCGATCA CGGTGACACC CATGATTAGA CCCACGC | 14940 |
| TAGCCAGCCC CGCTAGCGTA TCTAGCGCCA TCCCGTTCGC TCCCGTTGTC TCCTGAG | 15000 |
| AGCAACTTCT CGGTCCCCGT TTTCAACAGT TTTTGTTTCC TTCTCCGCGA CTAGATG | 15060 |
| ACGCCCGCGG TCTTTCCGGC CGTGCTCTAC CTCCTGGCGC TTGTCGTCTG GGTTGAG | 15120 |
| TTCTGCCTCG TCGCCGTAGC CGTCGTCGAG CGCGAGATCG CCTGGGCGCT GCTGCTG | 15180 |
| ATGCTGGTCG TTGGCCTGAT GGTGGAAGTC GGCGCCGCCG CCGCTTGGAC CTTCGTG | 15240 |
| TGTCTTGCCT ATCAGCGCTC CTTCCCCGTG CTTACGGCCT TCCCCTGAAA CCCACGT | 15300 |
| CCGACCGTCC CAAAAACGCC GGTGTTAACA CAGGAAAAAA AGAAACCACG CAGGAAC | 15360 |
| GCAGGAACCA CGCGGAACAT GGGACACTAT CTGGAAATCC TGTTCAACGT CATCGTC | 15420 |
| ACTCTGCTGC TCGGCGTCAT GGTCAGTATC GTCGCTTGGT ACTTCACGTG AACCACC | 15480 |
| GTCCCGGTTT AAAACCATC ATCGACGGCC GTTATAAAGC CACCCGGACA CGCGCCG | 15540 |
| CACTTGCCTA CGGCGCTGCT TCAGGGAAAC TCCTCTTCCT TCTGCTCTTC CTCCTTC | 15600 |
| GCAGGGATCG TTTCCCTCGA CCAGGGACTC GCCGAAGCAA CCGCCGGAGC AACCTGG | 15660 |
| AGTCGCGGCA TGACGGCGCC CAAGTGTGTC ACCACCAGTA CTTATCTGGT CAAGACC | 15720 |
| GAACAGCCCT GGTGGCCCGA CAACGCCATC AGGAGATGGT GGATCAGTGT TGCTATC | 15780 |
| ATCTTCATCG GAGTCTGTCT GGTGGCCCTG ATGTACTTTA CGCAGCAGCA GGCACGC | 15840 |
| GGGAGCAGCA GCGGCTAGAC AAGTCTCTGG CGGCTACAGC TCCAAGCGCC GTAGCCG | 15900 |
| CGCCTGCCGA TCGCGACGTC GTGGACCATC GAACAGAGAC TCACGCGTAC GAGACCC | 15960 |
| GGTACGCCAC GCGGTGCCTA ACGCGGTATA CCACACCCGT ACGGTCTGCA GTGCGGC | 16020 |
| CAACGTGTGG AAAACGCGTT GCGTCGCAGA GTCCGCCACG TTCCTGTCTT GTCGCTC | 16080 |
| AATCGTCTCC CGCACACCCC CCGCGACACC CAGAGGGCGG GTGAGCCAAG TATTCTT | 16140 |
| GCCGTTCTTT GTTCCATAGC CCATAAATTG TTGATTCCGG AGCTCGTTGG CGCGGAA | 16200 |
| GCCGGATAAG GGGAGCAACA ACCGTTGGCG AAAGCCGTCC CGCTCATTCA GTCCGGG | 16260 |
| CGCGTCCAGT CGGACGTGTG ACCGTTGGGC AACGGAACGG CGTTTCACTG CCAAAAT | 16320 |

-continued

```
ATCGGGTAGT GTACGAGACG TCGGCGGTGC AGAATGCGAC TCGCGGCGTA GCTCGCC        16380

GCTATGCGGC TCGTCGCCGT GTGGCGCGGC CTGGCCGGCT GTCTGCGTCC AGATCTG        16440

GCCTTTTGGT TCCTCTGGCT GCTGCTGCGT GTGTGCTTTG GTAGACGCGG TGGCAGT        16500

CGGTCTGCGG TAAGTGAGGA TGTCGCCGAG CAAACGCACT TGCGGCGCGT GGGCGGC        16560

CGTGTCATTG TAGGTTCGTT GCCAGATGGC AAGTGCTGTC AACAGCAGGC GTTGTGG        16620

GTCGGTGTAT TTTTGTGGGT TGCGGTGAGA GTCGGCACTC GGTGTTTTGT GAGTCAT        16680

AACTATCTGT GTTGCTTTGA GCAGCGTCCA GAACAGCGAC GCGACTTTGG GGATGGC        16740

GTGCTCACCT CCGCGGAGAG CGCCGCCGGA CCTGCTCGTC AGCAGCGAGC TACGCAG        16800

GAATATCTGG AGGAGAGTTA CGTGTGTCAC AGGAGAGCGC GGGTCTCCGG CGGTAAC        16860

GGCGGTGTCG TCGACACGTG TGCGGCCTGT TGTGCTCTGC GGAAAAGTGC CGGTCTC        16920

GACCGTGGAC GAAAAAGAGA ACGCAGCAGC TACCGCTGGC GGCGGCGGCG TTAATGC        16980

CGTTGATGTT CGACGTTGTG AGCACTCGGA AACAGCGGTG AGGCAGAAGG TCGATTC        17040

AGGGAACGAC AGTCGATGCG TGGTAGCCGC AGCAGGTGAG GTTGGGGCGG ACAACGT        17100

GCGGATTGTG GCGAGAACGT CGTCCTCCCC TTCTTCACCG CCCCACCCAC CCTCGGT        17160

TGTTTCTTTT TTCTTGTGTC CTGCAGATAG TTCCACGGAC AGCGACGGCA AGTCCAT        17220

CAGCGGTGTG CAAGTGGTGG AACACGACGA AGATATCATC GCGCCGCAGA GTTTGTG        17280

CACGGCGTTC AAGGAAGCCC TCTGGGATGT GGCTCTGTTG GAAGTGCCGC GTTGGGC        17340

GCAGGGCTGG AAGAGGTGGC GCAACAGCGA GGCCGGGCGT CGATGGAGTG CTGGGTC        17400

GTCGGCTTCC AGCTTGTCTG ACTTGGCGGG CGAGGCCGTT GGAGAATTGG TGGGATC        17460

CGTCGCGTAC GTGATCCTTG AACGTCTGTG GTTGGCAGCC AGAGGTTGGG TGTGCGA        17520

AGGTGTGGAA GCCGAGGAGG CCATGTCGCG GCGGCGACAG CGCATGCTGT GGCGTAT        17580

TCTCTCGTGG AGGCGACGGC GAATGCAGCA GACGGTGTTC GATGGAGATG GCGTGCG        17640

AAGAAAGCGC CGTGTTGTGA GCAGACGACG TAGGATGCGG GACGTCGGAG CACATGG        17700

ATGTGTGGTG GCAGATGGCG GTGTCCGCTG GTGTCTGCTG CGGCAGTGCA TAGACGA        17760

AACATGTCGC TGTGAAGAGA TAGAGTGTGA GCATAGCTGC ATGCAGCGTT GCGTGTA        17820

GCGGGGGGGA TTAAGACGTT AATAAAGAAT AGCGGCGGTT CTGATAGGGC GACCGCT        17880

GTGAGCTGCG TGTGCGTGTG GTTTGTGGAG TCCCCGCCGC CCCCGGTCCC GTGTCCG        17940

GCAAAGCCCC CCGGNTCCGC ACACTCCTGG CCGCGCAACC CTCGTCGCTG CAAAAGC        18000

CCGTCCCCGC ACACCCCCGC GACCGCCGGT CCCGCGAGTC CCCGTCCCCG CCGCAAA        18060

CCCCCGTCCT CGCCGCAAAC ACCCCCGTCA CCCCCGTCCC TCAGNCCGGG TCCGCGA        18120

CCCGTTCCCA GCGTAATCCC CGTACCCGCA ACGNCCCGGN CCCACCGTCG TCCCGCA        18180

CCCCCGTCCC CCAGCCCGGT GCCCAGCGTG CGAAAAAAGC TCCGTCCCTC ACACCCG        18240

AAAGATCCCT CAGCGCGGTG AAACCCCGTC CCCAGCGCCG TGCCGCTGAC AAAGACC        18300

GGACGACACG CACAGGCA                                                   18318
```

(2) INFORMATION FOR SEQ ID NO: 7:

(i) SEQUENCE CHARACTERISTICS:
        (A) LENGTH: 257 amino acids
        (B) TYPE: amino acid
        (D) TOPOLOGY: linear (ii) MOLECULE TYPE: protein (vii) IMMEDIATE SOURCE:
              (B) CLONE: tol.01

(ix) FEATURE:
             (A) NAME/KEY: Protein
             (B) LOCATION: 1..257
             (D) OTHER INFORMATION: /label= UL133

(xi) SEQUENCE DESCRIPTION: SEQ ID NO: 7:

Met Gly Cys Asp Val His Asp Pro Ser Trp Gln Cys Gln Trp Gly Val
 1               5                  10                  15

Pro Thr Ile Ile Val Ala Trp Ile Thr Cys Ala Ala Leu Gly Ile Trp
            20                  25                  30

Cys Leu Ala Gly Ser Ser Ala Asp Val Ser Ser Gly Pro Gly Ile Ala
        35                  40                  45

Ala Val Val Gly Cys Ser Val Phe Met Ile Phe Leu Cys Ala Tyr Leu
    50                  55                  60

Ile Arg Tyr Arg Glu Phe Phe Lys Asp Ser Val Ile Asp Leu Leu Thr
65                  70                  75                  80

Cys Arg Trp Val Arg Tyr Cys Ser Cys Ser Cys Lys Cys Ser Cys Lys
                85                  90                  95

Cys Ile Ser Gly Pro Cys Ser Arg Cys Cys Ser Ala Cys Tyr Lys Glu
            100                 105                 110

Thr Met Ile Tyr Asp Met Val Gln Tyr Gly His Arg Arg Arg Pro Gly
        115                 120                 125

His Gly Asp Asp Pro Asp Arg Val Ile Cys Glu Ile Val Glu Ser Pro
    130                 135                 140

Pro Val Ser Ala Pro Thr Val Ser Val Pro Pro Ser Glu Glu Ser
145                 150                 155                 160

His Gln Pro Val Ile Pro Pro Gln Pro Ala Pro Thr Ser Glu Pro
                165                 170                 175

Lys Pro Lys Lys Gly Arg Ala Lys Asp Lys Pro Lys Gly Arg Pro Lys
            180                 185                 190

Asp Lys Pro Pro Cys Glu Pro Thr Val Ser Ser Gln Pro Pro Ser Gln
            195                 200                 205

Pro Thr Ala Met Pro Gly Gly Pro Pro Asp Ala Pro Pro Ala Met
210                 215                 220

Pro Gln Met Pro Pro Gly Val Ala Glu Ala Val Gln Ala Ala Val Gln
225                 230                 235                 240

Ala Ala Val Ala Ala Ala Leu Gln Gln Gln Gln Gln His Gln Thr Gly
            245                 250                 255

Thr (2) INFORMATION FOR SEQ ID NO: 8:

(i) SEQUENCE CHARACTERISTICS:
        (A) LENGTH: 175 amino acids
        (B) TYPE: amino acid
        (D) TOPOLOGY: linear (ii) MOLECULE TYPE: protein (vii) IMMEDIATE SOURCE:
          (B) CLONE: tol.02

(ix) FEATURE:
         (A) NAME/KEY: Protein
         (B) LOCATION: 1..175
         (D) OTHER INFORMATION: /label= UL134

(xi) SEQUENCE DESCRIPTION: SEQ ID NO: 8:

```
Met Ala Arg Thr Arg Glu Ala Ser Pro Val Pro Pro Arg Ser Pro Met
1               5                  10                  15

Pro Ser His Ile His Thr Met Ile Phe Ser Pro Ala Trp Asn Leu Lys
            20                  25                  30

Leu Arg Val Gly Lys Gly Arg Cys Thr Asp Ile Tyr Ala Leu Asp Phe
        35                  40                  45

Trp Lys Arg His Phe Leu Ala Arg Asn Val Phe Ile Val Gln Thr Leu
    50                  55                  60

Arg Lys Glu Met Cys Ala Lys Ser Glu Asn Ser Leu Ser His Arg Gly
65                  70                  75                  80

Arg Val Thr Phe Arg Ser Asp Ala Ala Val Val Glu Pro Arg
                85                  90                  95

Pro Arg Pro Pro Ala Arg Gln Leu Val Pro Pro Arg Pro Arg Arg Val
            100                 105                 110

Ala Ser Ala Ala Trp Arg Gly Glu Ala Arg Arg Ala Asp Arg Arg Ala
        115                 120                 125

Leu Pro Ser Ala Ala Thr Val Val Asn Ser Pro Ser Val Arg Thr
130                 135                 140

Glu Val Cys Leu Ser Val Tyr Pro Ser Val Tyr Leu Ser Pro Tyr Leu
145                 150                 155                 160

Ser Ser Val Trp Val Pro Met Ser Val Leu Ala Ala Ala Val Gly
                165                 170                 175

(2) INFORMATION FOR SEQ ID NO: 9:

(i) SEQUENCE CHARACTERISTICS:
        (A) LENGTH: 328 amino acids
        (B) TYPE: amino acid
        (D) TOPOLOGY: linear (ii) MOLECULE TYPE: protein (vii) IMMEDIATE SOURCE:
        (B) CLONE: tol.03

(ix) FEATURE:
        (A) NAME/KEY: Protein
        (B) LOCATION: 1..328
        (D) OTHER INFORMATION: /label= UL135

(xi) SEQUENCE DESCRIPTION: SEQ ID NO: 9:

Met Ser Val His Arg Pro Phe Pro Thr Arg Ser Leu Arg Phe Gln Ala
1               5                   10                  15

Gly Glu Lys Ile Met Val Trp Ile Trp Leu Gly Ile Gly Leu Leu Gly
            20                  25                  30

Gly Thr Gly Leu Ala Ser Leu Val Leu Ala Ile Ser Leu Phe Thr Gln
        35                  40                  45

Arg Arg Gly Arg Lys Arg Ser Asp Glu Thr Ser Ser Arg Gly Arg Leu
    50                  55                  60

Pro Gly Ala Ala Ser Asp Lys Arg Gly Ala Cys Ala Cys Cys Tyr Arg
65                  70                  75                  80

Asn Pro Lys Glu Asp Val Val Glu Pro Leu Asp Leu Glu Leu Gly Leu
                85                  90                  95

Met Arg Val Asp Thr His Pro Pro Thr Pro Gln Val Pro Arg Cys Thr
            100                 105                 110

Ser Leu Tyr Ile Gly Glu Asp Gly Leu Pro Ile Asp Lys Pro Glu Phe
        115                 120                 125

Pro Pro Ala Arg Phe Glu Ile Pro Asp Val Ser Thr Pro Gly Thr Pro
```

-continued

```
            130                 135                 140
Thr Ser Ile Gly Arg Ser Pro Ser His Cys Ser Ser Ser Ser Leu
145                 150                 155                 160

Ser Ser Ser Thr Ser Val Asp Thr Val Leu Tyr Gln Pro Pro Ser
                165                 170                 175

Trp Lys Pro Pro Pro Pro Gly Arg Lys Arg Pro Pro Thr Pro
            180                 185                 190

Pro Val Arg Ala Pro Thr Thr Arg Leu Ser Ser His Arg Pro Pro Thr
            195                 200                 205

Pro Ile Pro Ala Pro Arg Lys Asn Leu Ser Thr Pro Pro Thr Lys Lys
            210                 215                 220

Thr Pro Pro Pro Thr Lys Pro Lys Pro Val Gly Trp Thr Pro Val
225                 230                 235                 240

Thr Pro Arg Pro Phe Pro Lys Thr Pro Thr Pro Gln Lys Pro Pro Arg
                245                 250                 255

Asn Pro Arg Leu Pro Arg Thr Val Gly Leu Glu Asn Leu Ser Lys Val
                260                 265                 270

Gly Leu Ser Cys Pro Cys Pro Arg Pro Arg Thr Pro Thr Glu Pro Thr
                275                 280                 285

Thr Leu Pro Ile Val Ser Val Ser Glu Leu Ala Pro Pro Arg Trp
290                 295                 300

Ser Asp Ile Glu Glu Leu Leu Glu Gln Ala Val Gln Ser Val Met Lys
305                 310                 315                 320

Asp Ala Glu Ser Met Gln Met Thr
                325
```

(2) INFORMATION FOR SEQ ID NO: 10:

(i) SEQUENCE CHARACTERISTICS:
        (A) LENGTH: 240 amino acids
        (B) TYPE: amino acid
        (D) TOPOLOGY: linear (ii) MOLECULE TYPE: protein (vii) IMMEDIATE SOURCE:
        (B) CLONE: tol.04

(ix) FEATURE:
        (A) NAME/KEY: Protein
        (B) LOCATION: 1..240
        (D) OTHER INFORMATION: /label= UL136

(xi) SEQUENCE DESCRIPTION: SEQ ID NO: 10:

```
Met Ser Val Lys Gly Val Glu Met Pro Glu Met Thr Trp Asp Leu Asp
1               5                   10                  15

Val Arg Asn Lys Trp Arg Arg Lys Ala Leu Ser Arg Ile His Arg
                20                  25                  30

Phe Trp Glu Cys Arg Leu Arg Val Trp Trp Leu Ser Asp Ala Gly Val
            35                  40                  45

Arg Glu Thr Asp Pro Pro Arg Pro Arg Arg Pro Thr Trp Met Thr
50                  55                  60

Ala Val Phe His Val Ile Cys Ala Val Leu Leu Thr Leu Met Ile Met
65                  70                  75                  80

Ala Ile Gly Ala Leu Ile Ala Tyr Leu Arg Tyr Tyr His Gln Asp Ser
                85                  90                  95

Trp Arg Asp Met Leu His Asp Leu Phe Cys Gly Cys His Tyr Pro Glu
                100                 105                 110
```

```
Lys Cys Arg Arg His His Glu Arg Gln Arg Arg Arg Gln Ala Met
        115                 120                 125

Asp Val Pro Asp Pro Glu Leu Gly Asp Pro Ala Arg Arg Pro Leu Asn
130                 135                 140

Gly Ala Met Tyr Tyr Gly Ser Gly Cys Arg Phe Asp Thr Val Glu Met
145                 150                 155                 160

Val Asp Glu Thr Arg Pro Ala Pro Pro Ala Leu Ser Ser Pro Glu Thr
                165                 170                 175

Gly Asp Ser Asn Asp Asp Ala Val Ala Gly Gly Gly Ala Gly Gly
                180                 185                 190

Val Thr Ser Pro Ala Thr Arg Thr Thr Ser Pro Asn Ala Leu Leu Pro
        195                 200                 205

Glu Trp Met Asp Ala Val His Val Ala Val Gln Ala Ala Val Gln Ala
        210                 215                 220

Thr Val Gln Val Ser Gly Pro Arg Glu Asn Ala Val Ser Pro Ala Thr
225                 230                 235                 240

(2) INFORMATION FOR SEQ ID NO: 11:

(i) SEQUENCE CHARACTERISTICS:
        (A) LENGTH: 96 amino acids
        (B) TYPE: amino acid
        (D) TOPOLOGY: linear (ii) MOLECULE TYPE: protein (vii) IMMEDIATE SOURCE:
        (B) CLONE: tol.05

(ix) FEATURE:
        (A) NAME/KEY: Protein
        (B) LOCATION: 1..96
        (D) OTHER INFORMATION: /label= UL137

(xi) SEQUENCE DESCRIPTION: SEQ ID NO: 11:

Met Ala Thr Ile Ser Thr Ser Ile Thr Pro Met Met Gly Asn Pro Thr
1               5                   10                  15

Phe Ser Gly Arg Ser Ser Met Val Thr Val Leu Cys Pro Asp Leu Arg
                20                  25                  30

Pro Ser Leu Ser Leu Leu Tyr Ser Thr Arg Ala Gly Thr Ala Pro Ser
            35                  40                  45

Thr Leu Leu Arg Ser Gly Arg Tyr Gly Val Leu Pro Arg Ala Thr Tyr
        50                  55                  60

Leu His Gly Arg Leu Asn Gly Gly Leu Asp Arg His Met His Arg Ile
65                  70                  75                  80

His Pro Phe Trp Gln Gln Cys Val Arg Arg Arg Thr Ser Arg Gly
                85                  90                  95

(2) INFORMATION FOR SEQ ID NO: 12:

(i) SEQUENCE CHARACTERISTICS:
        (A) LENGTH: 169 amino acids
        (B) TYPE: amino acid
        (D) TOPOLOGY: linear (ii) MOLECULE TYPE: protein (vii) IMMEDIATE SOURCE:
        (B) CLONE: tol.06

(ix) FEATURE:
        (A) NAME/KEY: Protein
        (B) LOCATION: 1..169
        (D) OTHER INFORMATION: /label= UL138
```

(xi) SEQUENCE DESCRIPTION: SEQ ID NO: 12:

```
Met Asp Asp Leu Pro Leu Asn Val Gly Leu Pro Ile Ile Gly Val Met
1               5                   10                  15

Leu Val Leu Ile Val Ala Ile Leu Cys Tyr Leu Ala Tyr His Trp His
            20                  25                  30

Asp Thr Phe Lys Leu Val Arg Met Phe Leu Ser Tyr Arg Trp Leu Ile
        35                  40                  45

Arg Cys Cys Glu Leu Tyr Gly Glu Tyr Glu Arg Arg Phe Ala Asp Leu
    50                  55                  60

Ser Ser Leu Gly Leu Gly Ala Val Arg Arg Glu Ser Asp Arg Arg Tyr
65                  70                  75                  80

Arg Phe Ser Glu Arg Pro Asp Glu Ile Leu Val Arg Trp Glu Glu Val
                85                  90                  95

Ser Ser Gln Cys Ser Tyr Ala Ser Ser Arg Ile Thr Asp Arg Arg Val
            100                 105                 110

Gly Ser Ser Ser Ser Ser Val His Val Ala Ser Gln Arg Asn Ser
            115                 120                 125

Val Pro Pro Asp Met Ala Val Thr Ala Pro Leu Thr Asp Val Asp
    130                 135                 140

Leu Leu Lys Pro Val Thr Gly Ser Ala Thr Gln Phe Thr Thr Val Ala
145                 150                 155                 160

Met Val His Tyr His Gln Glu Tyr Thr
                165
```

(2) INFORMATION FOR SEQ ID NO: 13:

(i) SEQUENCE CHARACTERISTICS:
        (A) LENGTH: 135 amino acids
        (B) TYPE: amino acid
        (D) TOPOLOGY: linear (ii) MOLECULE TYPE: protein (vii) IMMEDIATE SOURCE:
       (B) CLONE: tol.07

(ix) FEATURE:
       (A) NAME/KEY: Protein
       (B) LOCATION: 1..135
       (D) OTHER INFORMATION: /label= UL139

(xi) SEQUENCE DESCRIPTION: SEQ ID NO: 13:

```
Met Leu Trp Ile Leu Val Leu Phe Ala Leu Ala Ala Ser Ala Ser Glu
1               5                   10                  15

Thr Thr Thr Gly Thr Ser Ser Asn Ser Ser Gln Ser Thr Ser Ala Thr
            20                  25                  30

Ala Asn Thr Thr Val Ser Thr Cys Ile Asn Ala Ser Asn Gly Ser Ser
        35                  40                  45

Trp Thr Val Pro Gln Leu Ala Leu Leu Ala Ala Ser Gly Trp Thr Leu
    50                  55                  60

Ser Gly Leu Leu Leu Leu Phe Thr Cys Cys Phe Cys Phe Cys Phe Trp Leu
65                  70                  75                  80

Val Arg Lys Ile Cys Ser Cys Cys Gly Asn Ser Ser Glu Ser Glu Ser
                85                  90                  95

Lys Thr Thr His Ala Tyr Thr Asn Ala Ala Phe Thr Ser Ser Asp Ala
            100                 105                 110

Thr Leu Pro Met Gly Thr Thr Gly Ser Tyr Thr Pro Pro Gln Asp Gly
            115                 120                 125
```

```
Ser Phe Pro Pro Pro Pro Arg
    130                 135
```

(2) INFORMATION FOR SEQ ID NO: 14:

(i) SEQUENCE CHARACTERISTICS:
        (A) LENGTH: 114 amino acids
        (B) TYPE: amino acid
        (D) TOPOLOGY: linear (ii) MOLECULE TYPE: protein (vii) IMMEDIATE SOURCE:
        (B) CLONE: tol.08

(ix) FEATURE:
        (A) NAME/KEY: Protein
        (B) LOCATION: 1..114
        (D) OTHER INFORMATION: /label= UL140

(xi) SEQUENCE DESCRIPTION: SEQ ID NO: 14:

```
Met Thr Pro Ala Gln Thr Asn Ala Thr Thr Thr Val His Pro His Asp
1               5                  10                 15

Ala Lys Asn Gly Ser Gly Gly Ser Ala Leu Pro Thr Leu Val Val Phe
                20                  25                 30

Gly Phe Ile Val Thr Leu Leu Phe Leu Phe Met Leu Tyr Phe Trp
            35                  40                  45

Asn Asn Asp Val Phe Arg Lys Leu Leu Arg Ala Leu Gly Ser Ser Ala
        50                  55                  60

Val Ala Thr Ala Ser Thr Arg Gly Lys Thr Arg Ser Ser Thr Val Val
65                  70                  75                  80

His His Val Val Pro Arg Ala Thr Thr Arg Val Val Leu Thr Ala Cys
                85                  90                  95

His Arg Thr Phe Phe Tyr His Pro Arg Pro Met Ala Val Leu Thr Thr
                100                 105                 110

Arg His
```

(2) INFORMATION FOR SEQ ID NO: 15:

(i) SEQUENCE CHARACTERISTICS:
        (A) LENGTH: 425 amino acids
        (B) TYPE: amino acid
        (D) TOPOLOGY: linear (ii) MOLECULE TYPE: protein (vii) IMMEDIATE SOURCE:
        (B) CLONE: tol.09

(ix) FEATURE:
        (A) NAME/KEY: Protein
        (B) LOCATION: 1..425
        (D) OTHER INFORMATION: /label= UL141

(xi) SEQUENCE DESCRIPTION: SEQ ID NO: 15:

```
Met Arg Gln Val Ala Tyr Arg Arg Arg Glu Ser Ser Cys Ala Val
1               5                  10                 15

Leu Val His His Val Gly Arg Asp Gly Asp Gly Glu Gly Glu Ala Ala
                20                  25                 30

Lys Lys Thr Cys Lys Lys Thr Gly Arg Ser Val Ala Gly Ile Pro Gly
                35                  40                  45

Glu Lys Leu Arg Arg Thr Val Val Thr Thr Thr Pro Ala Arg Arg Leu
        50                  55                  60
```

-continued

```
Ser Gly Arg His Thr Glu Gln Glu Gln Ala Gly Met Arg Leu Cys Glu
 65                  70                  75                  80

Lys Gly Lys Lys Arg Ile Ile Met Cys Arg Glu Ser Leu Arg Thr
                 85                  90                  95

Leu Pro Trp Leu Phe Trp Val Leu Leu Ser Cys Pro Arg Leu Leu Glu
                100                 105                 110

Tyr Ser Ser Ser Phe Pro Phe Ala Thr Ala Asp Ile Ala Glu Lys
                115                 120                 125

Met Trp Ala Glu Asn Tyr Glu Thr Thr Ser Pro Ala Pro Val Leu Val
130                 135                 140

Ala Glu Gly Glu Gln Val Thr Ile Pro Cys Thr Val Met Thr His Ser
145                 150                 155                 160

Trp Pro Met Val Ser Ile Arg Ala Arg Phe Cys Arg Ser His Asp Gly
                165                 170                 175

Ser Asp Glu Leu Ile Leu Asp Ala Val Lys Gly His Arg Leu Met Asn
                180                 185                 190

Gly Leu Gln Tyr Arg Leu Pro Tyr Ala Thr Trp Asn Phe Ser Gln Leu
                195                 200                 205

His Leu Gly Gln Ile Phe Ser Leu Thr Phe Asn Val Ser Met Asp Thr
210                 215                 220

Ala Gly Met Tyr Glu Cys Val Leu Arg Asn Tyr Ser His Gly Leu Ile
225                 230                 235                 240

Met Gln Arg Phe Val Ile Leu Thr Gln Leu Glu Thr Leu Ser Arg Pro
                245                 250                 255

Asp Glu Pro Cys Cys Thr Pro Ala Leu Gly Arg Tyr Ser Leu Gly Asp
                260                 265                 270

Gln Ile Trp Ser Pro Thr Pro Trp Arg Leu Arg Asn His Asp Cys Gly
                275                 280                 285

Thr Tyr Arg Gly Phe Gln Arg Asn Tyr Phe Tyr Ile Gly Arg Ala Asp
290                 295                 300

Ala Glu Asp Cys Trp Lys Pro Ala Cys Pro Asp Glu Glu Pro Asp Arg
305                 310                 315                 320

Cys Trp Thr Val Ile Gln Arg Tyr Arg Leu Pro Gly Asp Cys Tyr Arg
                325                 330                 335

Ser Gln Pro His Pro Pro Lys Phe Leu Pro Val Thr Pro Ala Pro Pro
                340                 345                 350

Ala Asp Ile Asp Thr Gly Met Ser Pro Trp Ala Thr Arg Gly Ile Ala
                355                 360                 365

Ala Phe Leu Gly Phe Trp Ser Ile Phe Thr Val Cys Phe Leu Cys Tyr
370                 375                 380

Leu Cys Tyr Leu Gln Cys Cys Gly Arg Trp Cys Pro Thr Pro Gly Arg
385                 390                 395                 400

Gly Arg Arg Gly Gly Glu Gly Tyr Arg Arg Leu Pro Thr Tyr Asp Ser
                405                 410                 415

Tyr Pro Gly Val Arg Lys Met Lys Arg
                420                 425
```

(2) INFORMATION FOR SEQ ID NO: 16:

(i) SEQUENCE CHARACTERISTICS:
        (A) LENGTH: 306 amino acids
        (B) TYPE: amino acid
        (D) TOPOLOGY: linear (ii) MOLECULE TYPE: protein (vii) IMMEDIATE SOURCE:
    (B) CLONE: tol.10

(ix) FEATURE:
    (A) NAME/KEY: Protein
    (B) LOCATION: 1..306
    (D) OTHER INFORMATION: /label= UL142

(xi) SEQUENCE DESCRIPTION: SEQ ID NO: 16:

```
Met Arg Ile Glu Trp Val Trp Trp Leu Phe Gly Tyr Phe Val Ser Ser
 1               5                  10                  15

Val Gly Ser Glu Arg Ser Leu Ser Tyr Arg Tyr His Leu Glu Ser Asn
            20                  25                  30

Ser Ser Thr Asn Val Val Cys Asn Gly Asn Ile Ser Val Phe Val Asn
        35                  40                  45

Gly Thr Leu Gly Val Arg Tyr Asn Ile Thr Val Gly Ile Ser Ser Ser
    50                  55                  60

Leu Leu Ile Gly His Leu Thr Ile Gln Val Leu Glu Ser Trp Phe Thr
65                  70                  75                  80

Pro Trp Val Gln Asn Lys Ser Tyr Asn Lys Gln Pro Leu Gly Asp Thr
                85                  90                  95

Glu Thr Leu Tyr Asn Ile Asp Ser Glu Asn Ile His Arg Val Ser Gln
            100                 105                 110

Tyr Phe His Thr Arg Trp Ile Lys Ser Leu Gln Glu Asn His Thr Cys
        115                 120                 125

Asp Leu Thr Asn Ser Thr Pro Thr Tyr Thr Tyr Gln Val Asn Val Asn
130                 135                 140

Asn Thr Asn Tyr Leu Thr Leu Thr Ser Ser Gly Trp Gln Asp Arg Leu
145                 150                 155                 160

Asn Tyr Thr Val Ile Asn Ser Thr His Phe Asn Leu Thr Glu Ser Asn
                165                 170                 175

Ile Thr Ser Ile Gln Lys Tyr Leu Asn Thr Thr Cys Ile Glu Arg Leu
            180                 185                 190

Arg Asn Tyr Thr Leu Glu Ser Val Tyr Thr Thr Thr Val Pro Gln Asn
        195                 200                 205

Ile Thr Thr Ser Gln His Ala Thr Thr Thr Met His Thr Ile Pro Pro
210                 215                 220

Asn Thr Ile Thr Ile Gln Asn Thr Thr Gln Ser His Thr Val Gln Thr
225                 230                 235                 240

Pro Ser Phe Asn Asp Thr His Asn Val Thr Lys His Thr Leu Asn Ile
                245                 250                 255

Ser Tyr Val Leu Ser Gln Lys Thr Asn Asn Thr Thr Ser Pro Trp Ile
            260                 265                 270

Tyr Ala Ile Pro Met Gly Ala Thr Ala Thr Ile Gly Ala Gly Leu Tyr
        275                 280                 285

Ile Gly Lys His Phe Thr Pro Val Lys Phe Val Tyr Glu Val Trp Arg
        290                 295                 300

Gly Gln
305
```

(2) INFORMATION FOR SEQ ID NO: 17:

(i) SEQUENCE CHARACTERISTICS:
        (A) LENGTH: 92 amino acids
        (B) TYPE: amino acid
        (D) TOPOLOGY: linear (ii) MOLECULE TYPE: protein -continued

```
    (vii) IMMEDIATE SOURCE:
          (B) CLONE: tol.11

(ix) FEATURE:
         (A) NAME/KEY: Protein
         (B) LOCATION: 1..92
         (D) OTHER INFORMATION: /label= UL143

(xi) SEQUENCE DESCRIPTION: SEQ ID NO: 17:

Met Ala Arg Ser Val Lys Thr Ile Arg Ile Gln His Ile Tyr Ser Pro
1               5                  10                  15

Arg Ser Ser Asn Thr Leu Gln His Met Ser Lys Lys Gln Glu Ser Ile
            20                  25                  30

Ala Thr Ile Thr Phe Gly Arg Ile Thr Cys Cys His Pro Leu Ala Ser
        35                  40                  45

Ile Asn Leu Met Phe Asn Gly Ser Cys Thr Val Thr Val Lys Ile Ser
    50                  55                  60

Met Gly Ile Asn Gly Ser Thr Asn Val His Gln Leu Val Ile Val Leu
65                  70                  75                  80

His Leu Gly Asn Arg Cys Gln Pro Trp Arg Gln Val
                85                  90

(2) INFORMATION FOR SEQ ID NO: 18:

(i) SEQUENCE CHARACTERISTICS:
        (A) LENGTH: 176 amino acids
        (B) TYPE: amino acid
        (D) TOPOLOGY: linear (ii) MOLECULE TYPE: protein (vii) IMMEDIATE SOURCE:
          (B) CLONE: tol.12

(ix) FEATURE:
         (A) NAME/KEY: Protein
         (B) LOCATION: 1..176
         (D) OTHER INFORMATION: /label= UL144

(xi) SEQUENCE DESCRIPTION: SEQ ID NO: 18:

Met Lys Pro Leu Ile Met Leu Ile Cys Phe Ala Val Ile Leu Leu Gln
1               5                  10                  15

Leu Gly Val Thr Lys Val Cys Gln His Asn Glu Val Gln Leu Gly Asn
            20                  25                  30

Glu Cys Cys Pro Pro Cys Gly Ser Gly Gln Arg Val Thr Lys Val Cys
        35                  40                  45

Thr Asp Tyr Thr Ser Val Thr Cys Thr Pro Cys Pro Asn Gly Thr Tyr
    50                  55                  60

Val Ser Gly Leu Tyr Asn Cys Thr Asp Cys Thr Gln Cys Asn Val Thr
65                  70                  75                  80

Gln Val Met Ile Arg Asn Cys Ser Thr Asn Asn Thr Val Cys Ala
        85                  90                  95

Pro Lys Asn His Thr Tyr Phe Ser Thr Pro Gly Val Gln His His Lys
        100                 105                 110

Gln Arg Gln Gln Asn His Thr Ala His Ile Thr Val Lys Gln Gly Lys
        115                 120                 125

Ser Gly Arg His Thr Leu Ala Trp Leu Ser Leu Phe Ile Phe Leu Val
        130                 135                 140

Gly Ile Ile Leu Leu Ile Leu Tyr Leu Ile Ala Ala Tyr Arg Ser Glu
145                 150                 155                 160
```

```
Arg Cys Gln Gln Cys Cys Ser Ile Gly Lys Ile Phe Tyr Arg Thr Leu
            165                 170                 175
```

(2) INFORMATION FOR SEQ ID NO: 19:

(i) SEQUENCE CHARACTERISTICS:
        (A) LENGTH: 100 amino acids
        (B) TYPE: amino acid
        (D) TOPOLOGY: linear (ii) MOLECULE TYPE: protein (vii) IMMEDIATE SOURCE:
        (B) CLONE: tol.13

(ix) FEATURE:
        (A) NAME/KEY: Protein
        (B) LOCATION: 1..100
        (D) OTHER INFORMATION: /label= UL145

(xi) SEQUENCE DESCRIPTION: SEQ ID NO: 19:

```
Met Cys Thr Asp Pro Arg Arg Thr Ala Gly Trp Glu Arg Leu Thr His
1               5                   10                  15

His Ala Ser Tyr His Ala Asn Tyr Gly Ala Tyr Ala Val Leu Met Ala
            20                  25                  30

Thr Ser Gln Arg Lys Ser Leu Val Leu His Arg Tyr Ser Ala Val Thr
        35                  40                  45

Ala Val Ala Leu Gln Leu Met Pro Val Glu Ile Val Arg Lys Leu Asp
    50                  55                  60

Gln Ser Asp Trp Val Arg Gly Ala Trp Ile Val Ser Glu Thr Phe Pro
65                  70                  75                  80

Thr Ser Asp Pro Lys Gly Val Trp Ser Asp Asp Ser Ser Met Gly
                85                  90                  95

Gly Ser Asp Asp
            100
```

(2) INFORMATION FOR SEQ ID NO: 20:

(i) SEQUENCE CHARACTERISTICS:
        (A) LENGTH: 117 amino acids
        (B) TYPE: amino acid
        (D) TOPOLOGY: linear (ii) MOLECULE TYPE: protein (vii) IMMEDIATE SOURCE:
        (B) CLONE: tol.14

(ix) FEATURE:
        (A) NAME/KEY: Protein
        (B) LOCATION: 1..117
        (D) OTHER INFORMATION: /label= UL146

(xi) SEQUENCE DESCRIPTION: SEQ ID NO: 20:

```
Met Arg Leu Ile Phe Gly Ala Leu Ile Ile Phe Leu Ala Tyr Val Tyr
1               5                   10                  15

His Tyr Glu Val Asn Gly Thr Glu Leu Arg Cys Arg Cys Leu His Arg
            20                  25                  30

Lys Trp Pro Pro Asn Lys Ile Ile Leu Gly Asn Tyr Trp Leu His Arg
        35                  40                  45

Asp Pro Arg Gly Pro Gly Cys Asp Lys Asn Glu His Leu Leu Tyr Pro
    50                  55                  60

Asp Gly Arg Lys Pro Pro Gly Pro Gly Val Cys Leu Ser Pro Asp His
65                  70                  75                  80
```

-continued

```
Leu Phe Ser Lys Trp Leu Asp Lys His Asn Asp Asn Arg Trp Tyr Asn
                85                  90                  95

Val Asn Ile Thr Lys Ser Pro Gly Pro Arg Arg Ile Asn Ile Thr Leu
            100                 105                 110

Ile Gly Val Arg Gly
        115
```

(2) INFORMATION FOR SEQ ID NO: 21:

(i) SEQUENCE CHARACTERISTICS:
        (A) LENGTH: 159 amino acids
        (B) TYPE: amino acid
        (D) TOPOLOGY: linear (ii) MOLECULE TYPE: protein (vii) IMMEDIATE SOURCE:
        (B) CLONE: tol.15

(ix) FEATURE:
        (A) NAME/KEY: Protein
        (B) LOCATION: 1..159
        (D) OTHER INFORMATION: /label= UL147

(xi) SEQUENCE DESCRIPTION: SEQ ID NO: 21:

```
Met Val Leu Thr Trp Leu His His Pro Val Ser Asn Ser His Ile Asn
1               5                   10                  15

Leu Leu Ser Val Arg His Leu Ser Leu Ile Ala Tyr Met Leu Leu Thr
            20                  25                  30

Ile Cys Pro Leu Ala Val His Val Leu Glu Leu Glu Asp Tyr Asp Arg
        35                  40                  45

Arg Cys Arg Cys Asn Asn Gln Ile Leu Leu Asn Thr Leu Pro Val Gly
    50                  55                  60

Thr Glu Leu Leu Lys Pro Ile Ala Ala Ser Glu Ser Cys Asn Arg Gln
65                  70                  75                  80

Glu Val Leu Ala Ile Leu Lys Asp Lys Gly Thr Lys Cys Leu Asn Pro
                85                  90                  95

Asn Ala Gln Ala Val Arg Arg His Ile Asn Arg Leu Phe Phe Arg Leu
            100                 105                 110

Ile Leu Asp Glu Glu Gln Arg Ile Tyr Asp Val Val Ser Thr Asn Ile
        115                 120                 125

Glu Phe Gly Ala Trp Pro Val Pro Thr Ala Tyr Lys Ala Phe Leu Trp
    130                 135                 140

Lys Tyr Ala Lys Arg Leu Asn Tyr His His Phe Arg Leu Arg Trp
145                 150                 155
```

(2) INFORMATION FOR SEQ ID NO: 22:

(i) SEQUENCE CHARACTERISTICS:
        (A) LENGTH: 316 amino acids
        (B) TYPE: amino acid
        (D) TOPOLOGY: linear (ii) MOLECULE TYPE: protein (vii) IMMEDIATE SOURCE:
        (B) CLONE: tol.16

(ix) FEATURE:
        (A) NAME/KEY: Protein
        (B) LOCATION: 1..316
        (D) OTHER INFORMATION: /label= UL148

(xi) SEQUENCE DESCRIPTION: SEQ ID NO: 22:

```
Met Leu Arg Leu Leu Phe Thr Leu Val Leu Leu Ala Leu His Gly Gln
1               5                   10                  15

Ser Val Gly Ala Ser Arg Asp Tyr Val His Val Arg Leu Leu Ser Tyr
            20                  25                  30

Arg Gly Asp Pro Leu Val Phe Lys His Thr Phe Ser Gly Val Arg Arg
        35                  40                  45

Pro Phe Thr Glu Leu Gly Trp Ala Ala Cys Arg Asp Trp Asp Ser Met
    50                  55                  60

His Cys Thr Pro Phe Trp Ser Thr Asp Leu Glu Gln Met Thr Asp Ser
65                  70                  75                  80

Val Arg Arg Tyr Ser Thr Val Ser Pro Gly Lys Glu Val Thr Leu Gln
                85                  90                  95

Leu His Gly Asn Gln Thr Val Gln Pro Ser Phe Leu Ser Phe Thr Cys
            100                 105                 110

Arg Leu Gln Leu Glu Pro Val Val Glu Asn Val Gly Leu Tyr Val Ala
        115                 120                 125

Tyr Val Val Asn Asp Gly Glu Arg Pro Gln Gln Phe Phe Thr Pro Gln
    130                 135                 140

Val Asp Val Val Arg Phe Ala Leu Tyr Leu Glu Thr Leu Ser Arg Ile
145                 150                 155                 160

Val Glu Pro Leu Glu Ser Gly Arg Leu Ala Val Glu Phe Asp Thr Pro
                165                 170                 175

Asp Leu Ala Leu Ala Pro Asp Leu Val Ser Ser Leu Phe Val Ala Gly
            180                 185                 190

His Gly Glu Thr Asp Phe Tyr Met Asn Trp Thr Leu Arg Arg Ser Gln
        195                 200                 205

Thr His Tyr Leu Glu Glu Met Ala Leu Gln Val Glu Ile Leu Lys Pro
    210                 215                 220

Arg Gly Val Arg His Arg Ala Ile Ile His His Pro Lys Leu Gln Pro
225                 230                 235                 240

Gly Val Gly Leu Trp Ile Asp Phe Cys Val Tyr Arg Tyr Asn Ala Arg
                245                 250                 255

Leu Thr Arg Gly Tyr Val Arg Tyr Thr Leu Ser Pro Lys Ala Arg Leu
            260                 265                 270

Pro Ala Lys Ala Glu Gly Trp Leu Val Ser Leu Asp Arg Phe Ile Val
        275                 280                 285

Gln Tyr Leu Asn Thr Leu Leu Ile Thr Met Met Ala Ala Ile Trp Ala
    290                 295                 300

Arg Val Leu Ile Thr Tyr Leu Val Ser Arg Arg
305                 310                 315

(2) INFORMATION FOR SEQ ID NO: 23:

(i) SEQUENCE CHARACTERISTICS:
        (A) LENGTH: 214 amino acids
        (B) TYPE: amino acid
        (D) TOPOLOGY: linear (ii) MOLECULE TYPE: protein (vii) IMMEDIATE SOURCE:
        (B) CLONE: tol.19

(ix) FEATURE:
        (A) NAME/KEY: Protein
        (B) LOCATION: 1..214
        (D) OTHER INFORMATION: /label= UL130

(xi) SEQUENCE DESCRIPTION: SEQ ID NO: 23:
```

```
Met Leu Arg Leu Leu Leu Arg His His Phe His Cys Leu Leu Leu Cys
1               5                   10                  15

Ala Val Trp Ala Thr Pro Cys Leu Ala Ser Pro Trp Ser Thr Leu Thr
            20                  25                  30

Ala Asn Gln Asn Pro Ser Pro Trp Ser Lys Leu Thr Tyr Ser Lys
        35                  40                  45

Pro His Asp Ala Ala Thr Phe Tyr Cys Pro Phe Leu Tyr Pro Ser Pro
    50                  55                  60

Pro Arg Ser Pro Leu Gln Phe Ser Gly Phe Gln Gln Val Ser Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Gln Thr
        115                 120                 125

Ala Ser Lys Pro Ser Asp Gly Asn Val Gln Ile Ser Val Glu Asp Ala
130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
        195                 200                 205

His Pro Asn Leu Ile Ile
    210
```

(2) INFORMATION FOR SEQ ID NO: 24:

(i) SEQUENCE CHARACTERISTICS:
        (A) LENGTH: 122 amino acids
        (B) TYPE: amino acid
        (D) TOPOLOGY: linear (ii) MOLECULE TYPE: protein (vii) IMMEDIATE SOURCE:
        (B) CLONE: tol.20

(ix) FEATURE:
        (A) NAME/KEY: Protein
        (B) LOCATION: 1..122
        (D) OTHER INFORMATION: /label= UL149

(xi) SEQUENCE DESCRIPTION: SEQ ID NO: 24:

```
Met Val Asp Gln Cys Cys Tyr Arg His Leu His Arg Ser Leu Ser Gly
1               5                   10                  15

Gly Pro Asp Val Leu Tyr Ala Ala Gly Thr Gln Arg Glu Gln Gln
            20                  25                  30

Arg Leu Asp Lys Ser Leu Ala Ala Thr Ala Pro Ser Ala Val Ala Gly
        35                  40                  45

Pro Pro Ala Asp Arg Asp Val Val Asp His Arg Thr Glu Thr His Ala
50                  55                  60

Tyr Glu Thr Pro Arg Tyr Ala Thr Arg Cys Leu Thr Arg Tyr Thr Thr
65                  70                  75                  80

Pro Val Arg Ser Ala Val Arg Arg Thr Thr Cys Gly Lys Arg Val Ala
```

```
                    85                  90                  95
Ser Gln Ser Pro Pro Arg Ser Cys Leu Val Ala Pro Gln Ser Ser Pro
               100                 105                 110

Ala His Pro Pro Arg His Pro Glu Gly Gly
           115                 120

(2) INFORMATION FOR SEQ ID NO: 25:

(i) SEQUENCE CHARACTERISTICS:
        (A) LENGTH: 642 amino acids
        (B) TYPE: amino acid
        (D) TOPOLOGY: linear (ii) MOLECULE TYPE: protein (vii) IMMEDIATE SOURCE:
        (B) CLONE: tol.21

(ix) FEATURE:
        (A) NAME/KEY: Protein
        (B) LOCATION: 1..642
        (D) OTHER INFORMATION: /label= UL150

(xi) SEQUENCE DESCRIPTION: SEQ ID NO: 25:

Met Gln Leu Cys Ser His Ser Ile Ser Ser Gln Arg His Val Ala Ser
1               5                  10                  15

Ser Met His Cys Arg Ser Arg His Gln Arg Thr Pro Pro Ser Ala Thr
                20                  25                  30

Thr His Gly Pro Cys Ala Pro Thr Ser Arg Ile Leu Arg Arg Leu Leu
            35                  40                  45

Thr Thr Arg Arg Phe Leu Pro Arg Thr Pro Ser Pro Ser Asn Thr Val
        50                  55                  60

Cys Cys Ile Arg Arg Arg Leu His Glu Arg Thr Ile Arg His Ser Met
65                  70                  75                  80

Arg Cys Arg Arg Arg Asp Met Ala Ser Ser Ala Ser Thr Pro Val Ser
                85                  90                  95

His Thr Gln Pro Leu Ala Ala Asn His Arg Arg Ser Arg Ile Thr Tyr
            100                 105                 110

Ala Thr Thr Asp Pro Thr Asn Ser Pro Thr Ala Ser Pro Ala Lys Ser
        115                 120                 125

Asp Lys Leu Glu Ala Asp Ala Asp Pro Ala Leu His Arg Arg Pro Ala
    130                 135                 140

Ser Leu Leu Arg His Leu Phe Gln Pro Cys His Ala Gln Arg Gly Thr
145                 150                 155                 160

Ser Asn Arg Ala Thr Ser Gln Arg Ala Ser Leu Asn Ala Val His His
                165                 170                 175

Lys Leu Cys Gly Ala Met Ile Ser Ser Cys Ser Thr Thr Cys Thr
            180                 185                 190

Pro Leu Ile Met Asp Leu Pro Ser Leu Ser Val Glu Leu Ser Ala Gly
        195                 200                 205

His Lys Lys Lys Glu Thr Pro Thr Glu Gly Gly Trp Gly Gly Glu Glu
    210                 215                 220

Gly Glu Asp Asp Val Leu Ala Thr Ile Arg Asn Thr Leu Ser Ala Pro
225                 230                 235                 240

Thr Ser Pro Ala Ala Ala Thr Thr His Arg Leu Ser Phe Pro Gly Glu
                245                 250                 255

Ser Thr Phe Cys Leu Thr Ala Val Ser Glu Cys Ser Gln Arg Arg Thr
            260                 265                 270
```

-continued

```
Ser Thr Ala Ala Leu Thr Pro Pro Pro Ala Val Ala Ala Phe
        275                 280                 285

Ser Phe Ser Ser Thr Val Ser Glu Thr Gly Thr Phe Pro Gln Ser Thr
        290                 295                 300

Thr Gly Arg Thr Arg Val Asp Asp Thr Ala Val Val Thr Ala Gly Asp
305                 310                 315                 320

Pro Arg Ser Pro Val Thr His Val Thr Leu Leu Gln Ile Phe Arg Leu
                325                 330                 335

Arg Ser Ser Leu Leu Thr Ser Arg Ser Gly Ala Leu Arg Gly Gly
            340                 345                 350

Glu His Glu Ala Ile Pro Lys Val Ala Ser Leu Phe Trp Thr Leu Leu
        355                 360                 365

Lys Ala Thr Gln Ile Val Glu Met Thr His Lys Thr Pro Ser Ala Asp
370                 375                 380

Ser His Arg Asn Pro Gln Lys Tyr Thr Asp Arg Pro Gln Arg Leu Leu
385                 390                 395                 400

Leu Thr Ala Leu Ala Ile Trp Gln Arg Thr Tyr Asn Asp Thr Arg Ala
                405                 410                 415

Ala His Ala Pro Gln Val Arg Leu Leu Gly Asp Ile Leu Thr Tyr Arg
                420                 425                 430

Arg Pro Gln Thr Ala Thr Ala Ser Thr Lys Ala His Thr Gln Gln Gln
            435                 440                 445

Pro Glu Glu Pro Lys Gly Gln Gln Ile Trp Thr Gln Thr Ala Gly Gln
        450                 455                 460

Ala Ala Pro His Gly Asp Glu Pro His Ser Asp Gly Glu Leu Arg Arg
465                 470                 475                 480

Glu Ser His Ser Ala Pro Pro Thr Ser Arg Thr Leu Pro Asp Thr Ile
                485                 490                 495

Leu Ala Val Lys Arg Arg Ser Val Ala Gln Arg Ser His Val Arg Leu
                500                 505                 510

Asp Ala Lys Pro Gly Leu Asn Glu Arg Asp Gly Phe Arg Gln Arg Leu
            515                 520                 525

Leu Leu Pro Leu Ser Gly Tyr Phe Arg Ala Asn Glu Leu Arg Asn Gln
        530                 535                 540

Gln Phe Met Gly Tyr Gly Thr Lys Asn Gly Leu Lys Asn Thr Trp Leu
545                 550                 555                 560

Thr Arg Pro Leu Gly Val Ala Gly Gly Val Arg Glu Thr Ile Gly Glu
                565                 570                 575

Arg Gln Asp Arg Asn Val Ala Asp Ser Ala Thr Gln Arg Val Phe His
                580                 585                 590

Thr Leu Tyr Ala Ala Leu Gln Thr Val Arg Val Trp Tyr Thr Ala Leu
            595                 600                 605

Gly Thr Ala Trp Arg Thr Ser Gly Ser Arg Thr Arg Glu Ser Leu Phe
        610                 615                 620

Asp Gly Pro Arg Arg Arg Asp Arg Gln Ala Ala Arg Leu Arg Arg Leu
625                 630                 635                 640

Glu Leu
```

(2) INFORMATION FOR SEQ ID NO: 26:

(i) SEQUENCE CHARACTERISTICS:
        (A) LENGTH: 336 amino acids
        (B) TYPE: amino acid
        (D) TOPOLOGY: linear -continued

```
    (ii) MOLECULE TYPE: protein (vii) IMMEDIATE SOURCE:
         (B) CLONE: tol.22

(ix) FEATURE:
         (A) NAME/KEY: Protein
         (B) LOCATION: 1..336
         (D) OTHER INFORMATION: /label= UL151

(xi) SEQUENCE DESCRIPTION: SEQ ID NO: 26:

Met Val Phe Val Ser Gly Thr Ala Leu Gly Thr Gly Phe His Arg Ala
1               5                  10                  15

Glu Gly Ser Phe Cys Gly Cys Glu Gly Arg Ser Phe Phe Arg Thr Leu
            20                  25                  30

Gly Thr Gly Leu Gly Asp Gly Gly Cys Ala Gly Arg Arg Trp Xaa Arg
        35                  40                  45

Xaa Val Ala Gly Thr Gly Ile Thr Leu Gly Thr Gly Thr Arg Gly Pro
50                  55                  60

Gly Leu Arg Asp Gly Gly Asp Gly Gly Val Cys Gly Glu Asp Gly Gly
65                  70                  75                  80

Leu Leu Arg Arg Gly Arg Gly Leu Ala Gly Pro Ala Val Ala Gly Val
                85                  90                  95

Cys Gly Asp Gly Gly Leu Leu Gln Arg Arg Gly Leu Arg Gly Gln Glu
            100                 105                 110

Cys Ala Xaa Pro Gly Gly Phe Ala Gly Gly His Gly Thr Gly Gly Gly
        115                 120                 125

Gly Asp Ser Thr Asn His Thr His Thr Gln Leu Thr Ser Ala Val Ala
130                 135                 140

Leu Ser Glu Pro Pro Leu Phe Phe Ile Asn Val Leu Ile Pro Pro Ala
145                 150                 155                 160

Tyr Thr Arg Asn Ala Ala Cys Ser Tyr Ala His Thr Leu Ser Leu His
                165                 170                 175

Ser Asp Met Leu Leu Arg Leu Cys Thr Ala Ala Ala Asp Thr Ser Gly
            180                 185                 190

His Arg His Leu Pro Pro His Met Ala His Val Leu Arg Arg Pro Ala
        195                 200                 205

Ser Tyr Val Val Cys Ser Gln His Gly Ala Phe Phe Pro Ala Arg His
210                 215                 220

Leu His Arg Thr Pro Ser Ala Ala Phe Ala Val Ala Ser Thr Arg Glu
225                 230                 235                 240

Gln Tyr Ala Thr Ala Cys Ala Val Ala Ala Thr Trp Pro Pro Arg
                245                 250                 255

Leu Pro His Leu Phe Arg Thr Pro Asn Leu Trp Leu Pro Thr Thr Asp
            260                 265                 270

Val Gln Gly Ser Arg Thr Arg Arg Pro Ile Pro Pro Ile Leu Gln Arg
        275                 280                 285

Pro Arg Pro Pro Ser Gln Thr Ser Trp Lys Pro Thr Gln Thr Gln His
290                 295                 300

Ser Ile Asp Ala Arg Pro Arg Cys Cys Ala Thr Ser Ser Ser Pro Ala
305                 310                 315                 320

Thr Pro Asn Ala Ala Leu Pro Thr Glu Pro His Pro Arg Gly Leu Pro
                325                 330                 335

(2) INFORMATION FOR SEQ ID NO: 27:

(i) SEQUENCE CHARACTERISTICS:
```

```
    (A) LENGTH: 270 amino acids
    (B) TYPE: amino acid
    (D) TOPOLOGY: linear (ii) MOLECULE TYPE: protein (vii) IMMEDIATE SOURCE:
      (B) CLONE: tol.23

(ix) FEATURE:
     (A) NAME/KEY: Protein
     (B) LOCATION: 1..270
     (D) OTHER INFORMATION: /label= UL132

(xi) SEQUENCE DESCRIPTION: SEQ ID NO: 27:
```

Met Pro Ala Leu Arg Gly Pro Leu Arg Ala Thr Phe Leu Ala Leu Val
1               5                   10                  15

Ala Phe Gly Leu Leu Gln Ile Asp Leu Ser Asp Ala Thr Asn Val
            20                  25                  30

Thr Ser Ser Thr Lys Val Pro Thr Ser Thr Ser Asn Arg Asn Asn Val
            35                  40                  45

Asp Asn Ala Thr Ser Ser Gly Pro Thr Thr Gly Ile Asn Met Thr Thr
50                      55                  60

Thr His Glu Ser Ser Val His Asn Val Arg Asn Asn Glu Ile Met Lys
65                  70                  75                  80

Val Leu Ala Ile Leu Phe Tyr Ile Val Thr Gly Thr Ser Ile Phe Ser
                85                  90                  95

Phe Ile Ala Val Leu Ile Ala Val Val Tyr Ser Ser Cys Cys Lys His
                100                 105                 110

Pro Gly Arg Phe Arg Phe Ala Asp Glu Glu Ala Val Asn Leu Leu Asp
            115                 120                 125

Asp Thr Asp Asp Ser Gly Gly Ser Ser Pro Phe Gly Ser Gly Ser Arg
130                 135                 140

Arg Gly Ser Gln Ile Pro Ala Gly Phe Cys Ser Ser Ser Pro Tyr Gln
145                 150                 155                 160

Arg Leu Glu Thr Arg Asp Trp Asp Glu Glu Glu Ala Ser Ala Ala
                165                 170                 175

Arg Glu Arg Met Lys His Asp Pro Glu Asn Val Ile Tyr Phe Arg Lys
                180                 185                 190

Asp Gly Asn Leu Asp Thr Ser Phe Val Asn Pro Asn Tyr Gly Arg Gly
            195                 200                 205

Ser Pro Leu Thr Ile Glu Ser His Leu Ser Asp Asn Glu Glu Asp Pro
210                 215                 220

Ile Arg Tyr Tyr Val Ser Val Tyr Asp Glu Leu Thr Ala Ser Glu Met
225                 230                 235                 240

Glu Glu Pro Ser Asn Ser Thr Ser Trp Gln Ile Pro Lys Leu Met Lys
                245                 250                 255

Val Ala Met Gln Pro Val Ser Leu Arg Asp Pro Glu Tyr Asp
                260                 265                 270